(12) United States Patent
Matsuda et al.

(10) Patent No.: US 8,420,821 B2
(45) Date of Patent: Apr. 16, 2013

(54) PROCESS FOR PRODUCTION OF 4-OXOQUINOLINE COMPOUND

(75) Inventors: Koji Matsuda, Osaka (JP); Koji Ando, Osaka (JP); Shigeji Ohki, Osaka (JP); Takahiro Yamasaki, Osaka (JP); Jun-ichi Hoshi, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 947 days.

(21) Appl. No.: 12/281,921

(22) PCT Filed: Mar. 6, 2007

(86) PCT No.: PCT/JP2007/054311
§ 371 (c)(1), (2), (4) Date: Sep. 5, 2008

(87) PCT Pub. No.: WO2007/102499
PCT Pub. Date: Sep. 13, 2007

(65) Prior Publication Data
US 2009/0318702 A1 Dec. 24, 2009

(30) Foreign Application Priority Data

Mar. 6, 2006 (JP) .................................. 2006-060274
Mar. 6, 2006 (JP) .................................. 2006-060297

(51) Int. Cl.
*C07D 215/233* (2006.01)
(52) U.S. Cl.
USPC ...................................................... 546/156
(58) Field of Classification Search ................... None
See application file for complete search history.

(56) References Cited

U.S. PATENT DOCUMENTS

| 3,472,859 A | 10/1969 | Lesher et al. |
| 4,695,646 A | 9/1987 | Maurer et al. |

(Continued)

FOREIGN PATENT DOCUMENTS

| EP | 0 287 951 | 10/1988 |
| EP | 0 319 906 | 6/1989 |

(Continued)

OTHER PUBLICATIONS

Dinescu, L. et al., "Design of Photonic Liquid Crystal Materials: Synthesis and Evaluation of New Chiral Thioindigo Dopants Designed to Photomodulate the Spontaneous Polarization of Ferroelectric Liquid Crystals," J. Mater. Chem., vol. 9, No. 8, pp. 1679-1686 (1999).

(Continued)

*Primary Examiner* — Kamal Saeed
(74) *Attorney, Agent, or Firm* — Finnegan, Henderson, Farabow, Garrett & Dunner, LLP

(57) ABSTRACT

The present invention provides a compound useful as a synthetic intermediate for an anti-HIV agent having an integrase inhibitory activity, a production method thereof, and a production method of an anti-HIV agent using the synthetic intermediate. Specifically, the present invention provides, for example, compounds represented by the formulas (6), (7-1), (7-2) and (8):

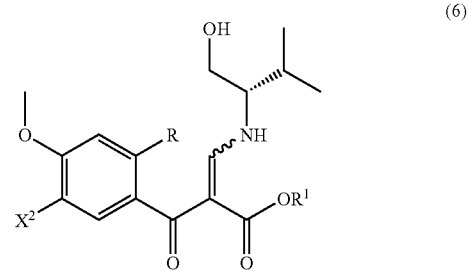

(6)

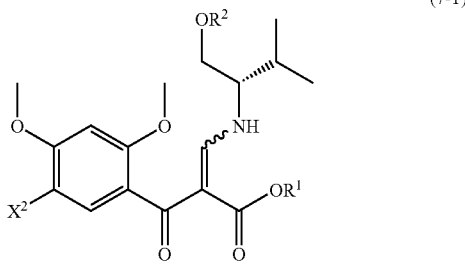

(7-1)

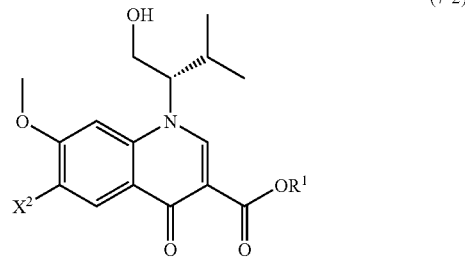

(7-2)

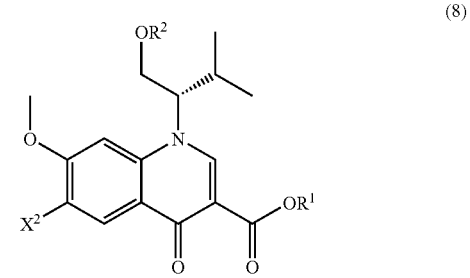

(8)

wherein R is a fluorine atom or a methoxy group, $R^1$ is a $C_1$-$C_4$ alkyl group, $R^2$ is a hydroxyl-protecting group, and $X^2$ is a halogen atom, a production method thereof, and a production method of an anti-HIV agent using the synthetic intermediate.

5 Claims, No Drawings

U.S. PATENT DOCUMENTS

| | | | |
|---|---|---|---|
| 5,182,401 A | 1/1993 | Grohe | |
| 5,217,972 A | 6/1993 | Grohe et al. | |
| 5,686,482 A | 11/1997 | Ohmori et al. | |
| 5,989,451 A | 11/1999 | Lemieux et al. | |
| 7,176,220 B2 | 2/2007 | Satoh et al. | |
| 2006/0019906 A1 | 1/2006 | Satoh et al. | |
| 2006/0030710 A1 | 2/2006 | Satoh et al. | |
| 2008/0125594 A1* | 5/2008 | Dowdy et al. | 546/156 |
| 2009/0036684 A1 | 2/2009 | Matsuda et al. | |
| 2009/0099366 A1 | 4/2009 | Dowdy et al. | |

FOREIGN PATENT DOCUMENTS

| | | |
|---|---|---|
| EP | 0 326 891 | 8/1989 |
| EP | 0 457 090 | 11/1991 |
| EP | 0905558 A | 3/1999 |
| JP | 11-084556 | 3/1999 |
| JP | 2006-001927 | 1/2006 |
| WO | WO 95/29891 A1 | 11/1995 |
| WO | WO 98/34995 A1 | 8/1998 |
| WO | WO 99/52857 | 10/1999 |
| WO | WO 00/40561 | 7/2000 |
| WO | WO 01/98275 | 12/2001 |
| WO | WO 02/04444 | 1/2002 |
| WO | WO 02/48113 | 6/2002 |
| WO | WO 03/043992 A1 | 5/2003 |
| WO | WO 2004/046115 A1 | 6/2004 |
| WO | WO 2005/113508 A1 | 12/2005 |
| WO | WO 2005/113509 A1 | 12/2005 |
| WO | WO 2007/102512 A1 | 9/2007 |
| WO | WO 2008/033836 A2 | 3/2008 |
| WO | WO 2009/036161 A1 | 3/2009 |

OTHER PUBLICATIONS

Gualtieri, F. et al., A Direct Metalation Approach to 2-Alkylthio-2,2-Diaryl Substituted Acetic Acids, Synlett, vol. 5, pp. 447-448 (1996).

Malamas, M.S. et al., "Design and synthesis of aryl diphenolic azoles as potent and selective estrogen receptor-β ligands," J. Med. Chem. 2004, vol. 47, No. 21, pp. 5021-5040.

Perry, R.J., "Synthesis of Polyimides via the Palladium-Catalyzed Carbonylation of Bis(o-iodo Esters) and Diamines," Macromolecules, vol. 28, pp. 3509-3515 (1995).

Šulcová, V., "Effect of Derivatives of 3-Quinolinecarboxylic Acid on DNA Synthesis, Growth and Division in *Escherichia coli* 15 TAU," Folia Microbiologica, vol. 19, No. 4, pp. 281-291 (1974).

Zhurnal Organicheskoi Khimi 6,1, pp. 68-71 (1970).

International Search Report for Application No. PCT/JP2007/054311 dated Jun. 5, 2007.

International Search Report for Application No. PCT/JP2007/054348 dated Jun. 5, 2007.

Bouzard, D. et al., "Fluoronaphthyridines and Quinolones as Antibacterial Agents. 1. Synthesis and Structure-Activity Relationships of New 1-Substituted Derivatives," Journal of Medicinal Chemistry, American Chemical Society, Washington, US, vol. 32, No. 3, pp. 537-542 (Jan. 1, 1989).

Domagala, J.M. et al., "1-Substituted 7-[3-[(Ethylamino)methyl]-1-pyrrolidinyl]-6,8-difluoro-1,4-dihydro-4-oxo-3-quinolinecarboxylic Acids. New Quantitative Structure-Activity Relationships at $N_1$ for the Quinolone Antibacterials," Journal of Medicinal Chemistry, vol. 31, pp. 991-1001 (1988).

Extended European Search Report for European Patent Application No. 10011216.8, dated Feb. 15, 2011.

* cited by examiner

PROCESS FOR PRODUCTION OF 4-OXOQUINOLINE COMPOUND

TECHNICAL FIELD OF THE INVENTION

The present invention relates to a compound useful as a synthesis intermediate for an anti-HIV agent having an integrase inhibitory activity and a production method thereof. In addition, the present invention relates to a production method of an anti-HIV agent using the synthesis intermediate and the like.

BACKGROUND OF THE INVENTION

Patent reference 1 discloses a production method of a 4-oxoquinoline compound represented by the formula [II]:

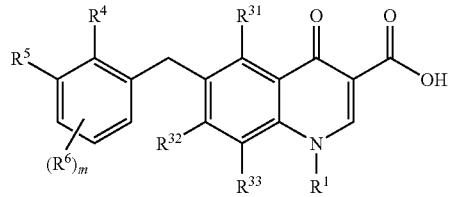

wherein each symbol is as defined in patent reference 1 (hereinafter sometimes to be abbreviated as compound [II]). Specifically, the following production methods are known.

Production Method 1-1 (See Patent Reference 1: Page 67)

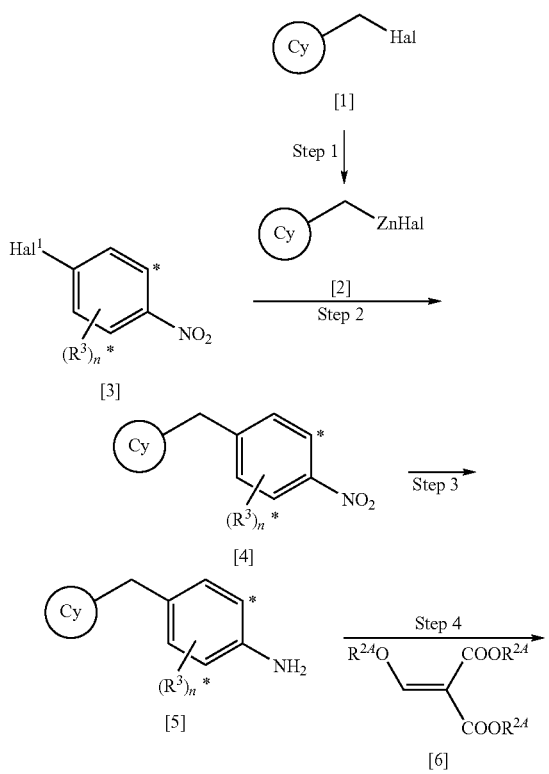

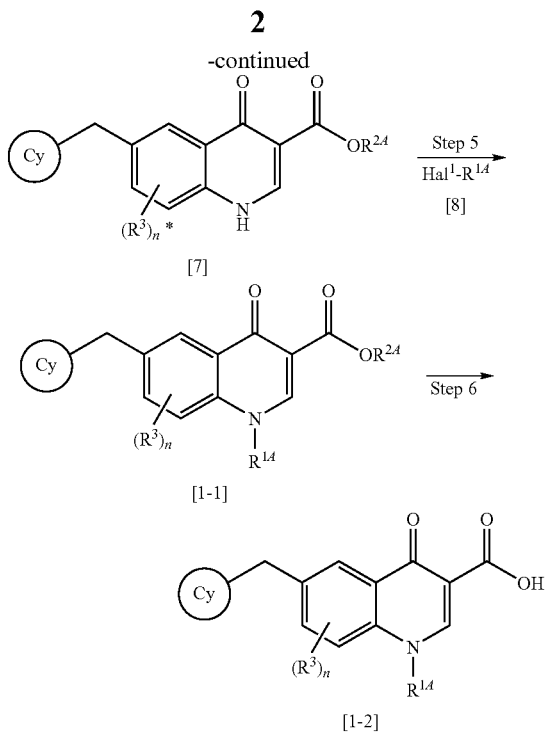

Each symbol in the scheme is as defined in patent reference 1.

This production method is also described in patent reference 2, page 64 (each symbol in the scheme is also defined in patent reference 2).

Production Method 1-2 Example of Production Method Using Compound [9], into which Hydroxyl-Protecting Group has Been Introduced (See Patent Reference 1: Page 71)

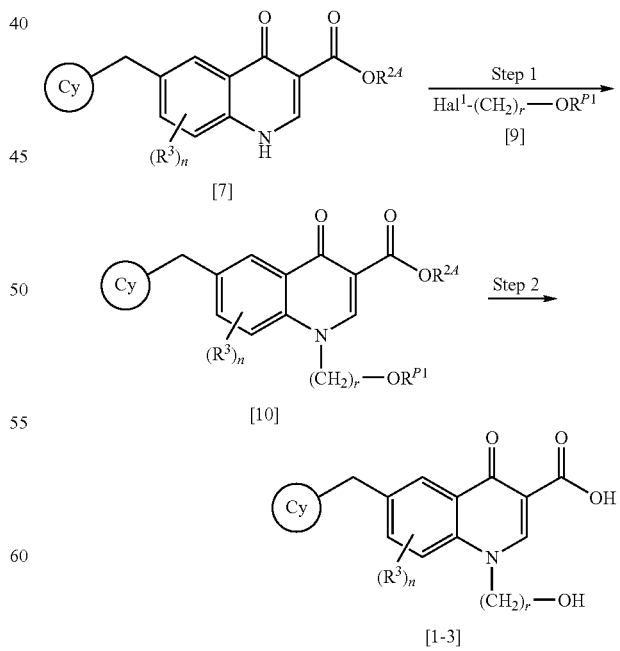

Each symbol in the scheme is as defined in patent reference 1.

This production method is also described in patent reference 2, page 68 (each symbol in the scheme is also defined in patent reference 2).

Production Method 2-1 (See Patent Reference 1: Page 72)

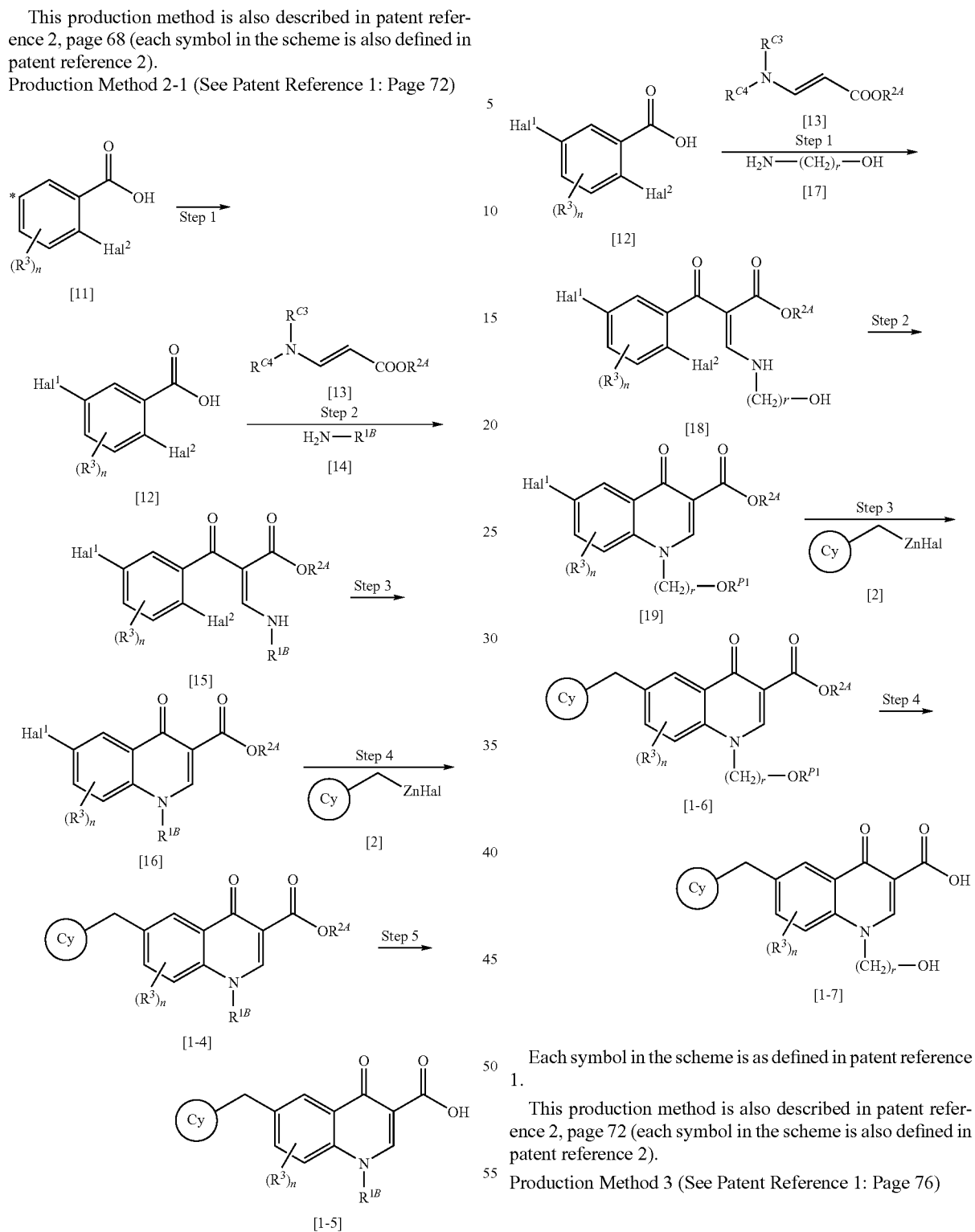

Each symbol in the scheme is as defined in patent reference 1.

This production method is also described in patent reference 2, page 69 (each symbol in the scheme is also defined in patent reference 2).

Production Method 2-2 Example of Production Method Including Introduction-Deprotection Step of Hydroxyl-Protecting Group (See Patent Reference 1: Page 74)

Each symbol in the scheme is as defined in patent reference 1.

This production method is also described in patent reference 2, page 72 (each symbol in the scheme is also defined in patent reference 2).

Production Method 3 (See Patent Reference 1: Page 76)

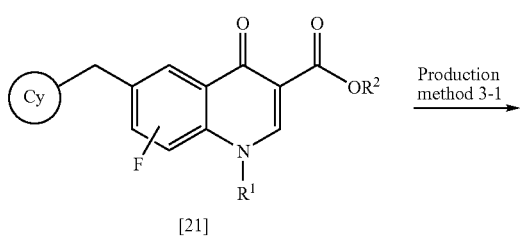

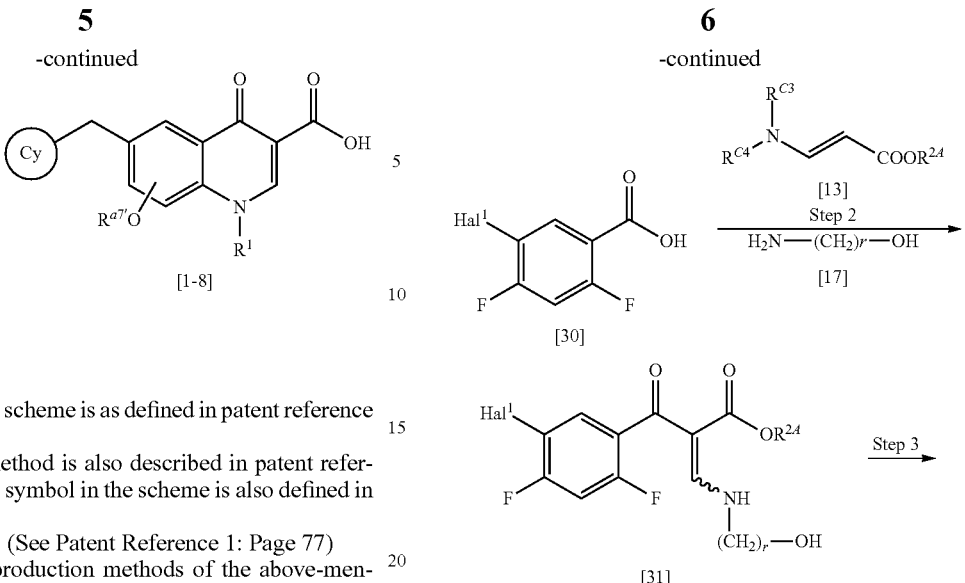

Each symbol in the scheme is as defined in patent reference 1.

This production method is also described in patent reference 2, page 74 (each symbol in the scheme is also defined in patent reference 2).

Production Method 4 (See Patent Reference 1: Page 77)

Examples of the production methods of the above-mentioned compound [12] are specifically shown in the following.

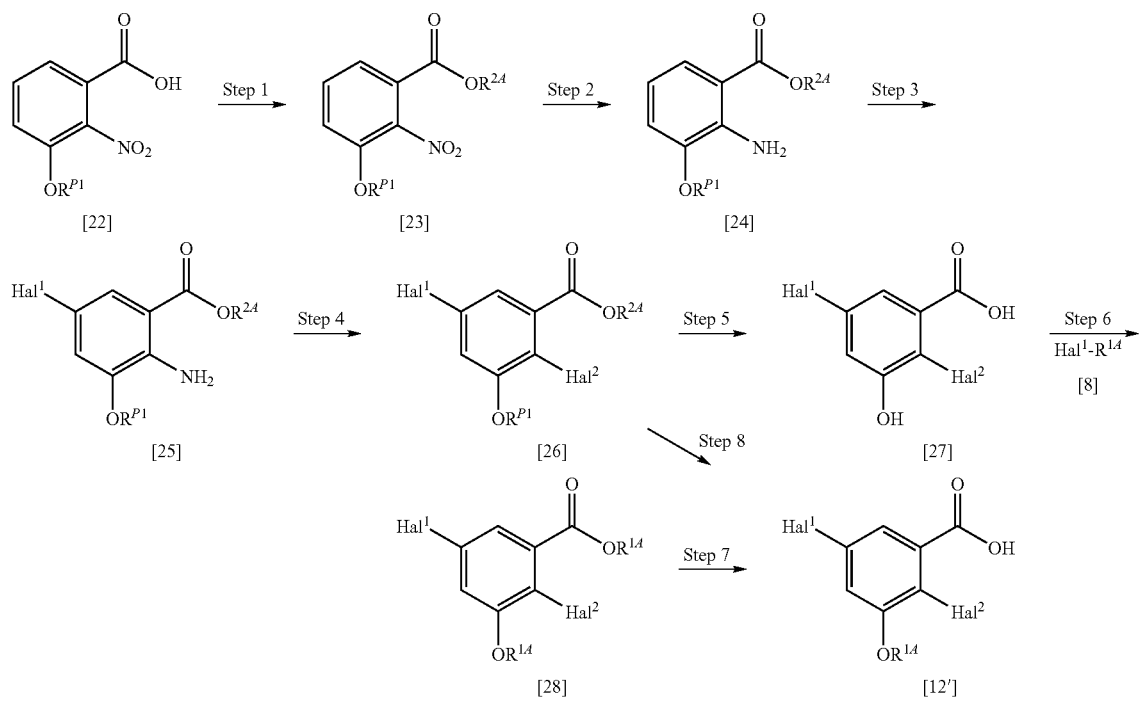

Each symbol in the scheme is as defined in patent reference 1.

Production Method 5 (See Patent Reference 1: Page 79)

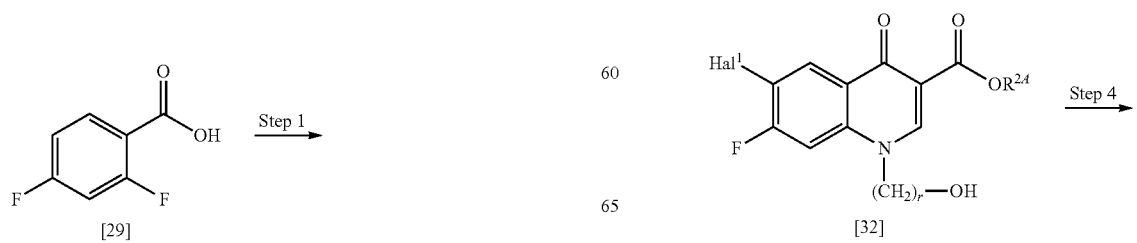

-continued

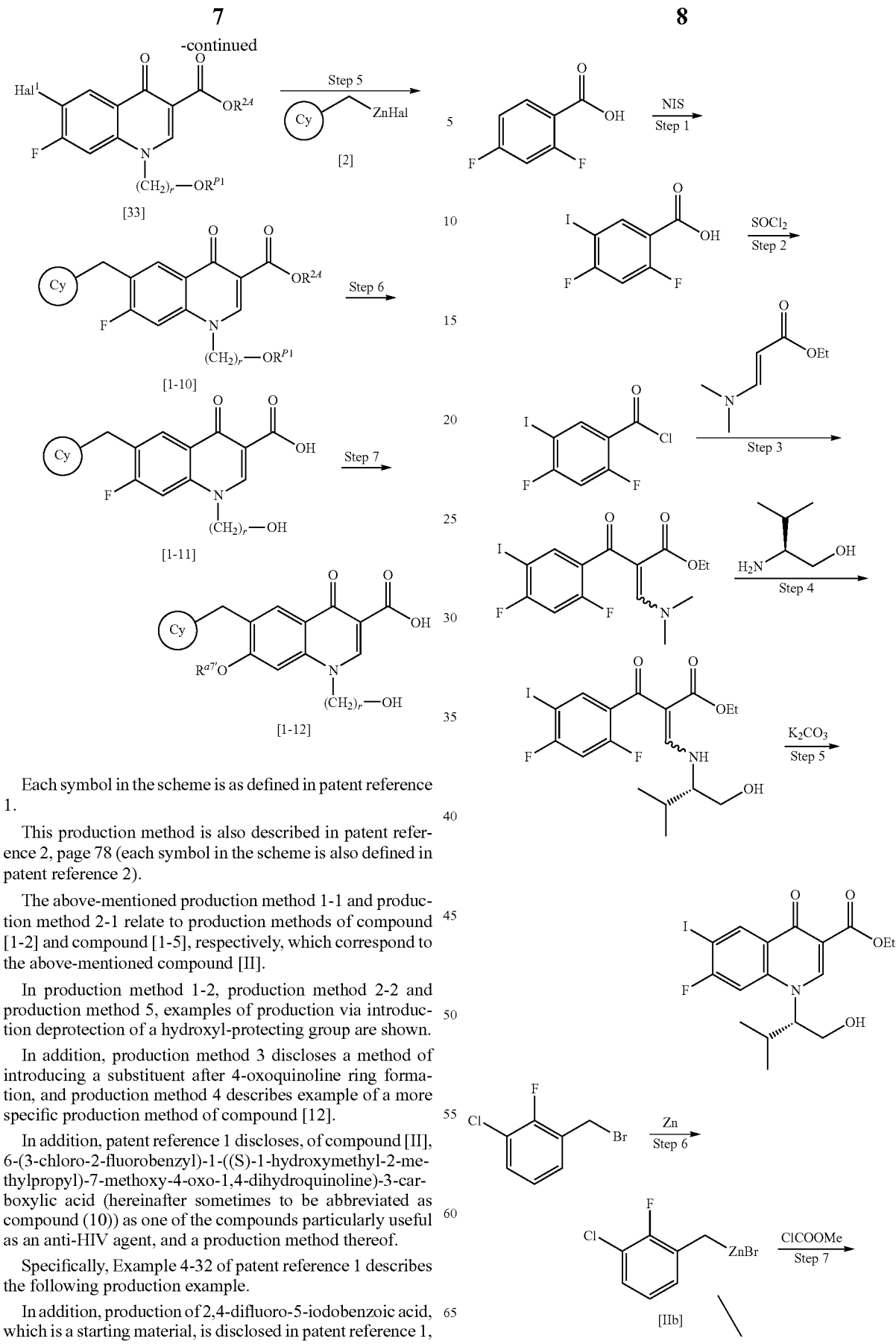

Each symbol in the scheme is as defined in patent reference 1.

This production method is also described in patent reference 2, page 78 (each symbol in the scheme is also defined in patent reference 2).

The above-mentioned production method 1-1 and production method 2-1 relate to production methods of compound [1-2] and compound [1-5], respectively, which correspond to the above-mentioned compound [II].

In production method 1-2, production method 2-2 and production method 5, examples of production via introduction deprotection of a hydroxyl-protecting group are shown.

In addition, production method 3 discloses a method of introducing a substituent after 4-oxoquinoline ring formation, and production method 4 describes example of a more specific production method of compound [12].

In addition, patent reference 1 discloses, of compound [II], 6-(3-chloro-2-fluorobenzyl)-1-((S)-1-hydroxymethyl-2-methylpropyl)-7-methoxy-4-oxo-1,4-dihydroquinoline)-3-carboxylic acid (hereinafter sometimes to be abbreviated as compound (10)) as one of the compounds particularly useful as an anti-HIV agent, and a production method thereof.

Specifically, Example 4-32 of patent reference 1 describes the following production example.

In addition, production of 2,4-difluoro-5-iodobenzoic acid, which is a starting material, is disclosed in patent reference 1, Example 4-33, step 1.

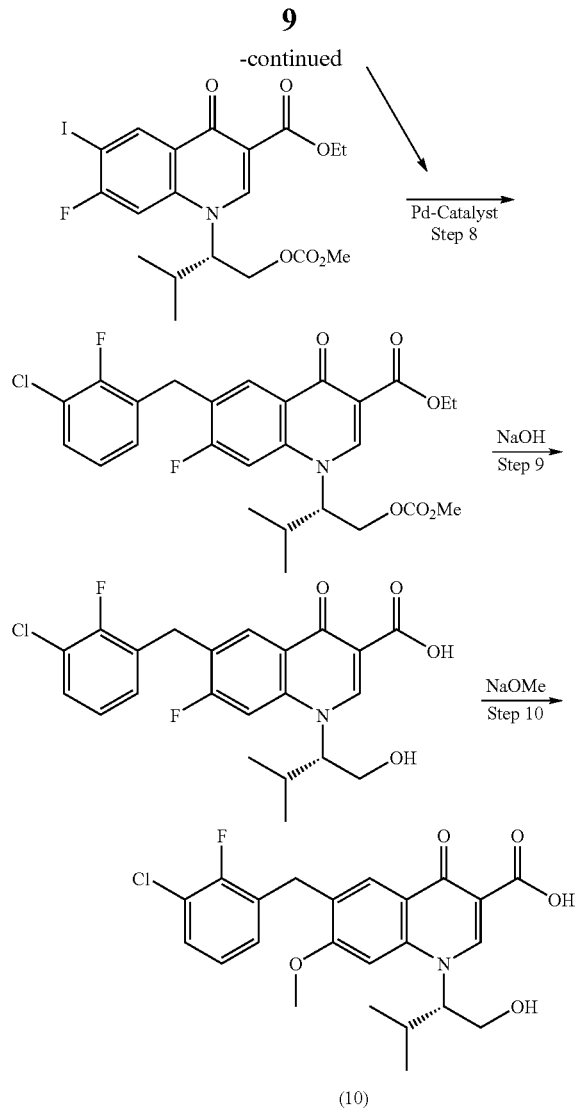

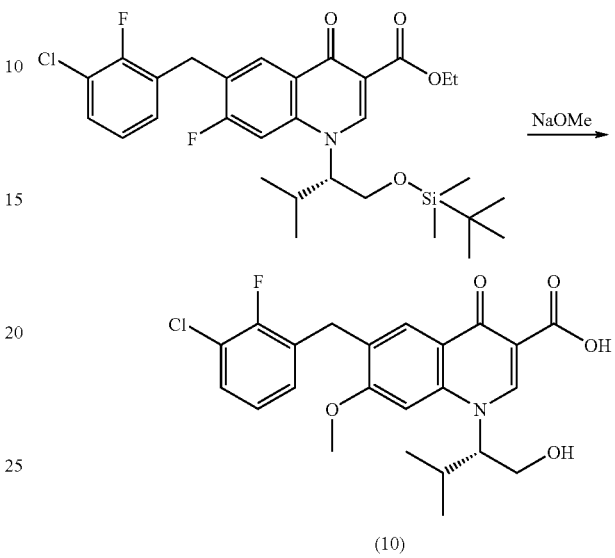

wherein NIS is N-iodosuccinimide, catalyst shows a catalyst, and other symbols are as defined in patent reference 1.

This production method is also described in patent reference 2, page 112, Reference Example 9.

As a production method similar to this production method, patent reference 3, page 23, Example 2-1 describes a production method wherein the hydroxyl-protecting group is a tert-butyl dimethylsilyl group. In addition, patent reference 3, page 12, Reference Example 1; page 17, Example 1 and page 39 and Example 2-4 describe a method of directly producing compound (10) from a compound wherein the hydroxyl-protecting group is a tert-butyldimethylsilyl group.

Moreover, patent reference 1, page 81, Reference Example 1, and patent reference 2, page 80 or Reference Example 1 disclose that 2,3-dichlorobenzylzinc chloride which is an analog of 3-chloro-2-fluorobenzylzinc bromide produced in the above-mentioned step 6 can be produced in the same manner from 2,3-dichlorobenzyl chloride.

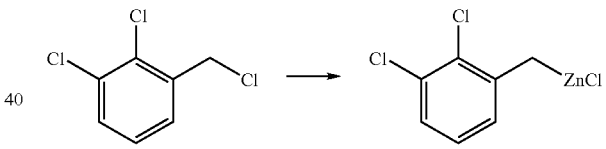

Patent reference 3 discloses a production method of compound (10).

Specifically, patent reference 3, Example 2-2, page 28 describes the following production example.

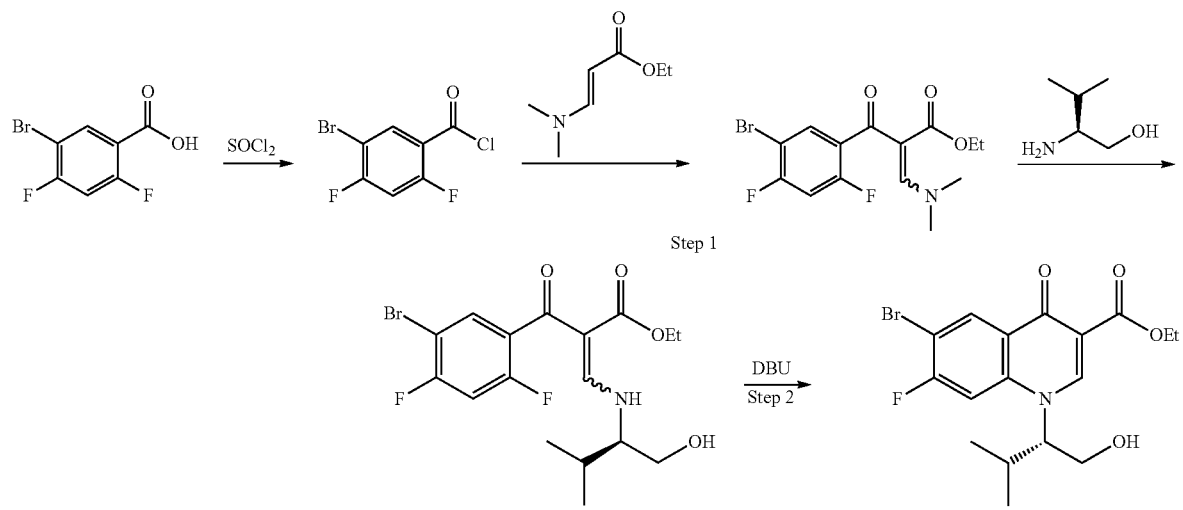

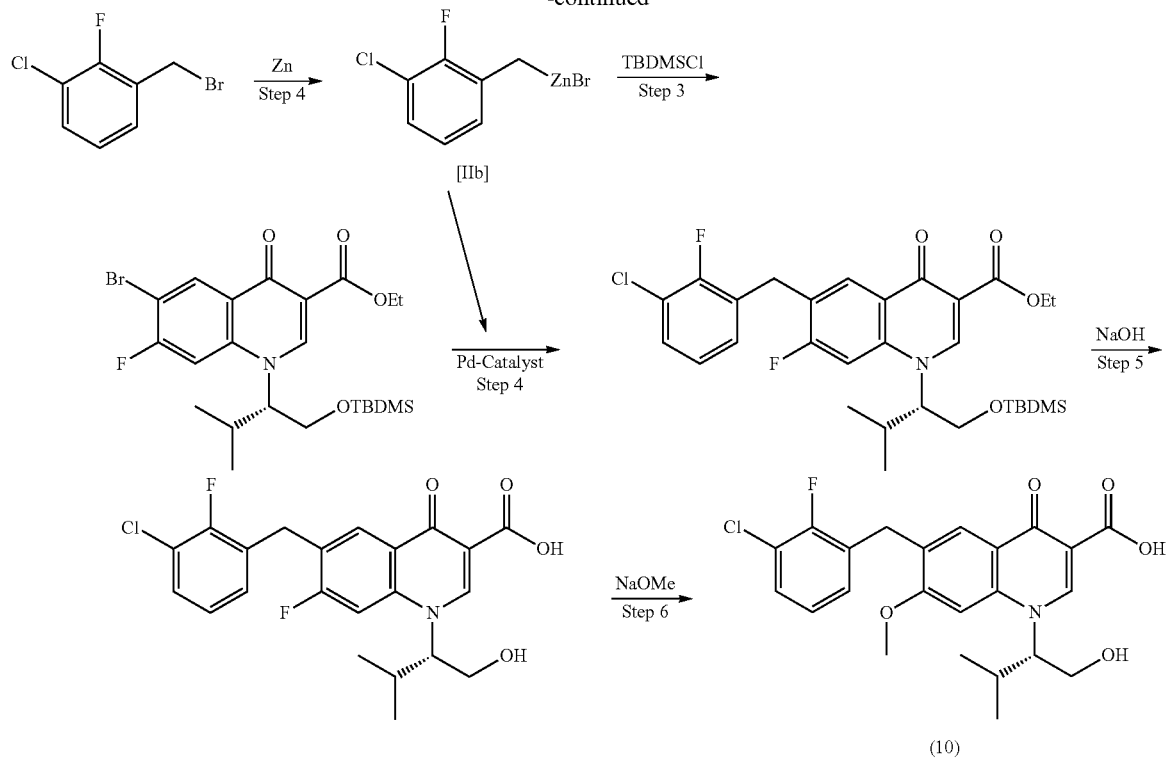

wherein DBU is 1,8-diazabicyclo[5.4.0]undecene, catalyst shows a catalyst, and other symbols are as defined in patent reference 3.

Patent reference 1, patent reference 2 and patent reference 3 disclose production methods of compound (10). The references have the following aspects.

In the final step (alkoxylation, particularly methoxylation), a dimer is by-produced depending on the base to be used. Thus, in this event, a removal step of the by-produced dimmer is further necessary, which decreases the yield greatly.

When sodium fluoride by-produced in the final step (alkoxylation, particularly methoxylation) is acidified in the treatment step, hydrofluoric acid is produced, which corrodes the production facility. Thus, a removal operation of sodium fluoride is essential and the operation is complicated.

There is a concern about an unfavorable influence of hydrofluoric acid produced in the ring-closing step on the production facility, and therefore, the method is not of a level satisfactory as an industrial production method.

Removal of the product by-produced in a reaction to insert compound [IIb] is complicated (since alkyl zinc derivative is used with a palladium catalyst, an operation to remove zinc salt and palladium salt as impurities is necessary and the operation is complicated).

Plural operations are necessary to protect hydroxyl group with methyl chloroformate in a preliminary step of the reaction to insert compound [IIb], and to deprotect the group in a later step, and the operation is complicated.

A step using 3-chloro-2-fluorobenzyl bromide for the production of compound [IIb] is not beneficial for industrial production since the compound shows high tearing property.

The above-mentioned production methods including these steps are associated with many aspects to be improved for industrial production, and the development of a more superior production method of compound (10) is desired.

In addition, while non-patent reference 1 describes the following 4-oxoquinoline compound and the like, the compounds (8) and (9) of the present invention, which are explained in detail in the following, are not described.

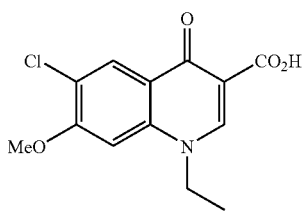 [SMILES: CCn1cc(C(=O)O)c(=O)c2cc(Cl)c(OC)cc21]

In addition, while Example 1 (1c) of patent reference 4 describes the following acrylic acid ester and the like, the compounds (6) {(6-A) and (6-B)}, and (7-1) of the present invention, which are explained in detail in the following, are not described.

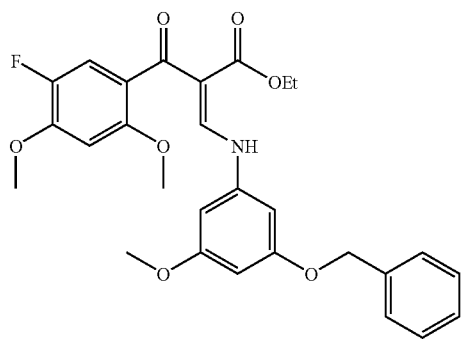 [SMILES: CCOC(=O)/C(=C\Nc1cc(OC)cc(OCc2ccccc2)c1)C(=O)c1cc(F)c(OC)cc1OC]

Moreover, patent reference 5 describes a production example of 4-oxoquinoline skeleton from the following acrylic acid ester and the like, in a ring-closing reaction during formation of 4-oxoquinoline skeleton. However, a production method from compound (7-1) to compound (8) and a production method from compound (6-B) to compound (7-2) like those in the present invention explained in detail in the following are not described.

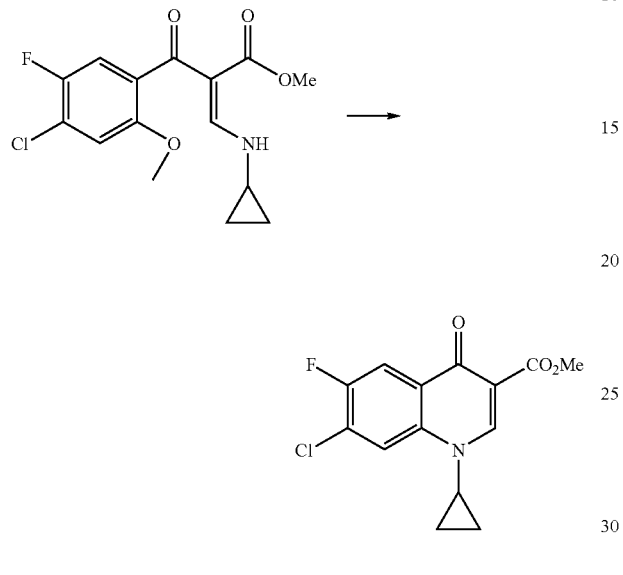

[Patent reference 1] WO 04/046115
[Patent reference 2] WO 05/113509
[Patent reference 3] WO 05/113508
[Patent reference 4] WO 03/043992 (page 195, line 10)
[Patent reference 5] U.S. Pat. No. 4,695,646 (column 15, line 40)
[Non-patent reference 1] Folia Microbiologica, vol. 19, number 4, pages 281-291, 1974 (page 282, FIG. 1)

DISCLOSURE OF THE INVENTION

Problems to be Solved by the Invention

An object of the present invention is to provide a compound useful as a synthetic intermediate for an anti-HIV agent having an integrase inhibitory activity and a production method thereof, and a production method of an anti-HIV agent using the synthetic intermediate.

Means of Solving the Problems

In view of the above-mentioned object, the present inventors have conducted intensive studies in an attempt to find an improved production method of the above-mentioned compound [II], particularly compound (10), and found that compounds represented by the formulas (6), (7-1), (7-2) and (8) (hereinafter sometimes to be abbreviated as compounds (6), (7-1), (7-2) and (8), respectively) are useful as synthetic intermediates therefor, which resulted in the completion of the present invention.

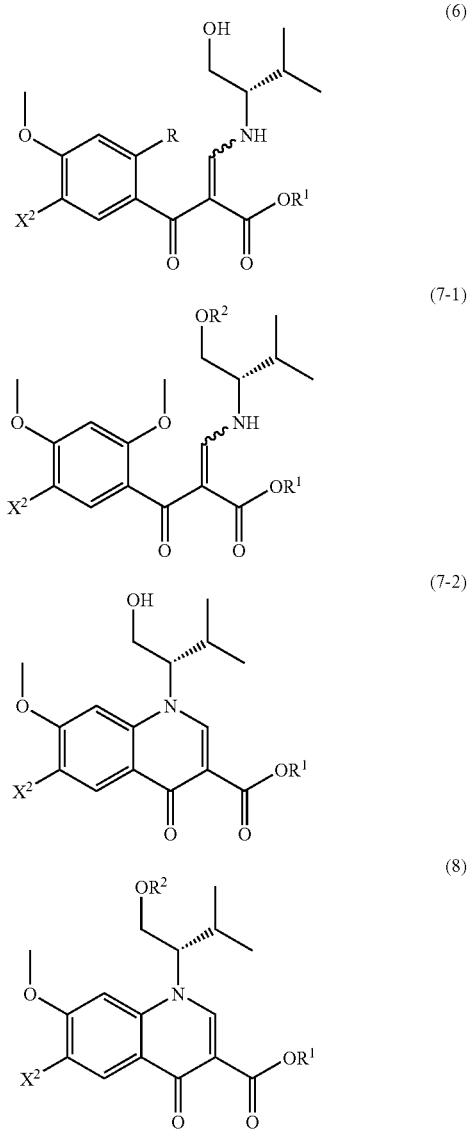

wherein R is a fluorine atom or a methoxy group, $R^1$ is a $C_1$-$C_4$ alkyl group, $R^2$ is a hydroxyl-protecting group and $X^2$ is a halogen atom.

More specifically, the present invention is as shown in the following [1]-[71], [A1]-[A26] and [B1]-[B30].

[1] Use of a compound represented by the formula (7-1):

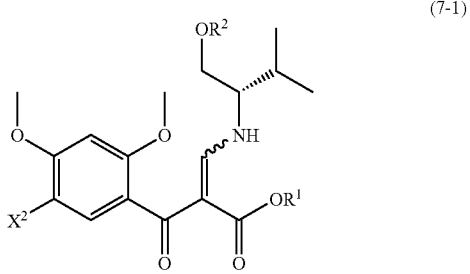

wherein $R^1$ is a $C_1$-$C_4$ alkyl group, $R^2$ is a hydroxyl-protecting group and $X^2$ is a halogen atom (hereinafter sometimes to be abbreviated as compound (7-1)), for the production of compound (10):

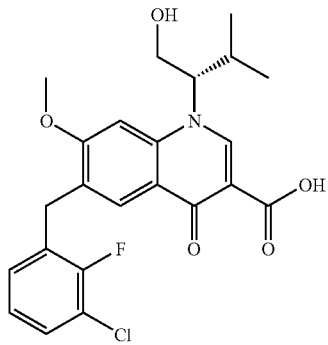
(10)

or a salt thereof.

[2] Use of a compound represented by the formula (6-B):

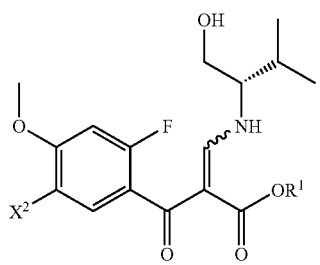
(6-B)

wherein $R^1$ is a $C_1$-$C_4$ alkyl group and $X^2$ is a halogen atom (hereinafter sometimes to be abbreviated as compound (6-B)), for the production of compound (10)

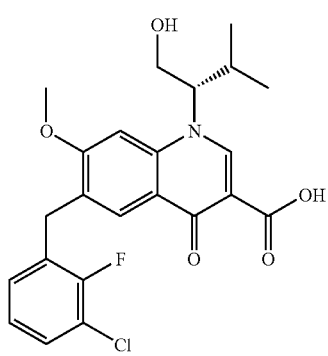
(10)

or a salt thereof.

[3] Use of a compound represented by the formula (8):

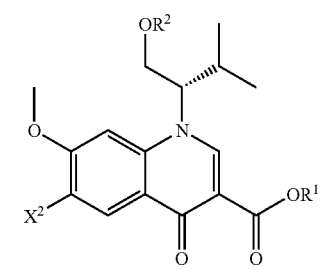
(8)

wherein $R^1$ is a $C_1$-$C_4$ alkyl group, $R^2$ is a hydroxyl-protecting group and $X^2$ is a halogen atom (hereinafter sometimes to be abbreviated as compound (8)), for the production of compound (10):

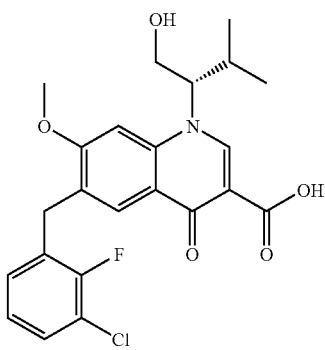
(10)

or a salt thereof.

[4] Use of a compound represented by the formula (8):

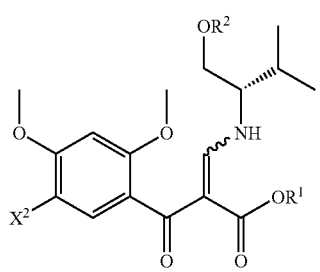
(8)

wherein $R^1$ is a $C_1$-$C_4$ alkyl group, $R^2$ is a hydroxyl-protecting group and $X^2$ is a halogen atom, and a compound represented by the formula (7-1):

(7-1)

wherein $R^1$ is a $C_1$-$C_4$ alkyl group, $R^2$ is a hydroxyl-protecting group and $X^2$ is a halogen atom, for the production of compound (10):

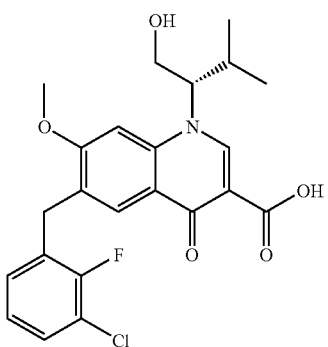
(10)

or a salt thereof.
[5] Use of a compound represented by the formula (8):

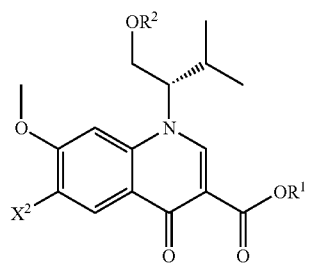
(8)

wherein $R^1$ is a $C_1$-$C_4$ alkyl group, $R^2$ is a hydroxyl-protecting group and $X^2$ is a halogen atom, and a compound represented by the formula (6-B):

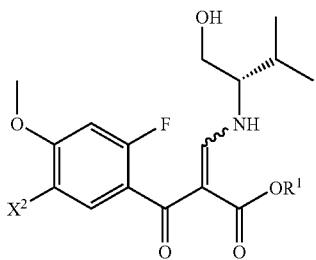
(6-B)

wherein $R^1$ is a $C_1$-$C_4$ alkyl group and $X^2$ is a halogen, for the production of compound (10):

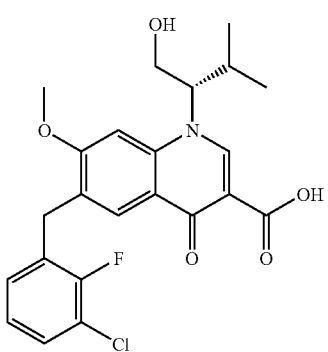
(10)

or a salt thereof.

[6] Use of a compound represented by the formula (9):

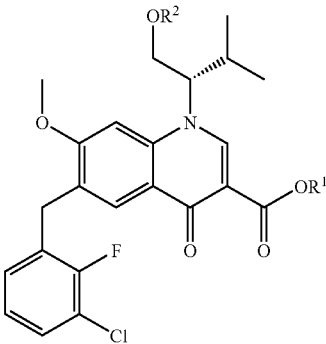
(9)

wherein $R^1$ is a $C_1$-$C_4$ alkyl group and $R^2$ is a hydroxyl-protecting group (hereinafter sometimes to be abbreviated as compound (9)), and a compound represented by the formula (8):

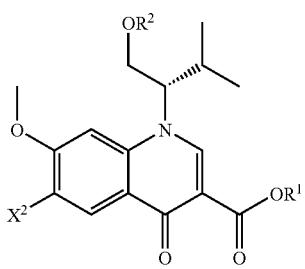
(8)

wherein $R^1$ is a $C_1$-$C_4$ alkyl group, $R^2$ is a hydroxyl-protecting group and $X^2$ is a halogen atom, for the production of compound (10):

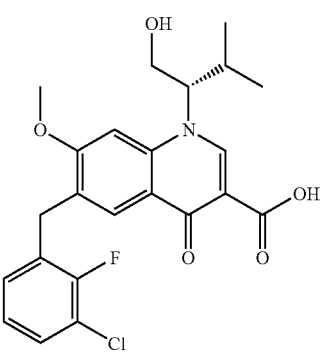
(10)

or a salt thereof.
[7] Use of a compound represented by the formula (9):

(9)

wherein R¹ is a $C_1$-$C_4$ alkyl group and R² is a hydroxyl-protecting group, a compound represented by the formula (8):

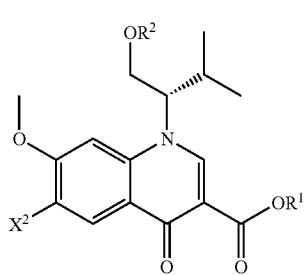
(8)

wherein R¹ is a $C_1$-$C_4$ alkyl group, R² is a hydroxyl-protecting group and X² is a halogen atom, and a compound represented by the formula (7-1):

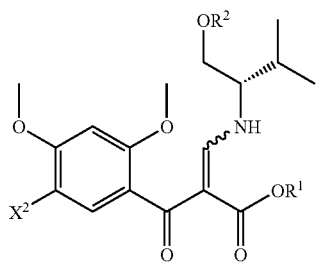
(7-1)

wherein R¹ is a $C_1$-$C_4$ alkyl group, R² is a hydroxyl-protecting group and X² is a halogen atom, for the production of compound (10):

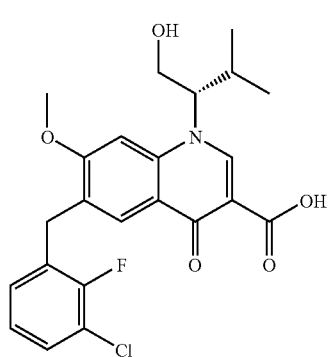
(10)

or a salt thereof.

[8] Use of a compound represented by the formula (9):

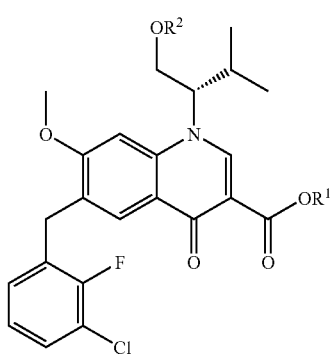
(9)

wherein R¹ is a $C_1$-$C_4$ alkyl group and R² is a hydroxyl-protecting group, a compound represented by the formula (8):

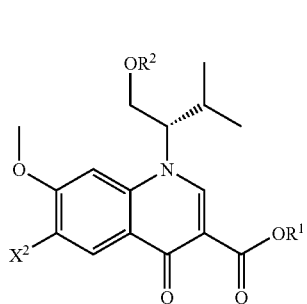
(8)

wherein R¹ is a $C_1$-$C_4$ alkyl group, R² is a hydroxyl-protecting group and X² is a halogen atom, and a compound represented by the formula (6-B):

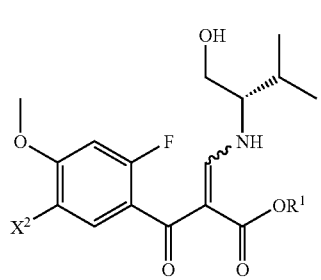
(6-B)

wherein R¹ is a $C_1$-$C_4$ alkyl group and X² is a halogen atom, for the production of compound (10):

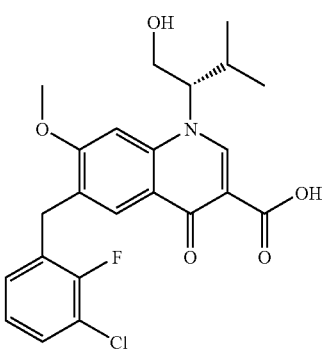
(10)

or a salt thereof.

[9] Use of a compound represented by the formula (8):

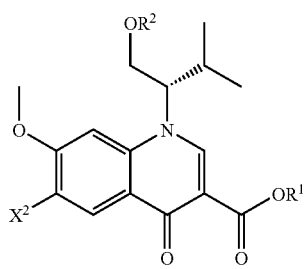
(8)

wherein $R^1$ is a $C_1$-$C_4$ alkyl group, $R^2$ is a hydroxyl-protecting group and $X^2$ is a halogen atom, and a compound represented by the formula (3):

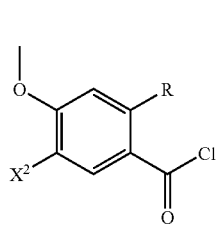

(3)

wherein R is a fluorine atom or a methoxy group and $X^2$ is a halogen atom (hereinafter sometimes to be abbreviated as compound (3)), for the production of compound (10):

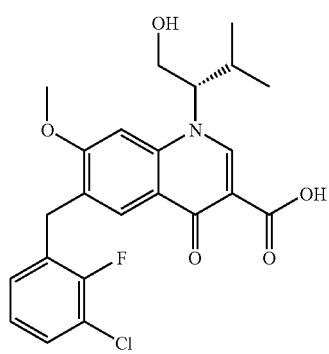

(10)

or a salt thereof.

[10] Use of a compound represented by the formula (8):

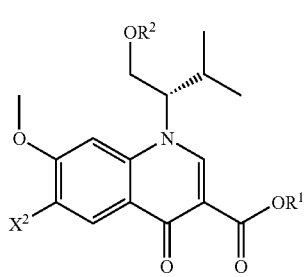

(8)

wherein $R^1$ is a $C_1$-$C_4$ alkyl group, $R^2$ is a hydroxyl-protecting group and $X^2$ is a halogen atom, a compound represented by the formula (7-1):

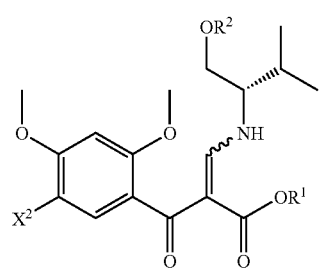

(7-1)

wherein $R^1$ is a $C_1$-$C_4$ alkyl group, $R^2$ is a hydroxyl-protecting group and $X^2$ is a halogen atom, and a compound represented by the formula (3-A):

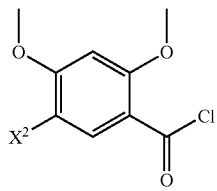

(3-A)

wherein $X^2$ is a halogen atom (hereinafter sometimes to be abbreviated as compound (3-A)), for the production of compound (10):

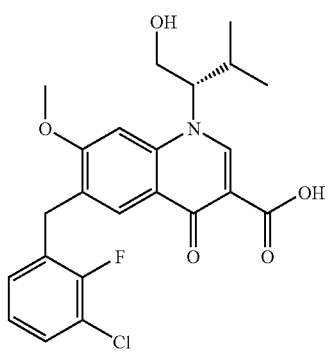

(10)

or a salt thereof.

[11] Use of a compound represented by the formula (8):

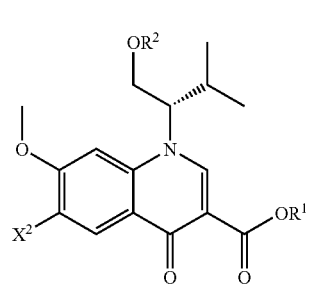

(8)

wherein $R^1$ is a $C_1$-$C_4$ alkyl group, $R^2$ is a hydroxyl-protecting group and $X^2$ is a halogen atom, a compound represented by the formula (6-B):

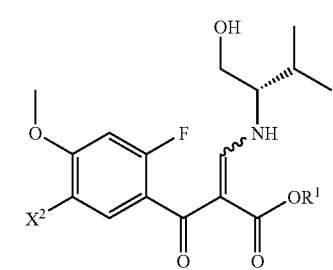

(6-B)

wherein $R^1$ is a $C_1$-$C_4$ alkyl group and $X^2$ is a halogen atom, and a compound represented by the formula (3-B):

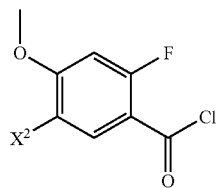

(3-B)

wherein $X^2$ is a halogen atom (hereinafter sometimes to be abbreviated as compound (3-B)), for the production of compound (10):

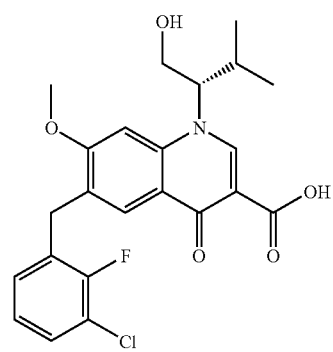

(10)

or a salt thereof.

[12] Use of a compound represented by the formula (8):

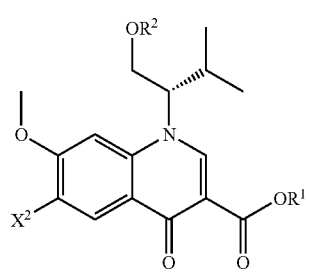

(8)

wherein $R^1$ is a $C_1$-$C_4$ alkyl group, $R^2$ is a hydroxyl-protecting group and $X^2$ is a halogen atom, a compound represented by the formula (4):

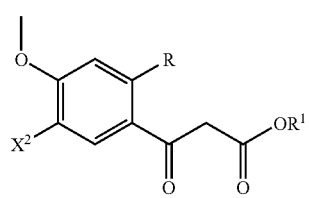

(4)

wherein R is a fluorine atom or a methoxy group, $R^1$ is a $C_1$-$C_4$ alkyl group and $X^2$ is a halogen atom (hereinafter sometimes to be abbreviated as compound (4)), or a salt thereof, and a compound represented by the formula (3):

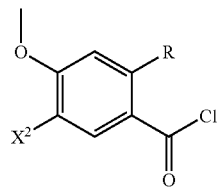

(3)

wherein R is a fluorine atom or a methoxy group and $X^2$ is a halogen atom, for the production of compound (10):

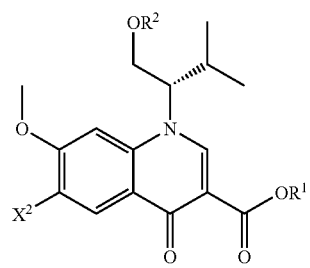

(10)

or a salt thereof.

[13] Use of a compound represented by the formula (8):

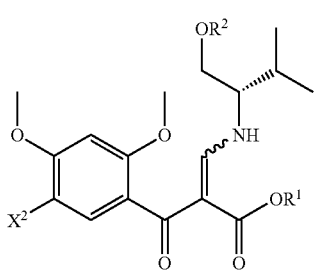

(8)

wherein $R^1$ is a $C_1$-$C_4$ alkyl group, $R^2$ is a hydroxyl-protecting group and $X^2$ is a halogen atom, a compound represented by the formula (7-1):

(7-1)

wherein $R^1$ is a $C_1$-$C_4$ alkyl group, $R^2$ is a hydroxyl-protecting group and $X^2$ is a halogen atom, a compound represented by the formula (4-A):

(4-A)

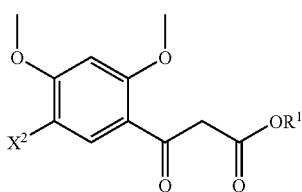

wherein $R^1$ is a $C_1$-$C_4$ alkyl group and $X^2$ is a halogen atom (hereinafter sometimes to be abbreviated as compound (4-A)), or a salt thereof, and a compound represented by the formula (3-A):

(3-A)

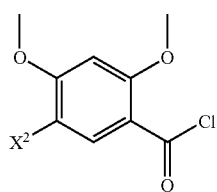

wherein $X^2$ is a halogen atom, for the production of compound (10):

(10)

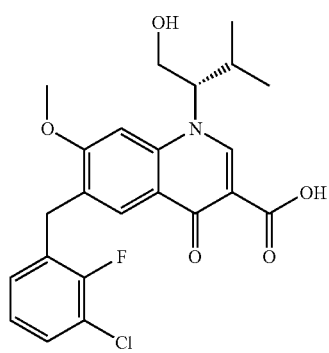

or a salt thereof.

[14] Use of a compound represented by the formula (8):

(8)

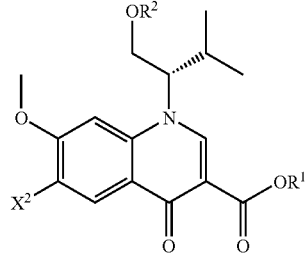

wherein $R^1$ is a $C_1$-$C_4$ alkyl group, $R^2$ is a hydroxyl-protecting group and $X^2$ is a halogen atom, a compound represented by the formula (6-B):

(6-B)

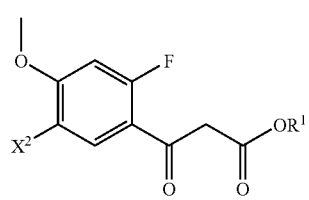

wherein $R^1$ is a $C_1$-$C_4$ alkyl group and $X^2$ is a halogen atom, a compound represented by the formula (4-B):

(4-B)

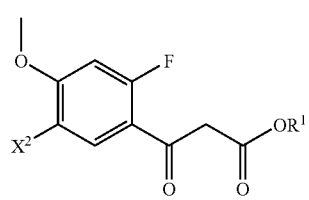

wherein $R^1$ is a $C_1$-$C_4$ alkyl group and $X^2$ is a halogen atom (hereinafter sometimes to be abbreviated as compound (4-B)), or a salt thereof, and a compound represented by the formula (3-B):

(3-B)

wherein $X^2$ is a halogen atom, for the production of compound (10):

(10)

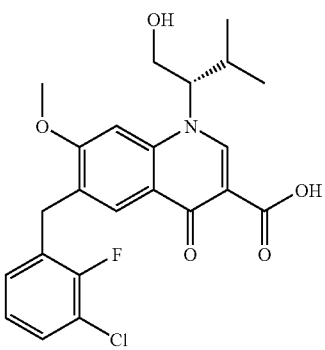

or a salt thereof.

[15] Use of a compound represented by the formula (8):

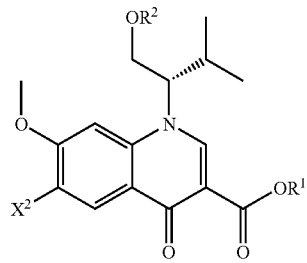
(8)

wherein $R^1$ is a $C_1$-$C_4$ alkyl group, $R^2$ is a hydroxyl-protecting group and $X^2$ is a halogen atom, a compound represented by the formula (5):

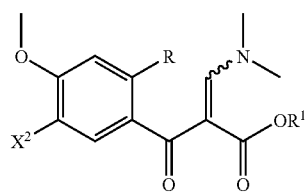
(5)

wherein R is a fluorine atom or a methoxy group, $R^1$ is a $C_1$-$C_4$ alkyl group and $X^2$ is a halogen atom (hereinafter sometimes to be abbreviated as compound (5)), and a compound represented by the formula (3):

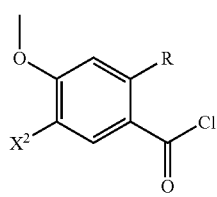
(3)

wherein R is a fluorine atom or a methoxy group and $X^2$ is a halogen atom, for the production of compound (10):

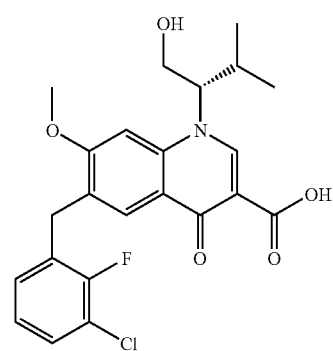
(10)

or a salt thereof.

[16] Use of a compound represented by the formula (8):

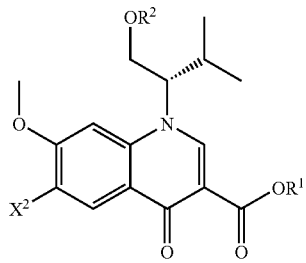
(8)

wherein $R^1$ is a $C_1$-$C_4$ alkyl group, $R^2$ is a hydroxyl-protecting group and $X^2$ is a halogen atom, a compound represented by the formula (7-1):

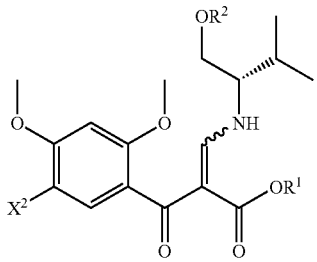
(7-1)

wherein $R^1$ is a $C_1$-$C_4$ alkyl group, $R^2$ is a hydroxyl-protecting group and $X^2$ is a halogen atom, a compound represented by the formula (5-A):

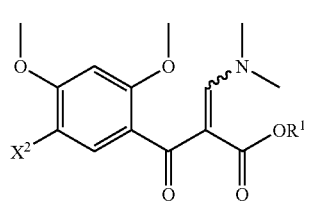
(5-A)

wherein $R^1$ is a $C_1$-$C_4$ alkyl group and $X^2$ is a halogen atom (hereinafter sometimes to be abbreviated as compound (5-A)), and a compound represented by the formula (3-A):

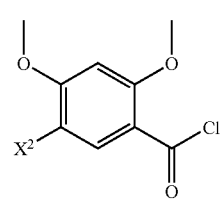
(3-A)

wherein $X^2$ is a halogen atom, for the production of compound (10):

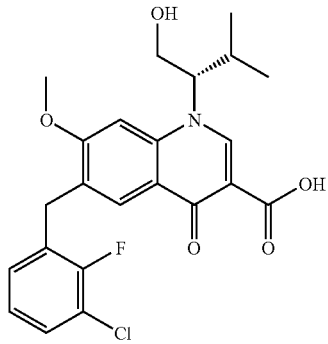
(10)

or a salt thereof.

[17] Use of a compound represented by the formula (8):

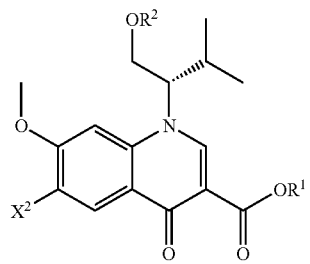
(8)

wherein $R^1$ is a $C_1$-$C_4$ alkyl group, $R^2$ is a hydroxyl-protecting group and $X^2$ is a halogen atom, a compound represented by the formula (6-B):

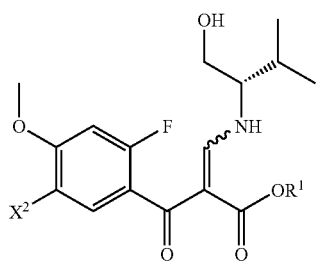
(6-B)

wherein $R^1$ is a $C_1$-$C_4$ alkyl group and $X^2$ is a halogen atom, a compound represented by the formula (5-B):

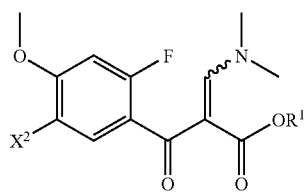
(5-B)

wherein $R^1$ is a $C_1$-$C_4$ alkyl group and $X^2$ is a halogen atom (hereinafter sometimes to be abbreviated as compound (5-B)), and a compound represented by the formula (3-B):

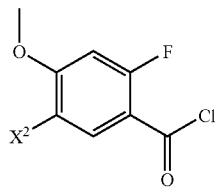
(3-B)

wherein $X^2$ is a halogen atom, for the production of compound (10):

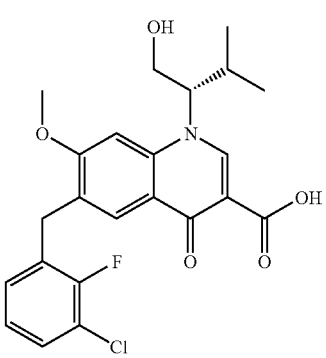
(10)

or a salt thereof.

[18] Use of a compound represented by the formula (9):

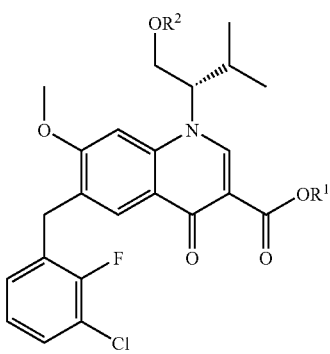
(9)

wherein $R^1$ is a $C_1$-$C_4$ alkyl group and $R^2$ is a hydroxyl-protecting group, a compound represented by the formula (8):

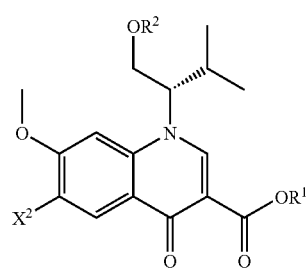
(8)

wherein $R^1$ is a $C_1$-$C_4$ alkyl group, $R^2$ is a hydroxyl-protecting group and $X^2$ is a halogen atom, a compound represented by the formula (6):

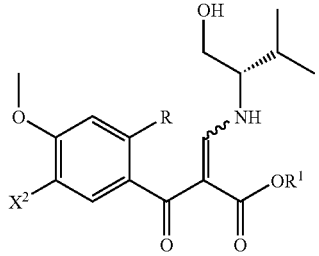
(6)

wherein R is a fluorine atom or a methoxy group, $R^1$ is a $C_1$-$C_4$ alkyl group and $X^2$ is a halogen atom (hereinafter sometimes to be abbreviated as compound (6)), a compound represented by the formula (5):

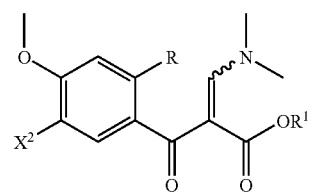
(5)

wherein R is a fluorine atom or a methoxy group, $R^1$ is a $C_1$-$C_4$ alkyl group and $X^2$ is a halogen atom, a compound represented by the formula (4):

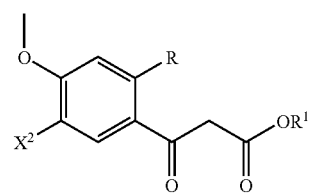
(4)

wherein R is a fluorine atom or a methoxy group, $R^1$ is a $C_1$-$C_4$ alkyl group and $X^2$ is a halogen atom, or a salt thereof, and a compound represented by the formula (3):

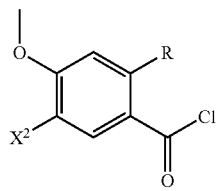
(3)

wherein R is a fluorine atom or a methoxy group and $X^2$ is a halogen atom, for the production of compound (10):

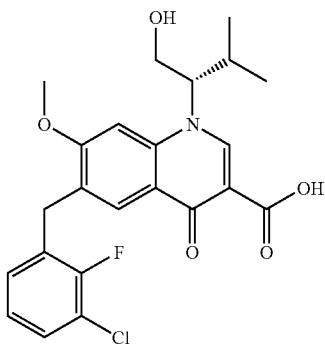
(10)

or a salt thereof.

[19] Use of a compound represented by the formula (9):

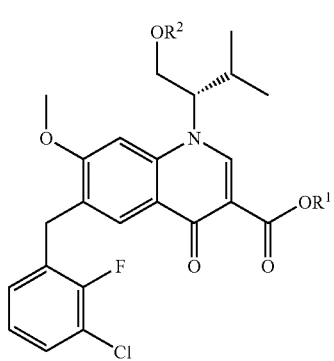
(9)

wherein $R^1$ is a $C_1$-$C_4$ alkyl group and $R^2$ is a hydroxyl-protecting group, a compound represented by the formula (8):

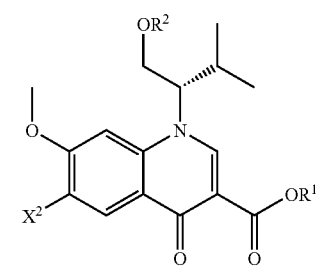
(8)

wherein $R^1$ is a $C_1$-$C_4$ alkyl group, $R^2$ is a hydroxyl-protecting group and $X^2$ is a halogen atom, a compound represented by the formula (7-1):

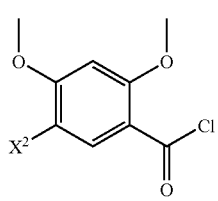
(3-A)

wherein $X^2$ is a halogen atom, for the production of compound (10):

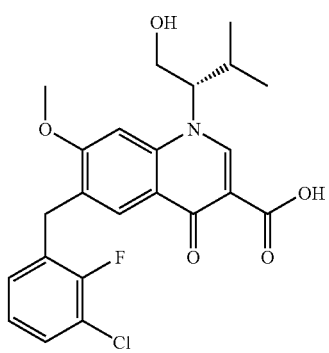
(10)

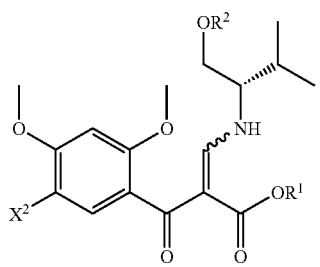
(7-1)

wherein $R^1$ is a $C_1$-$C_4$ alkyl group, $R^2$ is a hydroxyl-protecting group and $X^2$ is a halogen atom, a compound represented by the formula (6-A):

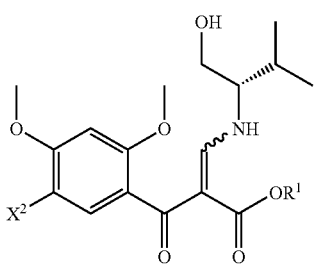
(6-A)

wherein $R^1$ is a $C_1$-$C_4$ alkyl group and $X^2$ is a halogen atom (hereinafter sometimes to be abbreviated as compound (6-A)), a compound represented by the formula (5-A):

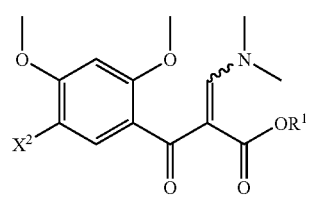
(5-A)

wherein $R^1$ is a $C_1$-$C_4$ alkyl group and $X^2$ is a halogen atom, a compound represented by the formula (4-A):

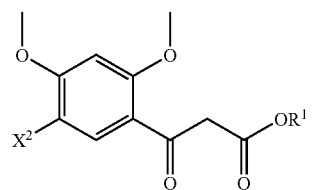
(4-A)

wherein $R^1$ is a $C_1$-$C_4$ alkyl group and $X^2$ is a halogen atom, or a salt thereof, and a compound represented by the formula (3-A):

or a salt thereof.

[20] Use of a compound represented by the formula (9):

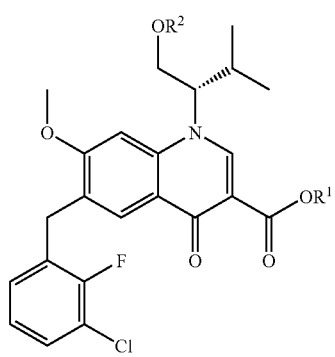
(9)

wherein $R^1$ is a $C_1$-$C_4$ alkyl group and $R^2$ is a hydroxyl-protecting group, a compound represented by the formula (8):

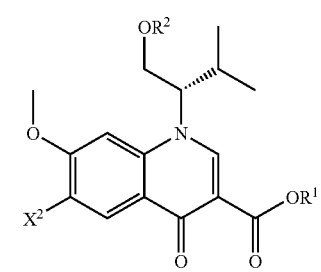
(8)

wherein $R^1$ is a $C_1$-$C_4$ alkyl group, $R^2$ is a hydroxyl-protecting group and $X^2$ is a halogen atom, a compound represented by the formula (7-2):

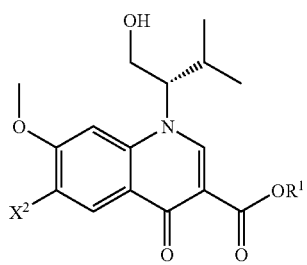
(7-2)

wherein $R^1$ is a $C_1$-$C_4$ alkyl group and $X^2$ is a halogen atom (hereinafter sometimes to be abbreviated as compound (7-2)), a compound represented by the formula (6-B):

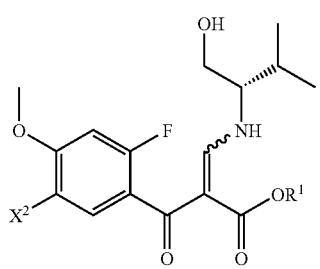
(6-B)

wherein $R^1$ is a $C_1$-$C_4$ alkyl group and $X^2$ is a halogen atom, a compound represented by the formula (5-B):

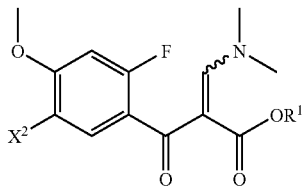
(5-B)

wherein $R^1$ is a $C_1$-$C_4$ alkyl group and $X^2$ is a halogen atom, a compound represented by the formula (4-B):

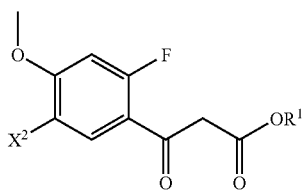
(4-B)

wherein $R^1$ is a $C_1$-$C_4$ alkyl group and $X^2$ is a halogen atom, or a salt thereof, and a compound represented by the formula (3-B):

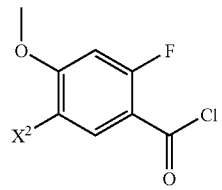
(3-B)

wherein $X^2$ is a halogen atom, for the production of compound (10):

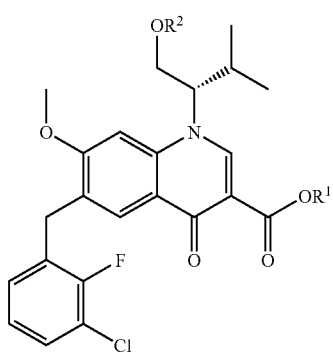
(10)

or a salt thereof.

[21] Use of a compound represented by the formula (9):

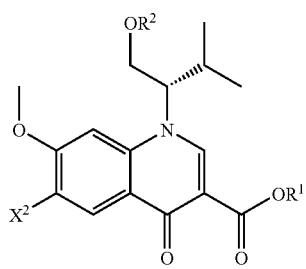
(9)

wherein $R^1$ is a $C_1$-$C_4$ alkyl group and $R^2$ is a hydroxyl-protecting group, a compound represented by the formula (8):

(8)

wherein $R^1$ is a $C_1$-$C_4$ alkyl group, $R^2$ is a hydroxyl-protecting group and $X^2$ is a halogen atom, a compound represented by the formula (6):

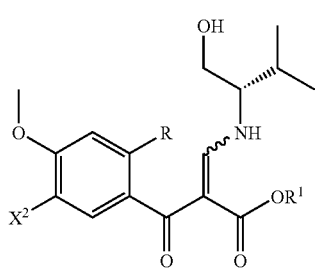
(6)

wherein R is a fluorine atom or a methoxy group, $R^1$ is a $C_1$-$C_4$ alkyl group and $X^2$ is a halogen atom, a compound represented by the formula (5):

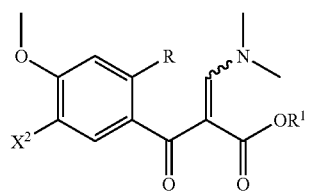
(5)

wherein R is a fluorine atom or a methoxy group, $R^1$ is a $C_1$-$C_4$ alkyl group and $X^2$ is a halogen atom, a compound represented by the formula (4):

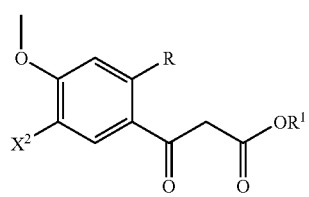
(4)

wherein R is a fluorine atom or a methoxy group, $R^1$ is a $C_1$-$C_4$ alkyl group and $X^2$ is a halogen atom, or a salt thereof, and a compound represented by the formula (3):

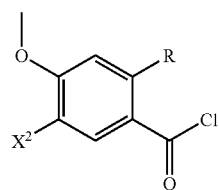
(3)

wherein R is a fluorine atom or a methoxy group and $X^2$ is a halogen atom, a compound represented by the formula (2):

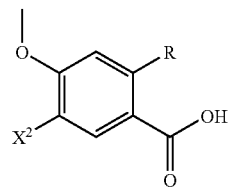
(2)

wherein R is a fluorine atom or a methoxy group and $X^2$ is a halogen atom (hereinafter to be sometimes abbreviated as compound (2)), or a salt thereof, and a compound represented by the formula (1):

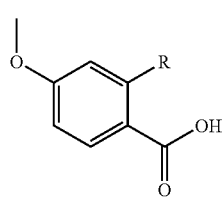
(1)

wherein R is a fluorine atom or a methoxy group (hereinafter sometimes to be abbreviated as compound (1)), or a salt thereof, for the production of compound (10):

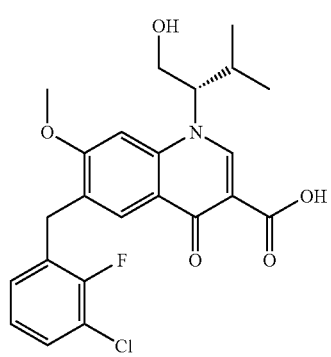
(10)

or a salt thereof.

[22] Use of a compound represented by the formula (9):

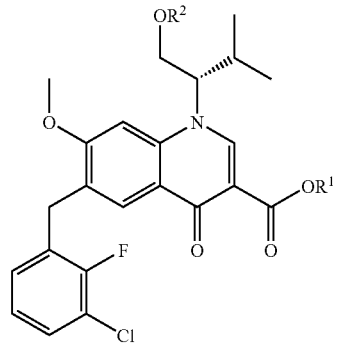
(9)

wherein $R^1$ is a $C_1$-$C_4$ alkyl group and $R^2$ is a hydroxyl-protecting group, a compound represented by the formula (8):

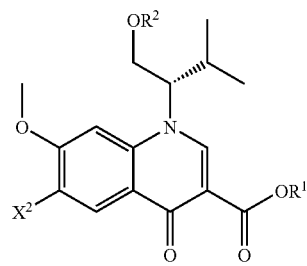
(8)

wherein $R^1$ is a $C_1$-$C_4$ alkyl group, $R^2$ is a hydroxyl-protecting group and $X^2$ is a halogen atom, a compound represented by the formula (7-1):

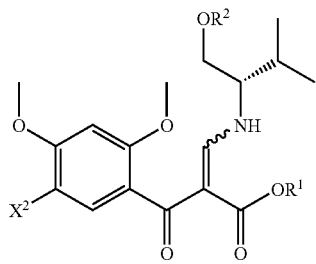

(7-1)

wherein $R^1$ is a $C_1$-$C_4$ alkyl group, $R^2$ is a hydroxyl-protecting group and $X^2$ is a halogen atom, a compound represented by the formula (6-A):

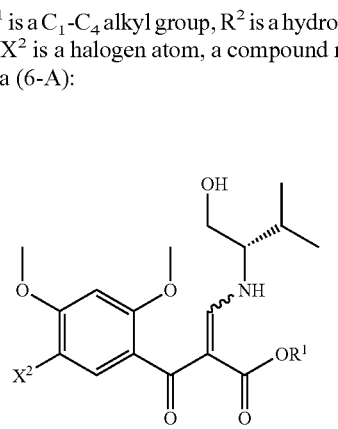

(6-A)

wherein $R^1$ is a $C_1$-$C_4$ alkyl group and $X^2$ is a halogen atom, a compound represented by the formula (5-A):

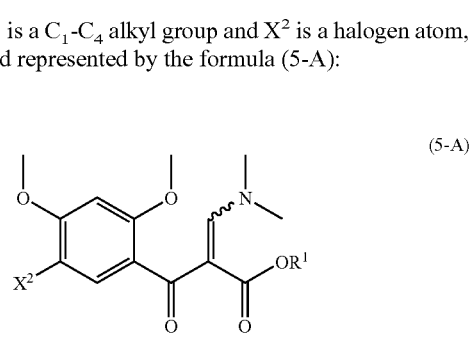

(5-A)

wherein $R^1$ is a $C_1$-$C_4$ alkyl group and $X^2$ is a halogen atom, a compound represented by the formula (4-A):

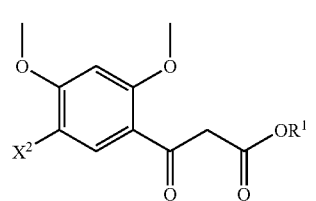

(4-A)

wherein $R^1$ is a $C_1$-$C_4$ alkyl group and $X^2$ is a halogen atom, or a salt thereof, and a compound represented by the formula (3-A):

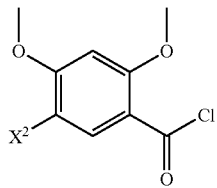

(3-A)

wherein $X^2$ is a halogen atom, a compound represented by the formula (2-A):

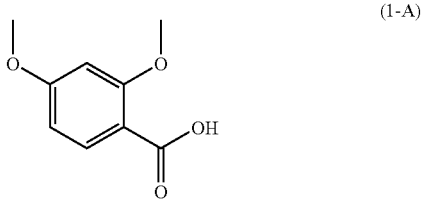

(2-A)

wherein $X^2$ is a halogen atom (hereinafter sometimes to be abbreviated as compound (2-A)), or a salt thereof, and compound (1-A):

(1-A)

or a salt thereof, for the production of compound (10):

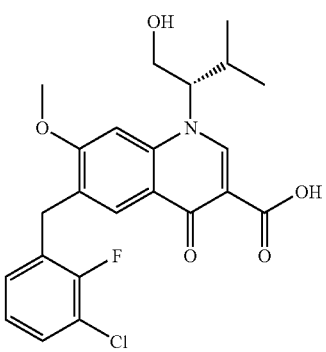

(10)

or a salt thereof.

[23] Use of a compound represented by the formula (9):

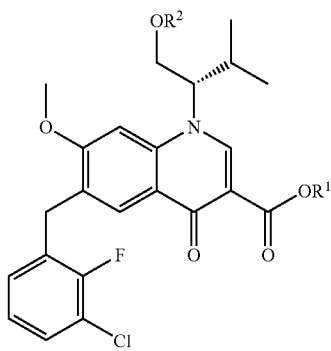
(9)

wherein $R^1$ is a $C_1$-$C_4$ alkyl group and $R^2$ is a hydroxyl-protecting group, a compound represented by the formula (8):

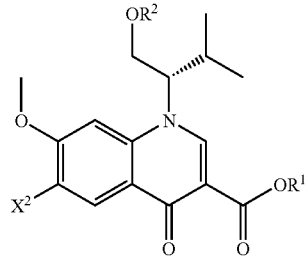
(8)

wherein $R^1$ is a $C_1$-$C_4$ alkyl group, $R^2$ is a hydroxyl-protecting group and $X^2$ is a halogen atom, a compound represented by the formula (7-2):

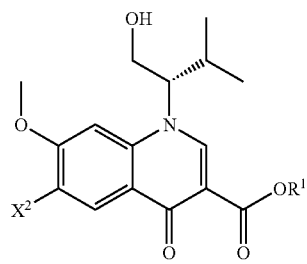
(7-2)

wherein $R^1$ is a $C_1$-$C_4$ alkyl group and $X^2$ is a halogen atom, a compound represented by the formula (6-B):

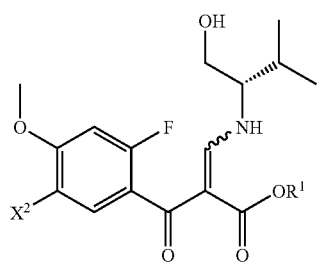
(6-B)

wherein $R^1$ is a $C_1$-$C_4$ alkyl group and $X^2$ is a halogen atom, a compound represented by the formula (5-B):

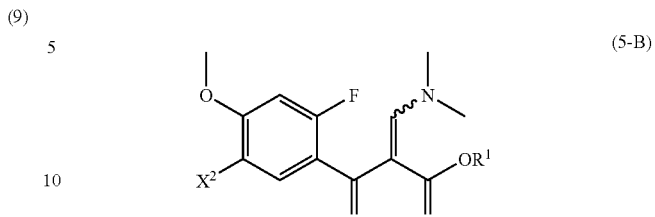
(5-B)

wherein $R^1$ is a $C_1$-$C_4$ alkyl group and $X^2$ is a halogen atom, a compound represented by the formula (4-B):

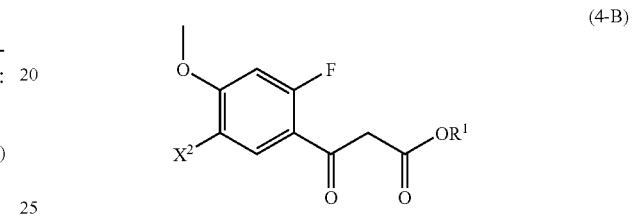
(4-B)

wherein $R^1$ is a $C_1$-$C_4$ alkyl group and $X^2$ is a halogen atom, or a salt thereof, a compound represented by the formula (3-B):

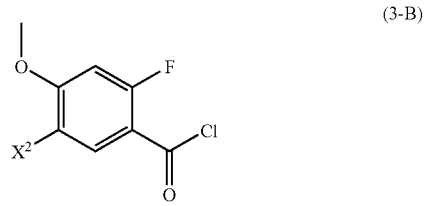
(3-B)

wherein $X^2$ is a halogen atom, a compound represented by the formula (2-B):

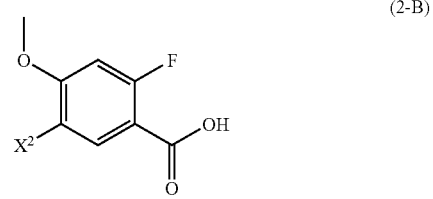
(2-B)

wherein $X^2$ is a halogen atom (hereinafter sometimes to be abbreviated as compound (2-B)), or a salt thereof, and compound (1-B):

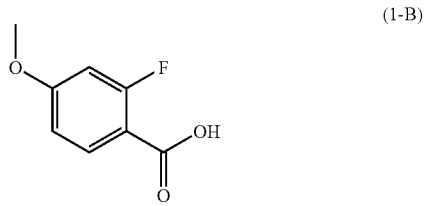
(1-B)

or a salt thereof, for the production of compound (10):

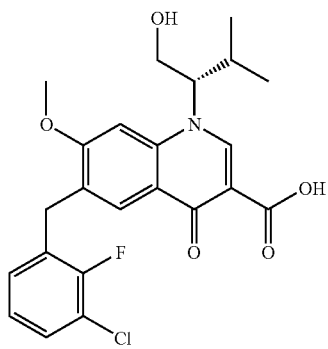

(10)

or a salt thereof.

[24] Use of a compound represented by the formula (7-1):

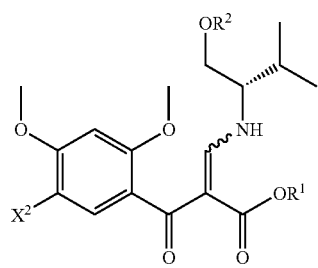

(7-1)

wherein $R^1$ is a $C_1$-$C_4$ alkyl group, $R^2$ is a hydroxyl-protecting group and $X^2$ is a halogen atom, for the production of a compound represented by the formula (8):

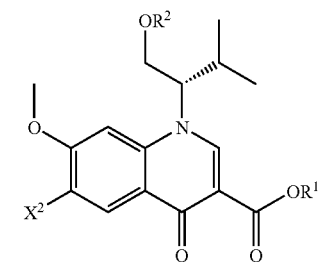

(8)

wherein $R^1$ is a $C_1$-$C_4$ alkyl group, $R^2$ is a hydroxyl-protecting group and $X^2$ is a halogen atom.

[25] Use of a compound represented by the formula (6-B):

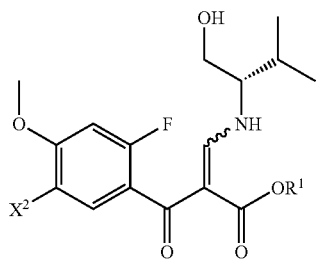

(6-B)

wherein $R^1$ is a $C_1$-$C_4$ alkyl group and $X^2$ is a halogen atom, for the production of a compound represented by the formula (8):

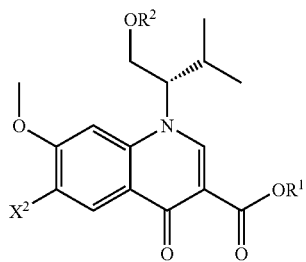

(8)

wherein $R^1$ is a $C_1$-$C_4$ alkyl group, $R^2$ is a hydroxyl-protecting group and $X^2$ is a halogen atom.

[26] Use of a compound represented by the formula (3):

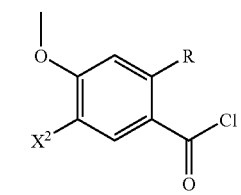

(3)

wherein R is a fluorine atom or a methoxy group and $X^2$ is a halogen atom, for the production of a compound represented by the formula (8):

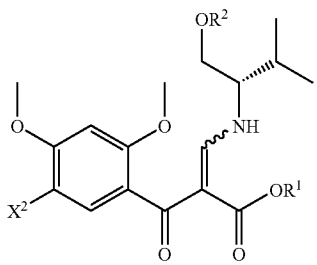

(8)

wherein $R^1$ is a $C_1$-$C_4$ alkyl group, $R^2$ is a hydroxyl-protecting group and $X^2$ is a halogen atom.

[27] Use of a compound represented by the formula (7-1):

(7-1)

wherein $R^1$ is a $C_1$-$C_4$ alkyl group, $R^2$ is a hydroxyl-protecting group and $X^2$ is a halogen atom, and a compound represented by the formula (3-A):

(3-A)

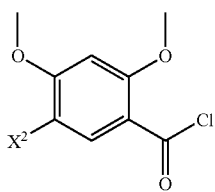

wherein $X^2$ is a halogen atom, for the production of a compound represented by the formula (8):

(8)

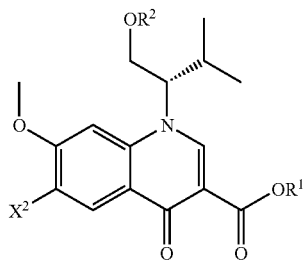

wherein $R^1$ is a $C_1$-$C_4$ alkyl group, $R^2$ is a hydroxyl-protecting group and $X^2$ is a halogen atom.

[28] Use of a compound represented by the formula (6-B):

(6-B)

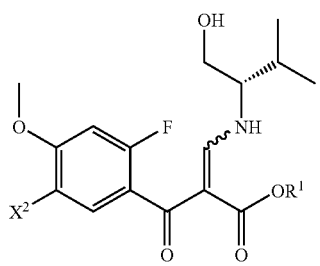

wherein $R^1$ is a $C_1$-$C_4$ alkyl group and $X^2$ is a halogen atom, and a compound represented by the formula (3-B):

(3-B)

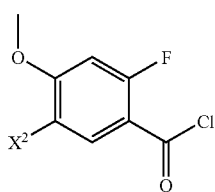

wherein $X^2$ is a halogen atom, for the production of a compound represented by the formula (8):

(8)

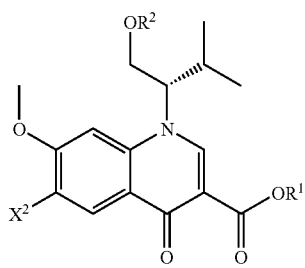

wherein $R^1$ is a $C_1$-$C_4$ alkyl group, $R^2$ is a hydroxyl-protecting group and $X^2$ is a halogen atom.

[29] Use of a compound represented by the formula (3):

(3)

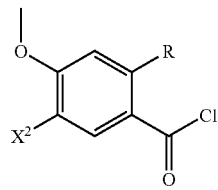

wherein R is a fluorine atom or a methoxy group and $X^2$ is a halogen atom, and a compound represented by the formula (4):

(4)

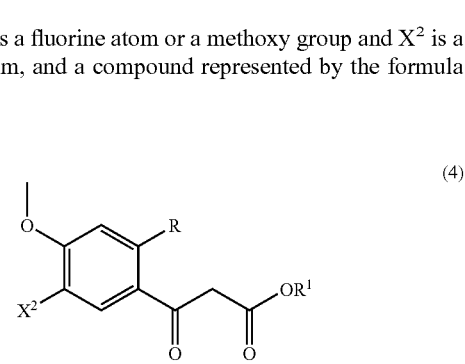

wherein R is a fluorine atom or a methoxy group, $R^1$ is a $C_1$-$C_4$ alkyl group and $X^2$ is a halogen atom, or a salt thereof, for the production of a compound represented by the formula (8):

(8)

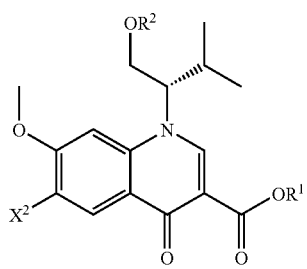

wherein $R^1$ is a $C_1$-$C_4$ alkyl group, $R^2$ is a hydroxyl-protecting group and $X^2$ is a halogen atom.

[30] Use of a compound represented by the formula (7-1):

(7-1)

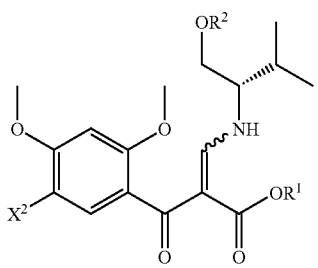

wherein $R^1$ is a $C_1$-$C_4$ alkyl group, $R^2$ is a hydroxyl-protecting group and $X^2$ is a halogen atom, a compound represented by the formula (4-A):

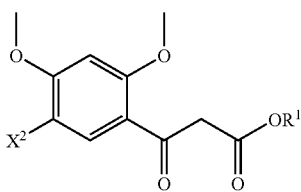
(4-A)

wherein $R^1$ is a $C_1$-$C_4$ alkyl group and $X^2$ is a halogen atom, or a salt thereof, and a compound represented by the formula (3-A):

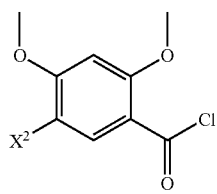
(3-A)

wherein $X^2$ is a halogen atom, for the production of a compound represented by the formula (8):

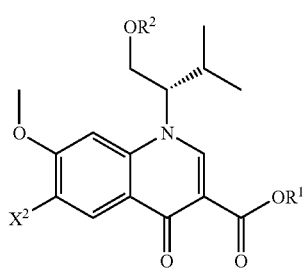
(8)

wherein $R^1$ is a $C_1$-$C_4$ alkyl group, $R^2$ is a hydroxyl-protecting group and $X^2$ is a halogen atom.

[31] Use of a compound represented by the formula (6-B):

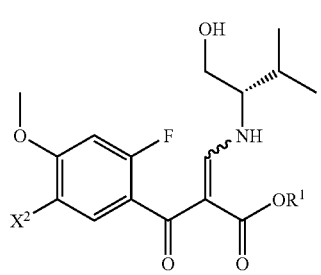
(6-B)

wherein $R^1$ is a $C_1$-$C_4$ alkyl group and $X^2$ is a halogen atom, a compound represented by the formula (4-B):

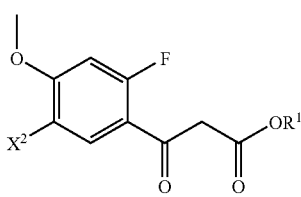
(4-B)

wherein $R^1$ is a $C_1$-$C_4$ alkyl group and $X^2$ is a halogen atom, or a salt thereof, and a compound represented by the formula (3-B):

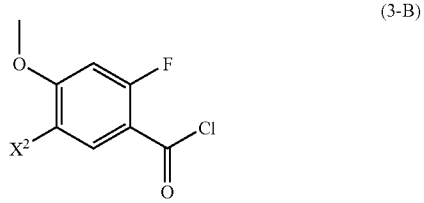
(3-B)

wherein $X^2$ is a halogen atom, for the production of a compound represented by the formula (8):

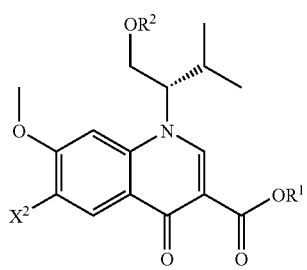
(8)

wherein $R^1$ is a $C_1$-$C_4$ alkyl group, $R^2$ is a hydroxyl-protecting group and $X^2$ is a halogen atom.

[32] Use of a compound represented by the formula (5):

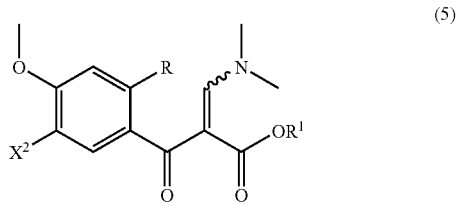
(5)

wherein R is a fluorine atom or a methoxy group, $R^1$ is a $C_1$-$C_4$ alkyl group and $X^2$ is a halogen atom, and a compound represented by the formula (3):

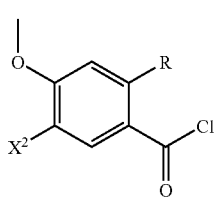
(3)

wherein R is a fluorine atom or a methoxy group and $X^2$ is a halogen atom, for the production of a compound represented by the formula (8):

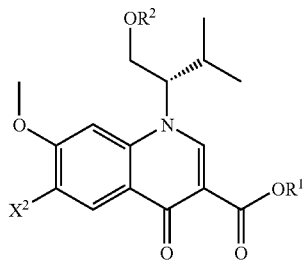

(8)

wherein $R^1$ is a $C_1$-$C_4$ alkyl group, $R^2$ is a hydroxyl-protecting group and $X^2$ is a halogen atom.

[33] Use of a compound represented by the formula (7-1):

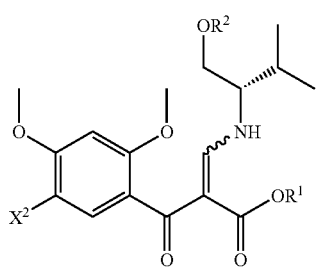

(7-1)

wherein $R^1$ is a $C_1$-$C_4$ alkyl group, $R^2$ is a hydroxyl-protecting group and $X^2$ is a halogen atom, a compound represented by the formula (5-A):

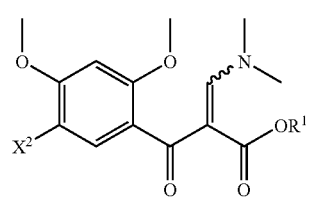

(5-A)

wherein $R^1$ is a $C_1$-$C_4$ alkyl group and $X^2$ is a halogen atom, and a compound represented by the formula (3-A):

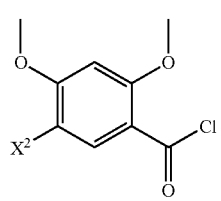

(3-A)

wherein $X^2$ is a halogen atom, for the production of a compound represented by the formula (8):

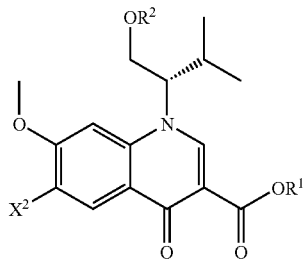

(8)

wherein $R^1$ is a $C_1$-$C_4$ alkyl group, $R^2$ is a hydroxyl-protecting group and $X^2$ is a halogen atom.

[34] Use of a compound represented by the formula (6-B):

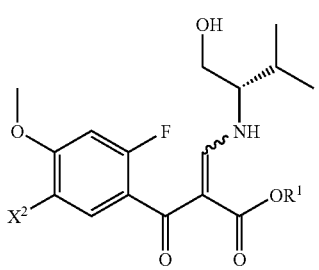

(6-B)

wherein $R^1$ is a $C_1$-$C_4$ alkyl group and $X^2$ is a halogen atom, a compound represented by the formula (5-B):

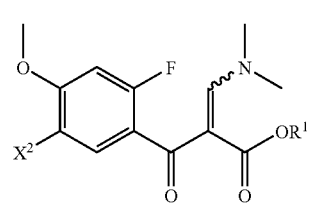

(5-B)

wherein $R^1$ is a $C_1$-$C_4$ alkyl group and $X^2$ is a halogen atom, and a compound represented by the formula (3-B):

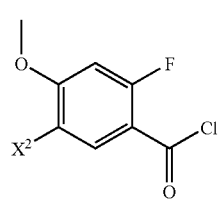

(3-B)

wherein $X^2$ is a halogen atom, for the production of a compound represented by the formula (8):

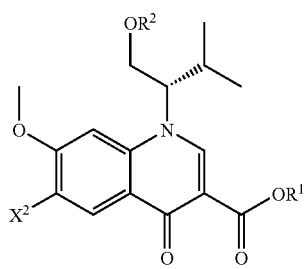

(8)

wherein $R^1$ is a $C_1$-$C_4$ alkyl group, $R^2$ is a hydroxyl-protecting group and $X^2$ is a halogen atom.

[35] Use of a compound represented by the formula (6):

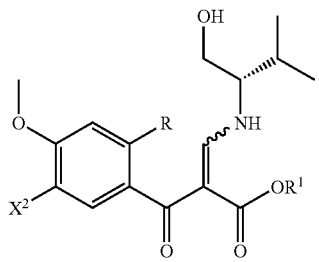
(6)

wherein R is a fluorine atom or a methoxy group, $R^1$ is a $C_1$-$C_4$ alkyl group and $X^2$ is a halogen atom, a compound represented by the formula (5):

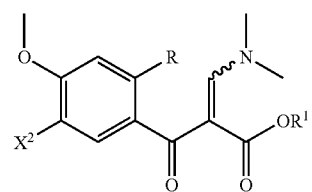
(5)

wherein R is a fluorine atom or a methoxy group, $R^1$ is a $C_1$-$C_4$ alkyl group and $X^2$ is a halogen atom, a compound represented by the formula (4):

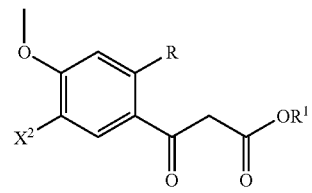
(4)

wherein R is a fluorine atom or a methoxy group, $R^1$ is a $C_1$-$C_4$ alkyl group and $X^2$ is a halogen atom, or a salt thereof, and a compound represented by the formula (3):

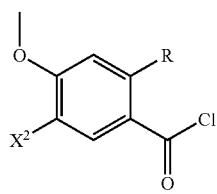
(3)

wherein R is a fluorine atom or a methoxy group and $X^2$ is a halogen atom, for the production of a compound represented by the formula (8):

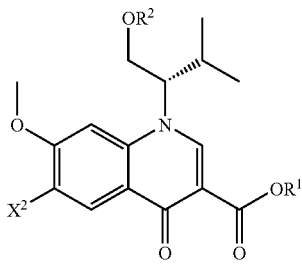
(8)

wherein $R^1$ is a $C_1$-$C_4$ alkyl group, $R^2$ is a hydroxyl-protecting group and $X^2$ is a halogen atom.

[36] Use of a compound represented by the formula (7-1):

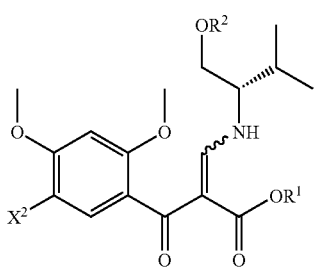
(7-1)

wherein $R^1$ is a $C_1$-$C_4$ alkyl group, $R^2$ is a hydroxyl-protecting group and $X^2$ is a halogen atom, a compound represented by the formula (6-A):

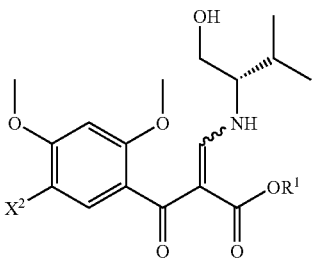
(6-A)

wherein $R^1$ is a $C_1$-$C_4$ alkyl group and $X^2$ is a halogen atom, a compound represented by the formula (5-A):

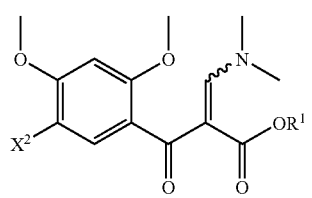
(5-A)

wherein $R^1$ is a $C_1$-$C_4$ alkyl group and $X^2$ is a halogen atom, a compound represented by the formula (4-A):

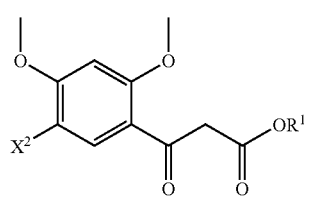
(4-A)

wherein $R^1$ is a $C_1$-$C_4$ alkyl group and $X^2$ is a halogen atom, or a salt thereof, and a compound represented by the formula (3-A):

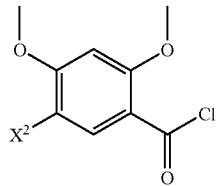

(3-A)

wherein $X^2$ is a halogen atom, for the production of a compound represented by the formula (8):

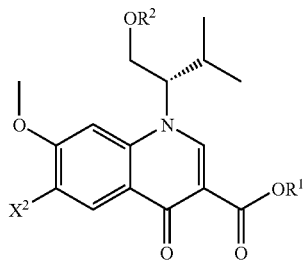

(8)

wherein $R^1$ is a $C_1$-$C_4$ alkyl group, $R^2$ is a hydroxyl-protecting group and $X^2$ is a halogen atom.

[37] Use of a compound represented by the formula (7-2):

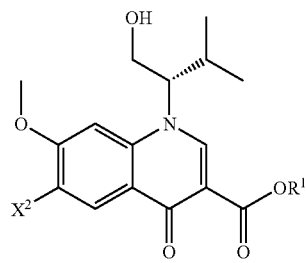

(7-2)

wherein $R^1$ is a $C_1$-$C_4$ alkyl group and $X^2$ is a halogen atom, a compound represented by the formula (6-B):

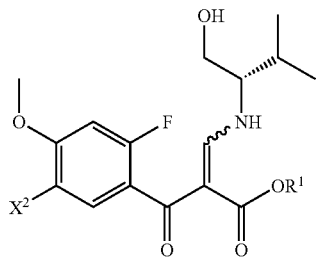

(6-B)

wherein $R^1$ is a $C_1$-$C_4$ alkyl group and $X^2$ is a halogen atom, a compound represented by the formula (5-B):

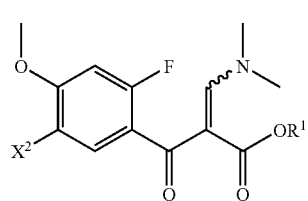

(5-B)

wherein $R^1$ is a $C_1$-$C_4$ alkyl group and $X^2$ is a halogen atom, a compound represented by the formula (4-B):

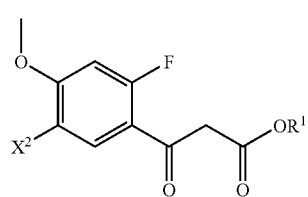

(4-B)

wherein $R^1$ is a $C_1$-$C_4$ alkyl group and $X^2$ is a halogen atom, or a salt thereof, and a compound represented by the formula (3-B):

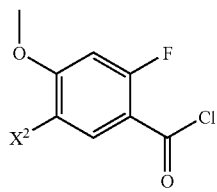

(3-B)

wherein $X^2$ is a halogen atom, for the production of a compound represented by the formula (8):

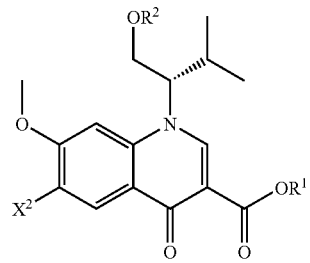

(8)

wherein $R^1$ is a $C_1$-$C_4$ alkyl group, $R^2$ is a hydroxyl-protecting group and $X^2$ is a halogen atom.

[38] Use of a compound represented by the formula (6):

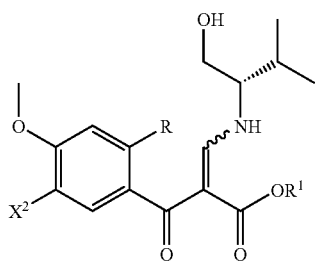
(6)

wherein R is a fluorine atom or a methoxy group, $R^1$ is a $C_1$-$C_4$ alkyl group and $X^2$ is a halogen atom, a compound represented by the formula (5):

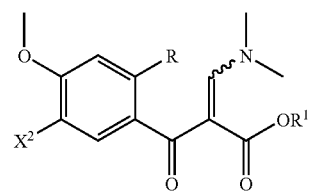
(5)

wherein R is a fluorine atom or a methoxy group, $R^1$ is a $C_1$-$C_4$ alkyl group and $X^2$ is a halogen atom, a compound represented by the formula (4):

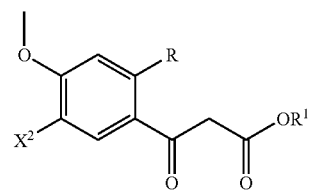
(4)

wherein R is a fluorine atom or a methoxy group, $R^1$ is a $C_1$-$C_4$ alkyl group and $X^2$ is a halogen atom, or a salt thereof, a compound represented by the formula (3):

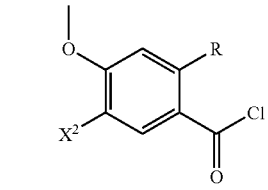
(3)

wherein R is a fluorine atom or a methoxy group and $X^2$ is a halogen atom, a compound represented by the formula (2):

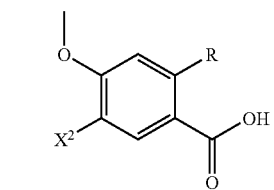
(2)

wherein R is a fluorine atom or a methoxy group and $X^2$ is a halogen atom, or a salt thereof, and a compound represented by the formula (1):

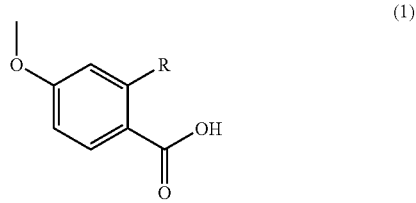
(1)

wherein R is a fluorine atom or a methoxy group, or a salt thereof, for the production of a compound represented by the formula (8):

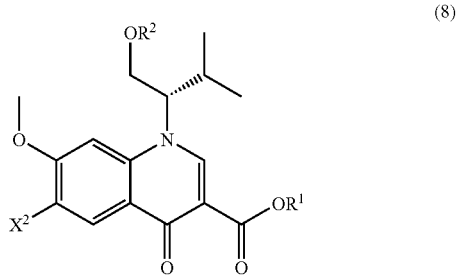
(8)

wherein $R^1$ is a $C_1$-$C_4$ alkyl group, $R^2$ is a hydroxyl-protecting group and $X^2$ is a halogen atom.

[39] Use of a compound represented by the formula (7-1):

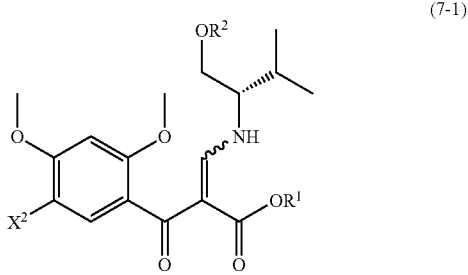
(7-1)

wherein $R^1$ is a $C_1$-$C_4$ alkyl group, $R^2$ is a hydroxyl-protecting group and $X^2$ is a halogen atom, a compound represented by the formula (6-A):

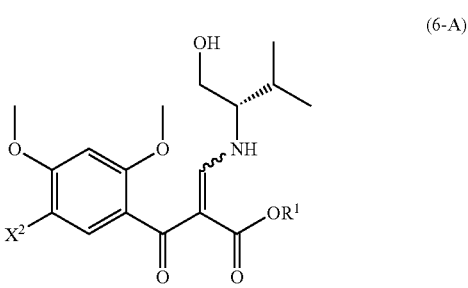
(6-A)

wherein $R^1$ is a $C_1$-$C_4$ alkyl group and $X^2$ is a halogen atom, a compound represented by the formula (5-A):

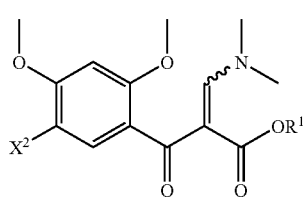
(5-A)

wherein $R^1$ is a $C_1$-$C_4$ alkyl group and $X^2$ is a halogen atom, a compound represented by the formula (4-A):

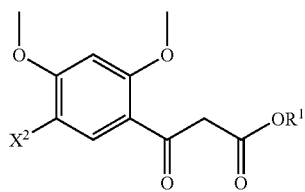
(4-A)

wherein $R^1$ is a $C_1$-$C_4$ alkyl group and $X^2$ is a halogen atom, or a salt thereof, a compound represented by the formula (3-A):

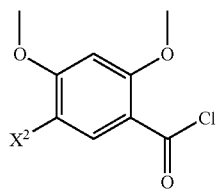
(3-A)

wherein $X^2$ is a halogen atom, a compound represented by the formula (2-A):

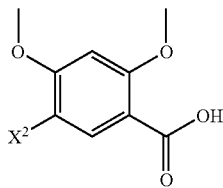
(2-A)

wherein $X^2$ is a halogen atom, or a salt thereof, and compound (1-A):

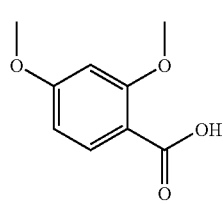
(1-A)

or a salt thereof, for the production of a compound represented by the formula (8):

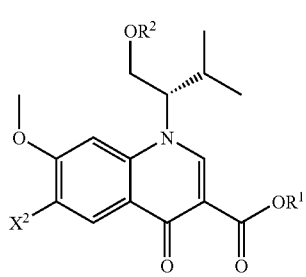
(8)

wherein $R^1$ is a $C_1$-$C_4$ alkyl group, $R^2$ is a hydroxyl-protecting group and $X^2$ is a halogen atom.

[40] Use of a compound represented by the formula (7-2):

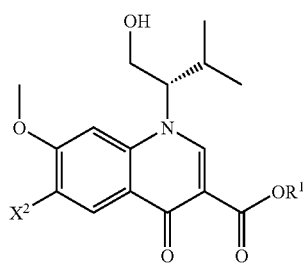
(7-2)

wherein $R^1$ is a $C_1$-$C_4$ alkyl group and $X^2$ is a halogen atom, a compound represented by the formula (6-B):

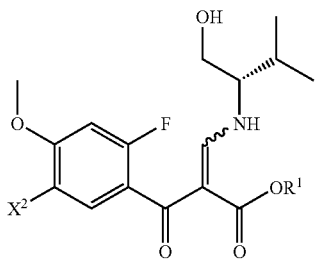
(6-B)

wherein $R^1$ is a $C_1$-$C_4$ alkyl group and $X^2$ is a halogen atom, a compound represented by the formula (5-B):

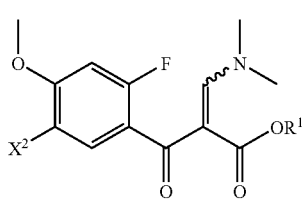
(5-B)

wherein $R^1$ is a $C_1$-$C_4$ alkyl group and $X^2$ is a halogen atom, a compound represented by the formula (4-B):

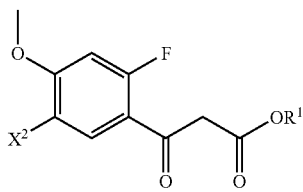
(4-B)

wherein $R^1$ is a $C_1$-$C_4$ alkyl group and $X^2$ is a halogen atom, or a salt thereof, a compound represented by the formula (3-B):

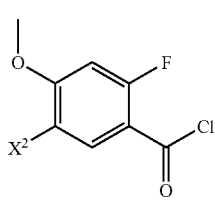
(3-B)

wherein $X^2$ is a halogen atom, a compound represented by the formula (2-B):

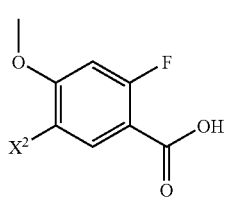
(2-B)

wherein $X^2$ is a halogen atom, or a salt thereof, and compound (1-B):

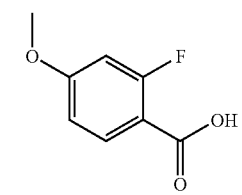
(1-B)

or a salt thereof, for the production of a compound represented by the formula (8):

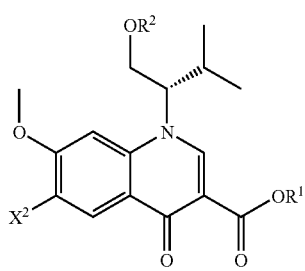
(8)

wherein $R^1$ is a $C_1$-$C_4$ alkyl group, $R^2$ is a hydroxyl-protecting group and $X^2$ is a halogen atom.

[41] Use of a compound represented by the formula (3-B):

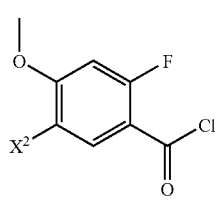
(3-B)

wherein $X^2$ is a halogen atom, for the production of a compound represented by the formula (7-2):

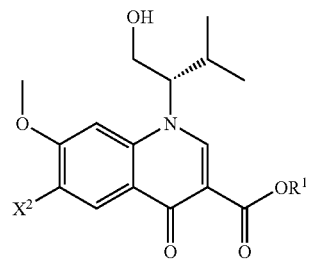
(7-2)

wherein $R^1$ is a $C_1$-$C_4$ alkyl group and $X^2$ is a halogen atom.

[42] Use of a compound represented by the formula (6-B):

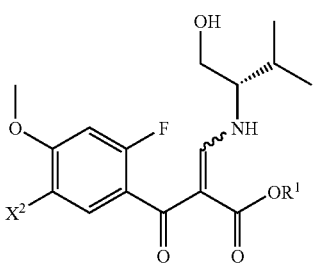
(6-B)

wherein $R^1$ is a $C_1$-$C_4$ alkyl group and $X^2$ is a halogen atom, and a compound represented by the formula (3-B):

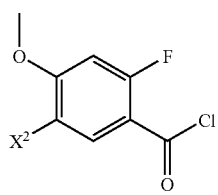
(3-B)

wherein $X^2$ is a halogen atom, for the production of a compound represented by the formula (7-2):

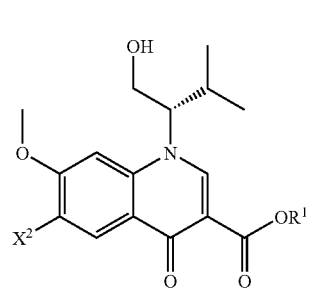
(7-2)

wherein $R^1$ is a $C_1$-$C_4$ alkyl group and $X^2$ is a halogen atom.

[43] Use of a compound represented by the formula (6-B):

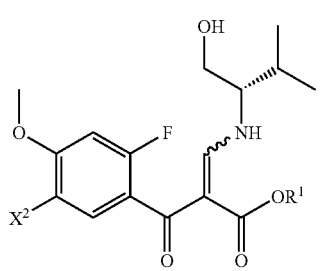
(6-B)

wherein $R^1$ is a $C_1$-$C_4$ alkyl group and $X^2$ is a halogen atom, a compound represented by the formula (4-B):

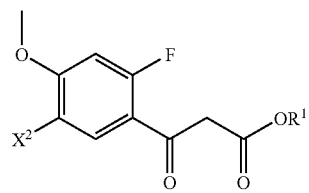
(4-B)

wherein $R^1$ is a $C_1$-$C_4$ alkyl group and $X^2$ is a halogen atom, or a salt thereof, and a compound represented by the formula (3-B):

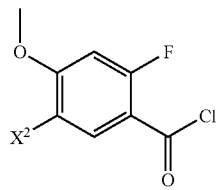
(3-B)

wherein $X^2$ is a halogen atom, for the production of a compound represented by the formula (7-2):

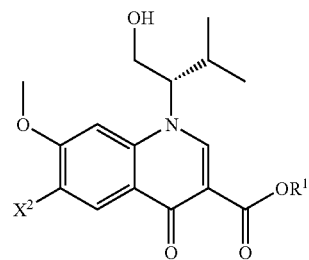
(7-2)

wherein $R^1$ is a $C_1$-$C_4$ alkyl group and $X^2$ is a halogen atom.

[44] Use of a compound represented by the formula (6-B):

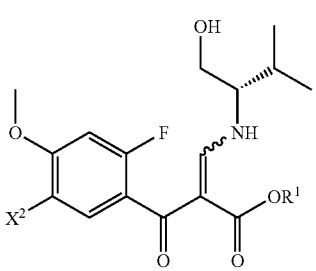
(6-B)

wherein $R^1$ is a $C_1$-$C_4$ alkyl group and $X^2$ is a halogen atom, a compound represented by the formula (5-B):

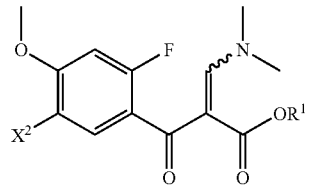
(5-B)

wherein $R^1$ is a $C_1$-$C_4$ alkyl group and $X^2$ is a halogen atom, and a compound represented by the formula (3-B):

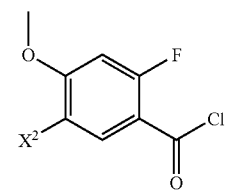
(3-B)

wherein $X^2$ is a halogen atom, for the production of a compound represented by the formula (7-2):

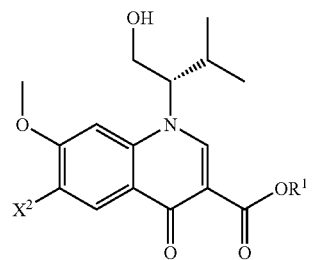
(7-2)

wherein $R^1$ is a $C_1$-$C_4$ alkyl group and $X^2$ is a halogen atom.

[45] Use of a compound represented by the formula (6-B):

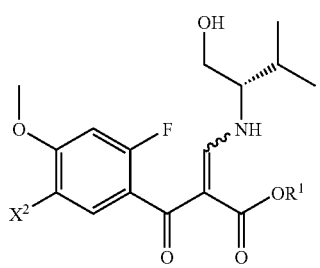
(6-B)

wherein $R^1$ is a $C_1$-$C_4$ alkyl group and $X^2$ is a halogen atom, a compound represented by the formula (5-B):

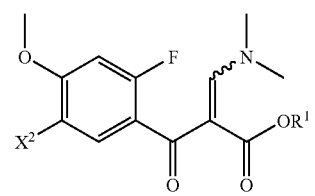
(5-B)

wherein $R^1$ is a $C_1$-$C_4$ alkyl group and $X^2$ is a halogen atom, a compound represented by the formula (4-B):

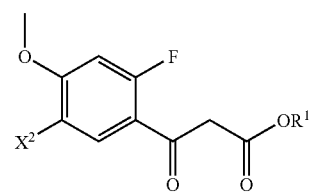
(4-B)

wherein $R^1$ is a $C_1$-$C_4$ alkyl group and $X^2$ is a halogen atom, or a salt thereof, and a compound represented by the formula (3-B):

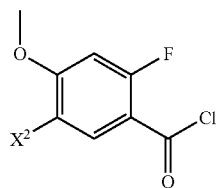
(3-B)

wherein $X^2$ is a halogen atom, for the production of a compound represented by the formula (7-2):

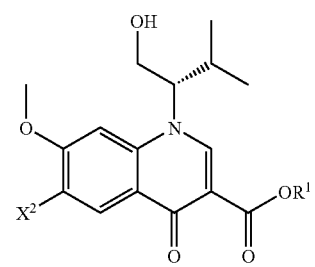
(7-2)

wherein $R^1$ is a $C_1$-$C_4$ alkyl group and $X^2$ is a halogen atom.

[46] Use of a compound represented by the formula (6-B):

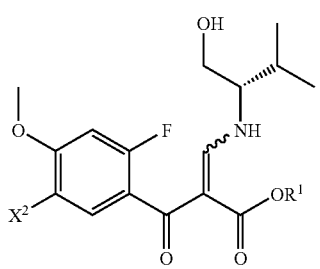
(6-B)

wherein $R^1$ is a $C_1$-$C_4$ alkyl group and $X^2$ is a halogen atom, a compound represented by the formula (5-B):

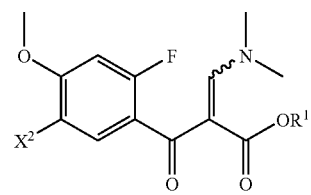
(5-B)

wherein $R^1$ is a $C_1$-$C_4$ alkyl group and $X^2$ is a halogen atom, a compound represented by the formula (4-B):

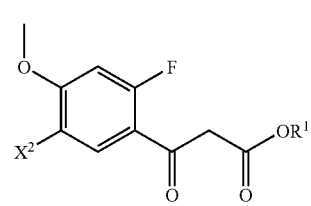
(4-B)

wherein $R^1$ is a $C_1$-$C_4$ alkyl group and $X^2$ is a halogen atom, or a salt thereof, a compound represented by the formula (3-B):

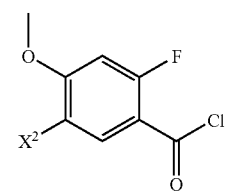
(3-B)

wherein $X^2$ is a halogen atom, a compound represented by the formula (2-B):

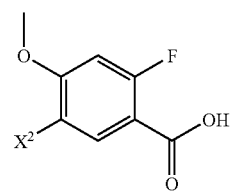
(2-B)

wherein X² is a halogen atom, or a salt thereof, and compound (1-B):

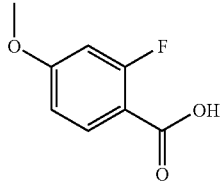

(1-B)

or a salt thereof, for the production of a compound represented by the formula (7-2):

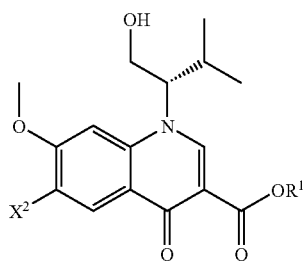

(7-2)

wherein R¹ is a $C_1$-$C_4$ alkyl group and X² is a halogen atom.

[47] A method of producing compound (10)

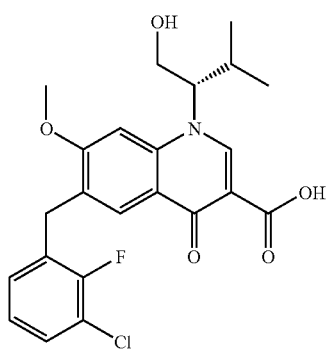

(10)

or a salt thereof, comprising producing the compound from a compound represented by the formula (7-1):

(7-1)

$$\begin{array}{c}\text{OR}^2\\ \\ \text{NH}\\ \\ \text{OR}^1\end{array}$$

wherein R¹ is a $C_1$-$C_4$ alkyl group, R² is a hydroxyl-protecting group and X² is a halogen atom.

[48] A method of producing compound (10)

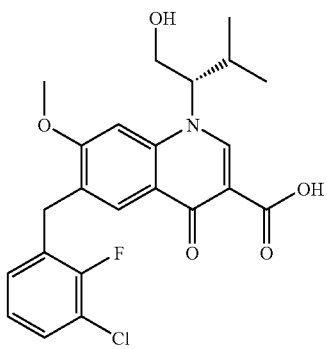

(10)

or a salt thereof, comprising producing the compound from a compound represented by the formula (6-B):

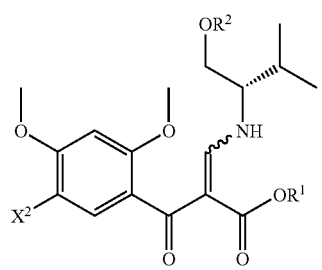

(6-B)

wherein R¹ is a $C_1$-$C_4$ alkyl group and X² is a halogen atom.

[49] A method of producing compound (10)

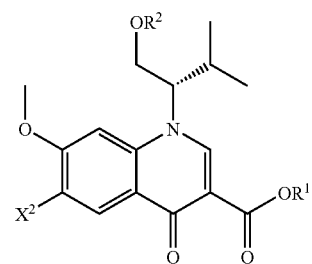

(10)

or a salt thereof, comprising producing the compound from a compound represented by the formula (8):

(8)

$$\begin{array}{c}\text{OR}^2\\ \\ \text{N}\\ \\ \text{OR}^1\end{array}$$

wherein $R^1$ is a $C_1$-$C_4$ alkyl group, $R^2$ is a hydroxyl-protecting group and $X^2$ is a halogen atom.

[50] A method of producing compound (10):

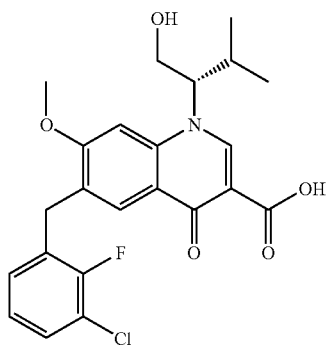
(10)

or a salt thereof, which comprises a step of producing a compound represented by the formula (9):

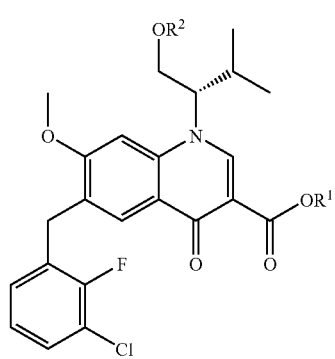
(9)

wherein $R^1$ is a $C_1$-$C_4$ alkyl group and $R^2$ is a hydroxyl-protecting group, from a compound represented by the formula (8):

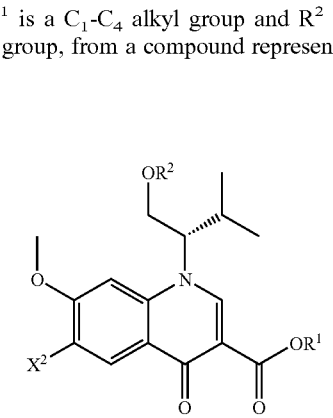
(8)

wherein $R^1$ is a $C_1$-$C_4$ alkyl group, $R^2$ is a hydroxyl-protecting group and $X^2$ is a halogen atom, and a step of producing compound (10) or a salt thereof from compound (9).

[51] The production method of the above-mentioned [50], further comprising a step of producing compound (8) from a compound represented by the formula (7-1):

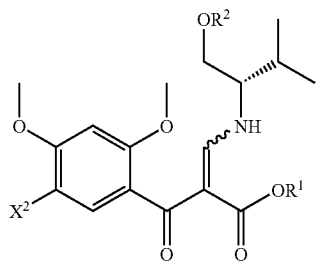
(7-1)

wherein $R^1$ is a $C_1$-$C_4$ alkyl group, $R^2$ is a hydroxyl-protecting group and $X^2$ is a halogen atom.

[52] The production method of the above-mentioned [50], further comprising a step of producing a compound represented by the formula (7-2):

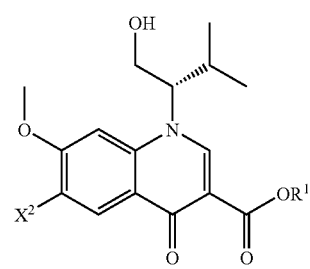
(7-2)

wherein $R^1$ is a $C_1$-$C_4$ alkyl group and $X^2$ is a halogen atom, from a compound represented by the formula (6-B):

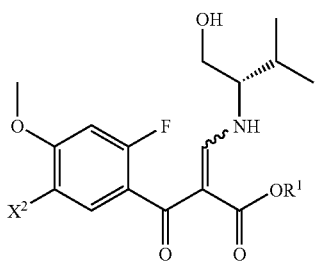
(6-B)

wherein $R^1$ is a $C_1$-$C_4$ alkyl group and $X^2$ is a halogen atom, and a step of producing compound (8) from compound (7-2).

[53] The production method of the above-mentioned [51], further comprising a step of producing a compound represented by the formula (4-A):

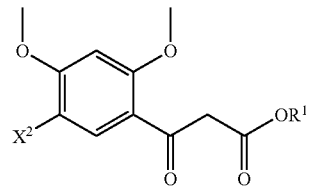
(4-A)

wherein $R^1$ is a $C_1$-$C_4$ alkyl group and $X^2$ is a halogen atom, or a salt thereof, from a compound represented by the formula (3-A):

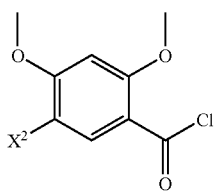

(3-A)

wherein $X^2$ is a halogen atom,
a step of producing a compound represented by the formula (5-A):

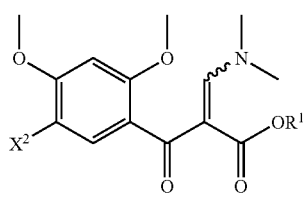

(5-A)

wherein $R^1$ is a $C_1$-$C_4$ alkyl group and $X^2$ is a halogen atom, from compound (4-A) or a salt thereof,
a step of producing a compound represented by the formula (6-A):

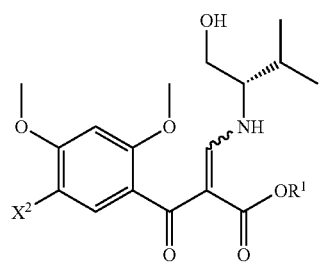

(6-A)

wherein $R^1$ is a $C_1$-$C_4$ alkyl group and $X^2$ is a halogen atom, from compound (5-A), and a step of producing compound (7-1) from compound (6-A).

[54] The production method of the above-mentioned [53], further comprising a step of producing a compound represented by the formula (2-A):

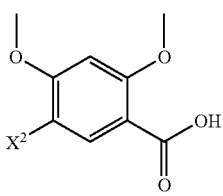

(2-A)

wherein $X^2$ is a halogen atom, or a salt thereof, from compound (1-A):

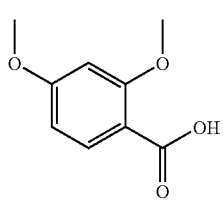

(1-A)

or a salt thereof, and a step of producing a compound represented by the formula (3-A):

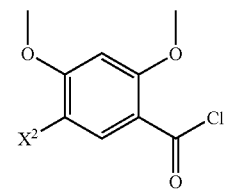

(3-A)

wherein $X^2$ is a halogen atom, from compound (2-A) or a salt thereof.

[55] The production method of the above-mentioned [52], further comprising a step of producing a compound represented by the formula (4-B):

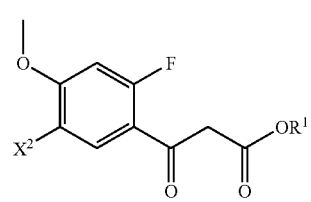

(4-B)

wherein $R^1$ is a $C_1$-$C_4$ alkyl group and $X^2$ is a halogen atom, or a salt thereof, from a compound represented by the formula (3-B):

(3-B)

wherein $X^2$ is a halogen atom,
a step of producing a compound represented by the formula (5-B):

(5-B)

wherein $R^1$ is a $C_1$-$C_4$ alkyl group and $X^2$ is a halogen atom, from compound (4-B) or a salt thereof, and a step of producing compound (6-B) from compound (5-B).

[56] The production method of the above-mentioned [55], further comprising a step of producing a compound represented by the formula (2-B):

(2-B)

wherein $X^2$ is a halogen atom, or a salt thereof, from compound (1-B):

(1-B)

or a salt thereof, and a step of producing a compound represented by the formula (3-B):

(3-B)

wherein $X^2$ is a halogen atom, from compound (2-B) or a salt thereof.

[57] A method of producing a compound represented by the formula (8):

(8)

wherein $R^1$ is a $C_1$-$C_4$ alkyl group, $R^2$ is a hydroxyl-protecting group and $X^2$ is a halogen atom, comprising producing the compound from a compound represented by the formula (3):

(3)

wherein R is a fluorine atom or a methoxy group and $X^2$ is a halogen atom.

[58] A method of producing a compound represented by the formula (8):

(8)

wherein $R^1$ is a $C_1$-$C_4$ alkyl group, $R^2$ is a hydroxyl-protecting group and $X^2$ is a halogen atom, comprising a step of producing a compound represented by the formula (4-A):

(4-A)

wherein $R^1$ is a $C_1$-$C_4$ alkyl group and $X^2$ is a halogen atom, or a salt thereof, from a compound represented by the formula (3-A):

(3-A)

wherein $X^2$ is a halogen atom,
a step of producing a compound represented by the formula (5-A):

(5-A)

wherein $R^1$ is a $C_1$-$C_4$ alkyl group and $X^2$ is a halogen atom, from compound (4-A) or a salt thereof, a step of producing a compound represented by the formula (6-A):

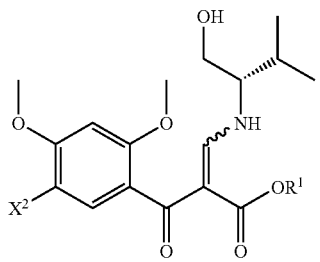
(6-A)

wherein $R^1$ is a $C_1$-$C_4$ alkyl group and $X^2$ is a halogen atom, from compound (5-A),
a step of producing a compound represented by the formula (7-1):

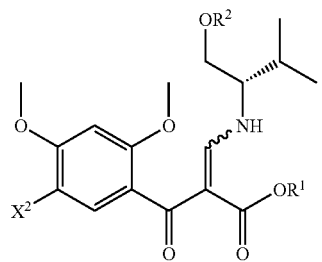
(7-1)

wherein $R^1$ is a $C_1$-$C_4$ alkyl group, $R^2$ is a hydroxyl-protecting group and $X^2$ is a halogen atom, from compound (6-A), and
a step of producing compound (8) from compound (7-1).

[59] A method of producing a compound represented by the formula (8):

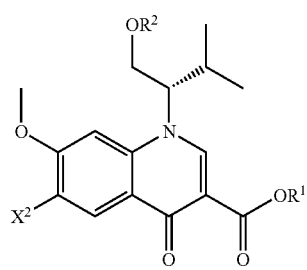
(8)

wherein $R^1$ is a $C_1$-$C_4$ alkyl group, $R^2$ is a hydroxyl-protecting group and $X^2$ is a halogen atom, comprising a step of producing a compound represented by the formula (4-B):

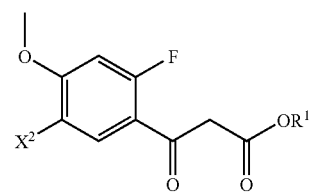
(4-B)

wherein $R^1$ is a $C_1$-$C_4$ alkyl group and $X^2$ is a halogen atom, or a salt thereof, from a compound represented by the formula (3-B):

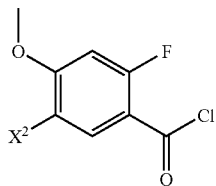
(3-B)

wherein $X^2$ is a halogen atom,
a step of producing a compound represented by the formula (5-B):

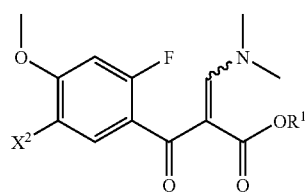
(5-B)

wherein $R^1$ is a $C_1$-$C_4$ alkyl group and $X^2$ is a halogen atom, from compound (4-B) or a salt thereof,
a step of producing a compound represented by the formula (6-B):

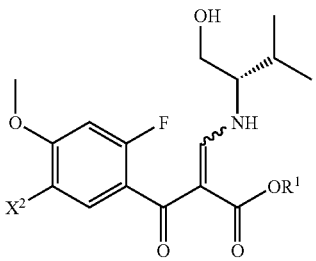
(6-B)

wherein $R^1$ is a $C_1$-$C_4$ alkyl group and $X^2$ is a halogen atom, from compound (5-B),
a step of producing a compound represented by the formula (7-2):

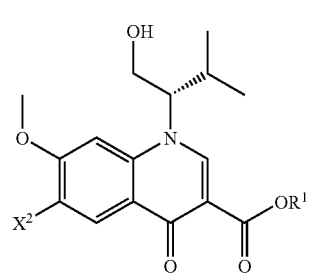
(7-2)

wherein $R^1$ is a $C_1$-$C_4$ alkyl group and $X^2$ is a halogen atom, from compound (6-B), and a step of producing compound (8) from compound (7-2).

[60] The production method of the above-mentioned [58], further comprising a step of producing a compound represented by the formula (2-A):

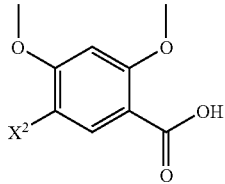

(2-A)

wherein $X^2$ is a halogen atom, or a salt thereof, from compound (1-A):

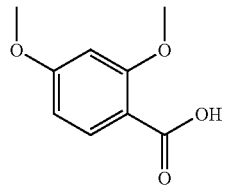

(1-A)

or a salt thereof, and a step of producing a compound represented by the formula (3-A):

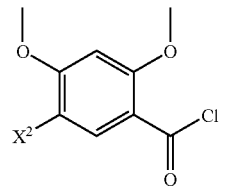

(3-A)

wherein $X^2$ is a halogen atom, from compound (2-A) or a salt thereof.

[61] The production method of the above-mentioned [59], further comprising a step of producing a compound represented by the formula (2-B):

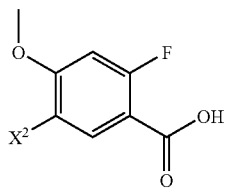

(2-B)

wherein $X^2$ is a halogen atom, or a salt thereof, from compound (1-B):

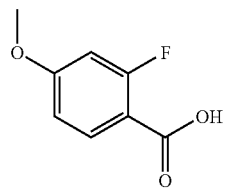

(1-B)

or a salt thereof, and a step of producing a compound represented by the formula (3-B):

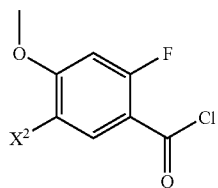

(3-B)

wherein $X^2$ is a halogen atom, from compound (2-B) or a salt thereof.

[62] A method of producing a compound represented by the formula (7-2):

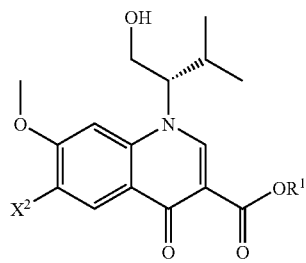

(7-2)

wherein $R^1$ is a $C_1$-$C_4$ alkyl group and $X^2$ is a halogen atom, comprising producing the compound from a compound represented by the formula (3-B):

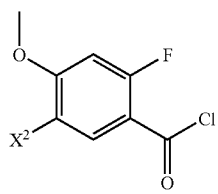

(3-B)

wherein $X^2$ is a halogen atom.

[63] A method of producing a compound represented by the formula (7-2):

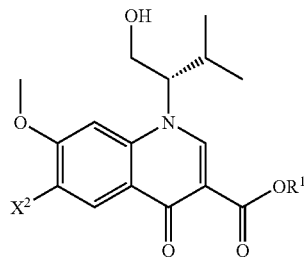

(7-2)

wherein $R^1$ is a $C_1$-$C_4$ alkyl group and $X^2$ is a halogen atom, comprising a step of producing a compound represented by the formula (4-B):

(4-B)

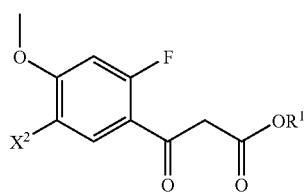

wherein R¹ is a C₁-C₄ alkyl group and X² is a halogen atom, or a salt thereof, from a compound represented by the formula (3-B):

(3-B)

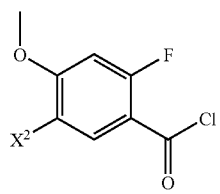

wherein X² is a halogen atom, a step of producing a compound represented by the formula (5-B):

(5-B)

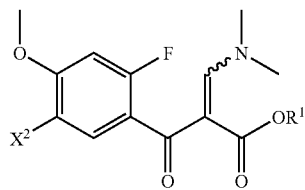

wherein R¹ is a C₁-C₄ alkyl group and X² is a halogen atom, from compound (4-B) or a salt thereof, a step of producing a compound represented by the formula (6-B):

(6-B)

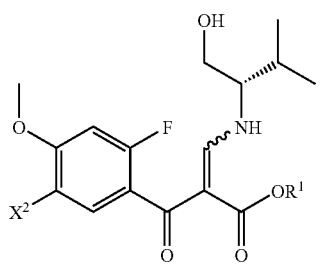

wherein R¹ is a C₁-C₄ alkyl group and X² is a halogen atom, from compound (5-B), and a step of producing a compound represented by the formula (7-2):

(7-2)

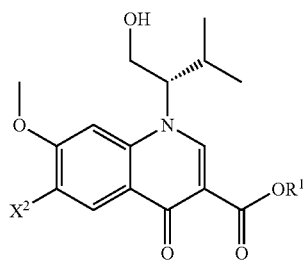

wherein R¹ is a C₁-C₄ alkyl group and X² is a halogen atom, from compound (6-B).

[64] The production method of the above-mentioned [63], further comprising a step of producing a compound represented by the formula (2-B):

(2-B)

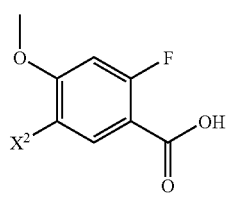

wherein X² is a halogen atom, or a salt thereof, from compound (1-B):

(1-B)

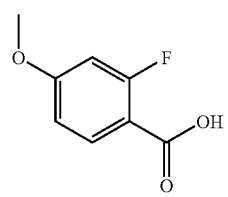

or a salt thereof, and a step of producing a compound represented by the formula (3-B):

(3-B)

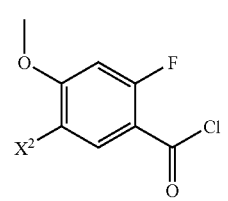

wherein X² is a halogen atom, from compound (2-B) or a salt thereof.

[65] A compound represented by the formula (3-B):

(3-B)

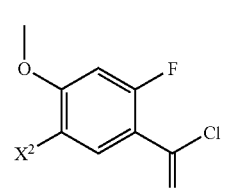

wherein X² is a halogen atom.

[66] A compound represented by the formula (4):

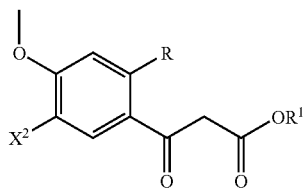

(4)

wherein R is a fluorine atom or a methoxy group, $R^1$ is a $C_1$-$C_4$ alkyl group and $X^2$ is a halogen atom, or a salt thereof.

[67] A compound represented by the formula (5):

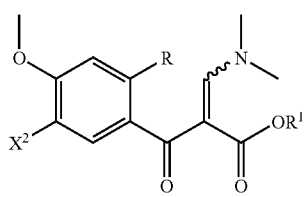

(5)

wherein R is a fluorine atom or a methoxy group, $R^1$ is a $C_1$-$C_4$ alkyl group and $X^2$ is a halogen atom.

[68] A compound represented by the formula (6):

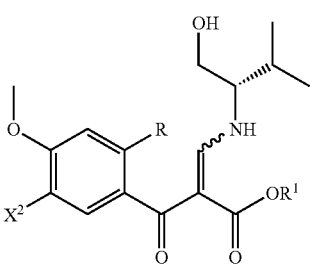

(6)

wherein R is a fluorine atom or a methoxy group, $R^1$ is a $C_1$-$C_4$ alkyl group and $X^2$ is a halogen atom.

[69] A compound represented by the formula (7-1):

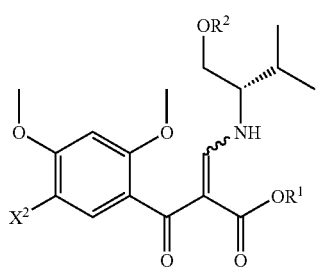

(7-1)

wherein $R^1$ is a $C_1$-$C_4$ alkyl group, $R^2$ is a hydroxyl-protecting group and $X^2$ is a halogen atom.

[70] A compound represented by the formula (7-2):

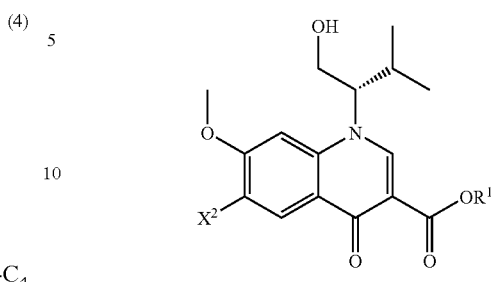

(7-2)

wherein $R^1$ is a $C_1$-$C_4$ alkyl group and $X^2$ is a halogen atom.

[71] A compound represented by the formula (8):

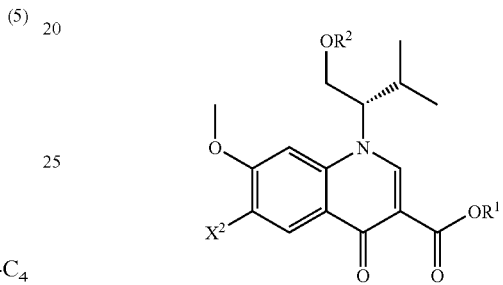

(8)

wherein $R^1$ is a $C_1$-$C_4$ alkyl group, $R^2$ is a hydroxyl-protecting group and $X^2$ is a halogen atom.

[A1] Use of compound (7-1) for the production of compound (10) or a salt thereof.

[A2] Use of compound (7-1) and compound (8) for the production of compound (10) or a salt thereof.

[A3] Use of compound (7-1), compound (8) and compound (9) for the production of compound (10) or a salt thereof.

[A4] Use of compound (3-A) and compound (7-1) for the production of compound (10) or a salt thereof.

[A5] Use of compound (3-A), compound (7-1) and compound (8) for the production of compound (10) or a salt thereof.

[A6] Use of compound (3-A), compound (4-A) or a salt thereof, compound (7-1) and compound (8) for the production of compound (10) or a salt thereof.

[A7] Use of compound (3-A), compound (5-A), compound (7-1) and compound (8) for the production of compound (10) or a salt thereof.

[A8] Use of compound (3-A), compound (4-A) or a salt thereof, compound (5-A), compound (6-A), compound (7-1), compound (8) and compound (9) for the production of compound (10) or a salt thereof.

[A9] Use of compound (1-A) or a salt thereof, compound (2-A) or a salt thereof, compound (3-A), compound (4-A) or a salt thereof, compound (5-A), compound (6-A), compound (7-1), compound (8) and compound (9) for the production of compound (10) or a salt thereof.

[A10] Use of compound (3-A) for the production of compound (8).

[A11] Use of compound (3-A) and compound (7-1) for the production of compound (8).

[A12] Use of compound (3-A), compound (4-A) or a salt thereof, and compound (7-1) for the production of compound (8).

[A13] Use of compound (3-A), compound (5-A) and compound (7-1) for the production of compound (8).

[A14] Use of compound (3-A), compound (4-A) or a salt thereof, compound (5-A), compound (6-A) and compound (7-1) for the production of compound (8).

[A15] Use of compound (1-A) or a salt thereof, compound (2-A) or a salt thereof, compound (3-A), compound (4-A) or a salt thereof, compound (5-A), compound (6-A) and compound (7-1) for the production of compound (8).

[A16] Compound (6-A) or compound (7-1).

[A17] The compound described in the above-mentioned [A16], which is

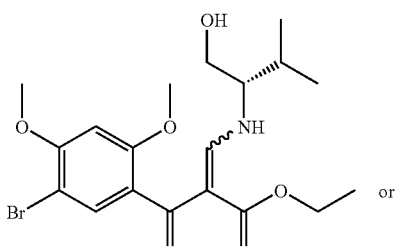

or

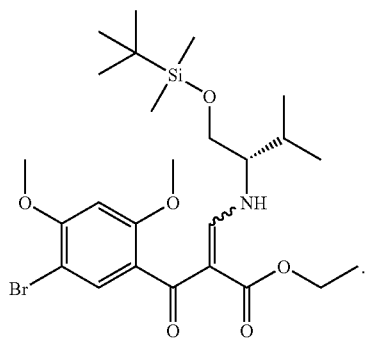

[A18] Compound (8) or compound (9).

[A19] The compound described in the above-mentioned [A18], which is

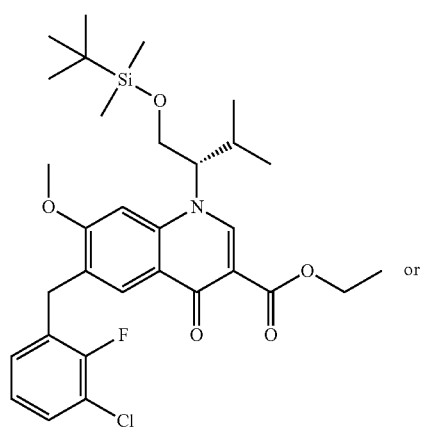

or

-continued

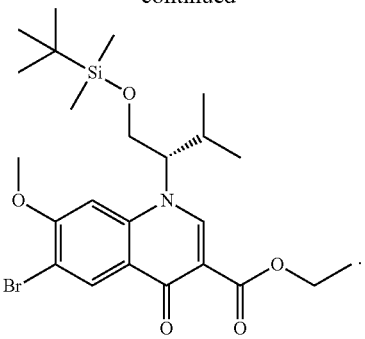

[A20] A method of producing compound (10) or a salt thereof, comprising producing the compound from compound (7-1).

[A21] The production method of the above-mentioned [A20], comprising a step of producing compound (8) from compound (7-1); a step of producing compound (9) from compound (8); and a step of producing compound (10) or a salt thereof from compound (9).

[A22] A method of producing compound (10) or a salt thereof, comprising a step of producing compound (4-A) or a salt thereof from compound (3-A); a step of producing compound (5-A) from compound (4-A) or a salt thereof; a step of producing compound (6-A) from compound (5-A); a step of producing compound (7-1) from compound (6-A); a step of producing compound (8) from compound (7-1); a step of producing compound (9) from compound (8); and a step of producing compound (10) or a salt thereof from compound (9).

[A23] The production method of the above-mentioned [A22], further comprising a step of producing compound (2-A) or a salt thereof from compound (1-A) or a salt thereof; and a step of producing compound (3-A) from compound (2-A) or a salt thereof.

[A24] A method of producing compound (8), comprising producing the compound from compound (3-A).

[A25] A method of producing compound (8), comprising a step of producing compound (4-A) or a salt thereof from compound (3-A); a step of producing compound (5-A) from compound (4-A) or a salt thereof; a step of producing compound (6-A) from compound (5-A); a step of producing compound (7-1) from compound (6-A); and a step of producing compound (8) from compound (7-1).

[A26] The production method described in the above-mentioned

[A25], further comprising a step of producing compound (2-A) or a salt thereof from compound (1-A) or a salt thereof; and a step of producing compound (3-A) from compound (2-A) or a salt thereof.

[B1] Use of compound (6-B) for the production of compound (10) or a salt thereof.

[B2] Use of compound (6-B) and compound (7-2) for the production of compound (10) or a salt thereof.

[B3] Use of compound (6-B) and compound (8) for the production of compound (10) or a salt thereof.

[B4] Use of compound (6-B), compound (7-2), compound (8) and compound (9) for the production of compound (10) or a salt thereof.

[B5] Use of compound (3-B) and compound (6-B) for the production of compound (10) or a salt thereof.

[B6] Use of compound (3-B), compound (4-B) or a salt thereof, and compound (6-B) for the production of compound (10) or a salt thereof.

[B7] Use of compound (3-B), compound (5-B) and compound (6-B) for the production of compound (10) or a salt thereof.

[B8] Use of compound (3-B), compound (4-B) or a salt thereof, compound (6-B) and compound (7-2) for the production of compound (10) or a salt thereof.

[B9] Use of compound (3-B), compound (4-B) or a salt thereof, compound (6-B) and compound (8) for the production of compound (10) or a salt thereof.

[B10] Use of compound (3-B), compound (5-B), compound (6-B) and compound (7-2) for the production of compound (10) or a salt thereof.

[B11] Use of compound (3-B), compound (5-B), compound (6-B) and compound (8) for the production of compound (10) or a salt thereof.

[B12] Use of compound (3-B), compound (4-B) or a salt thereof, compound (5-B), compound (6-B), compound (7-2), compound (8) and compound (9) for the production of compound (10) or a salt thereof.

[B13] Use of compound (1-B) or a salt thereof, compound (2-B) or a salt thereof, compound (3-B), compound (4-B) or a salt thereof, compound (5-B), compound (6-B), compound (7-2), compound (8) and compound (9) for the production of compound (10) or a salt thereof.

[B14] Use of compound (3-B) for the production of compound (7-2).

[B15] Use of compound (3-B) and compound (6-B) for the production of compound (7-2).

[B16] Use of compound (3-B), compound (4-B) or a salt thereof, and compound (6-B) for the production of compound (7-2).

[B17] Use of compound (3-B), compound (5-B) and compound (6-B) for the production of compound (7-2).

[B18] Use of compound (3-B), compound (4-B) or a salt thereof, compound (5-B) and compound (6-B) for the production of compound (7-2).

[B19] Use of compound (1-B) or a salt thereof, compound (2-B) or a salt thereof, compound (3-B), compound (4-B) or a salt thereof, compound (5-B) and compound (6-B) for the production of compound (7-2).

[B20] Compound (6-B).

[B21] The compound of the above-mentioned [B20], which is

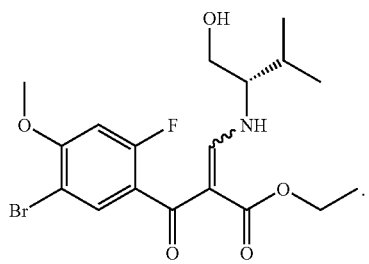 [SMILES: CCOC(=O)C(=CN[C@H](CO)C(C)C)C(=O)c1cc(Br)c(OC)cc1F ; "."]

[B22] Compound (7-2).

[B23] The compound of the above-mentioned [B22], which is

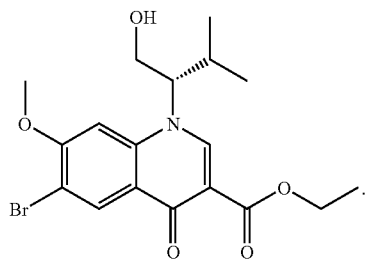 [SMILES: CCOC(=O)c1cn([C@H](CO)C(C)C)c2cc(OC)c(Br)cc2c1=O ; "."]

[B24] A method of producing compound (10) or a salt thereof, comprising producing the compound from compound (6-B).

[B25] The production method of the above-mentioned [B24], comprising a step of producing compound (7-2) from compound (6-B); a step of producing compound (8) from compound (7-2); a step of producing compound (9) from compound (8); and a step of producing compound (10) or a salt thereof from compound (9).

[B26] A method of producing compound (10) or a salt thereof, comprising a step of producing compound (4-B) or a salt thereof from compound (3-B); a step of producing compound (5-B) from compound (4-B) or a salt thereof; a step of producing compound (6-B) from compound (5-B); a step of producing compound (7-2) from compound (6-B); a step of producing compound (8) from compound (7-2); a step of producing compound (9) from compound (8); and a step of producing compound (10) or a salt thereof from compound (9).

[B27] The production method of the above-mentioned [B26], further comprising a step of producing compound (2-B) or a salt thereof from compound (1-B) or a salt thereof; and a step of producing compound (3-B) from compound (2-B) or a salt thereof.

[B28] A method of producing compound (7-2), comprising producing the compound from compound (3-B).

[B29] A production method of compound (7-2), comprising a step of producing compound (4-B) or a salt thereof from compound (3-B); a step of producing compound (5-B) from compound (4-B) or a salt thereof; a step of producing compound (6-B) from compound (5-B); and a step of producing compound (7-2) from compound (6-B).

[B30] The production method of the above-mentioned [B29], further comprising a step of producing compound (2-B) or a salt thereof from compound (1-B) or a salt thereof; and a step of producing compound (3-B) from compound (2-B) or a salt thereof.

Effect of the Invention

The present invention can provide novel compounds (6), (7-1), (7-2) and (8) useful as synthetic intermediates for anti-HIV agents (compounds) having an integrase inhibitory activity, production methods of the synthetic intermediates, and production methods of anti-HIV agents (compounds) (e.g., compound (10) and the like) using the synthetic intermediates.

The present invention can provide an industrially highly valuable production method of an anti-HIV agent (compound). For example, using an intermediate compound having a methoxy group in advance as a synthetic intermediate for the production of compound (10), which is an anti-HIV agent (compound), a decrease in the yield due to the final step (alkoxylation, particularly methoxylation) in the prior art and by-production of sodium fluoride can be avoided. Using compound (6-A) and/or compound (7-1) in a ring closure step, moreover, the generation of hydrogen fluoride (HF) that causes corrosion of the production facility can be avoided, whereby problems in the prior art (avoidance of decreased yield, corrosion of production facility, etc.) can be overcome.

Further, the present invention can also provide production methods of the above-mentioned synthetic intermediates.

Since the above-mentioned synthetic intermediates can overcome the above-mentioned problems in the prior art during the production of an anti-HIV agent (compound), a production method of the synthetic intermediate also has a high value for industrial application and is significant.

Of the synthetic intermediates, compound (7-2) and compound (8) are stable by themselves, and can tolerate severe conditions and/or long-term preservation. Furthermore, since the quality thereof influences the progress of a palladium catalyst reaction in the next step, and is also directly related to the quality of anti-HIV agents (compounds) (e.g., compound (10) and the like), they are extremely important intermediate compounds.

Moreover, highly distributable compound (1) is used as a starting material in the present invention. Thus, the production method of the present invention can produce an anti-HIV agent (compound) more economically, since stability of supply of the starting material can be improved.

BEST MODE FOR EMBODYING THE INVENTION

Detailed Description of the Invention

The terms and symbols to be used in the present invention are defined in the following.

A "halogen atom" means a fluorine atom, a chlorine atom, a bromine atom or an iodine atom.

A "$C_1$-$C_4$ alkyl group" means a straight chain or branched chain alkyl group having 1 to 4 carbon atoms, and specific examples include methyl group, ethyl group, propyl group, isopropyl group, butyl group, isobutyl group, sec-butyl group and tert-butyl group.

A "hydroxyl-protecting group" means a general hydroxyl-protecting group known to those of ordinary skill in the art, which is introduced to prevent reaction of the hydroxyl group. Examples thereof include the protecting groups described in Protective Groups in Organic Synthesis, published by John Wiley and Sons (1980) and the like, and specific examples thereof include ether-protecting groups such as tetrahydropyranyl group, methoxymethyl group and the like; carbonate-protecting groups such as methylcarbonate group, ethylcarbonate group and the like; silicon-protecting groups such as trimethylsilyl group, tert-butyldimethylsilyl group, tert-butyldiphenylsilyl group, etc. and the like.

R is a fluorine atom or a methoxy group.

$R^1$ is a "$C_1$-$C_4$ alkyl group", preferably a methyl group or an ethyl group.

$R^2$ is a "hydroxyl-protecting group", preferably a silicon protecting group, more preferably a tert-butyldimethylsilyl group.

$X^1$ is a "halogen atom", preferably a chlorine atom or a bromine atom.

$X^2$ is a "halogen atom", preferably a bromine atom or an iodine atom, more preferably a bromine atom.

Compound (1) [compounds (1-A) and (1-B)], compound (2) [compounds (2-A) and (2-B)], compound (4) [compounds (4-A) and (4-B)] and compound (10) used or produced in the present invention may be in the form of salts.

The "salt" may be any nontoxic salt as long as it can be formed from the compound to be used in the present invention and, for example, salts obtained by reaction with inorganic acids such as hydrochloric acid, sulfuric acid, phosphoric acid, hydrobromic acid and the like; organic acids such as oxalic acid, malonic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid and the like; inorganic bases such as sodium hydroxide, potassium hydroxide, calcium hydroxide, magnesium hydroxide, ammonium hydroxide and the like; organic bases such as methylamine, diethylamine, triethylamine, triethanolamine, ethylenediamine, tris(hydroxymethyl)methylamine, guanidine, choline, cinchonine and the like; amino acid such as lysin, arginine, alanine and the like, and the like can be mentioned. The compound used in the present invention also encompasses a water-containing product, a hydrate and a solvate of each compound.

In addition, the compound used in the present invention may have various isomers. For example, when a double bond is present, E form and Z form are present as geometric isomers. Moreover, tautomer can also be present. Further, when an optical isomer may be present as an isomer, each optical isomer and a mixture thereof are also encompassed in the present invention. When desired, these isomers may be optically resolved or individually produced by a method known per se.

Accordingly, those of ordinary skill in the art should understand that all of these isomers and mixtures thereof are encompassed in the present invention. The compound of the present invention is preferably isolated and purified from various isomers, by-products, metabolites and prodrugs, and preferably has a purity of not less than 90%, more preferably not less than 95%.

One example of the production method of the present invention is explained in the following. However, the present invention is not limited thereto.

Even in the absence of description in the production method, those of ordinary skill in the art will understand that an efficient production can be performed by employing, where necessary, introduction of a protecting group into a functional group, removal of the protecting group during workup, conversion to a desired functional group at any stage and the like.

The workup after reaction in each step can be applied by a typical method, wherein isolation and purification is performed by selecting or combining conventional methods as necessary, such as crystallization, recrystallization, distillation, partition, silica gel chromatography, preparative HPLC and the like.

In the following production method and the present invention, "room temperature" means generally 15° C.-30° C., unless particularly described.

Unless otherwise specified, the amount of the solvent to be used in the following production method and the present invention is an amount that can be stirred in the reaction system.

The production method of compound (10) or a salt thereof, which is an anti-HIV agent (compound), from compound (1) or a salt thereof, is shown in the following scheme. Specifically, a method using compound (1-A), which is compound (1) wherein R is a methoxy group is shown as scheme 1 below, and a method using compound (1-B), which is compound (1) wherein R is a fluorine atom is shown as scheme 2 below.

Scheme 1
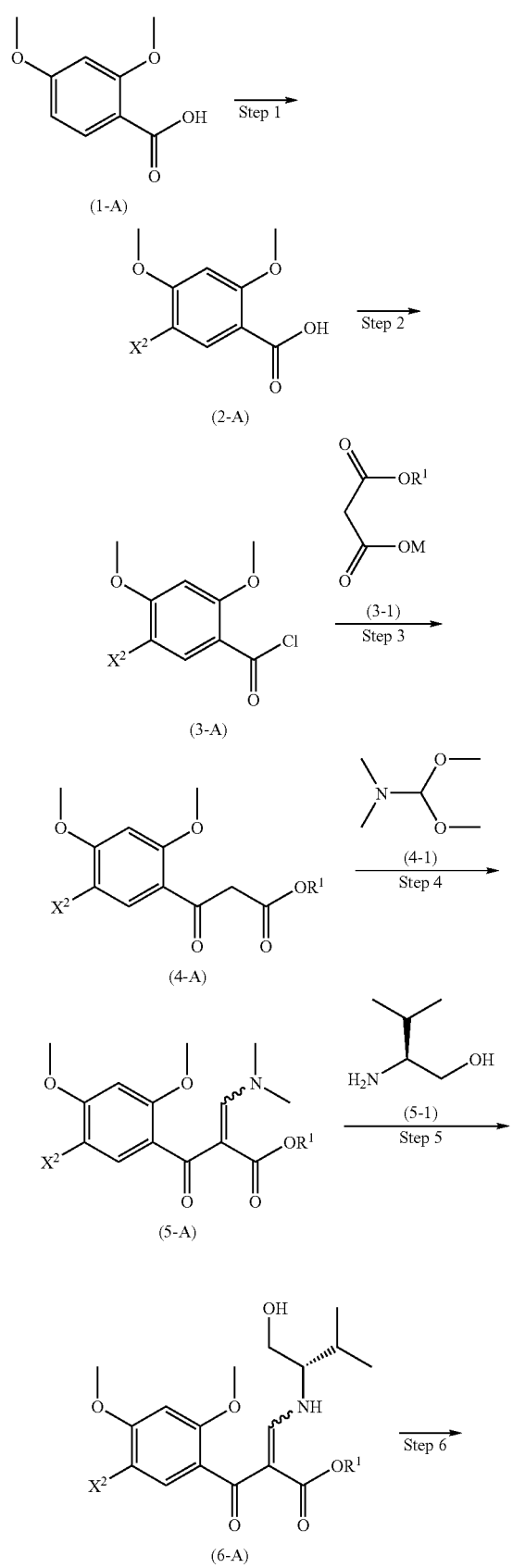
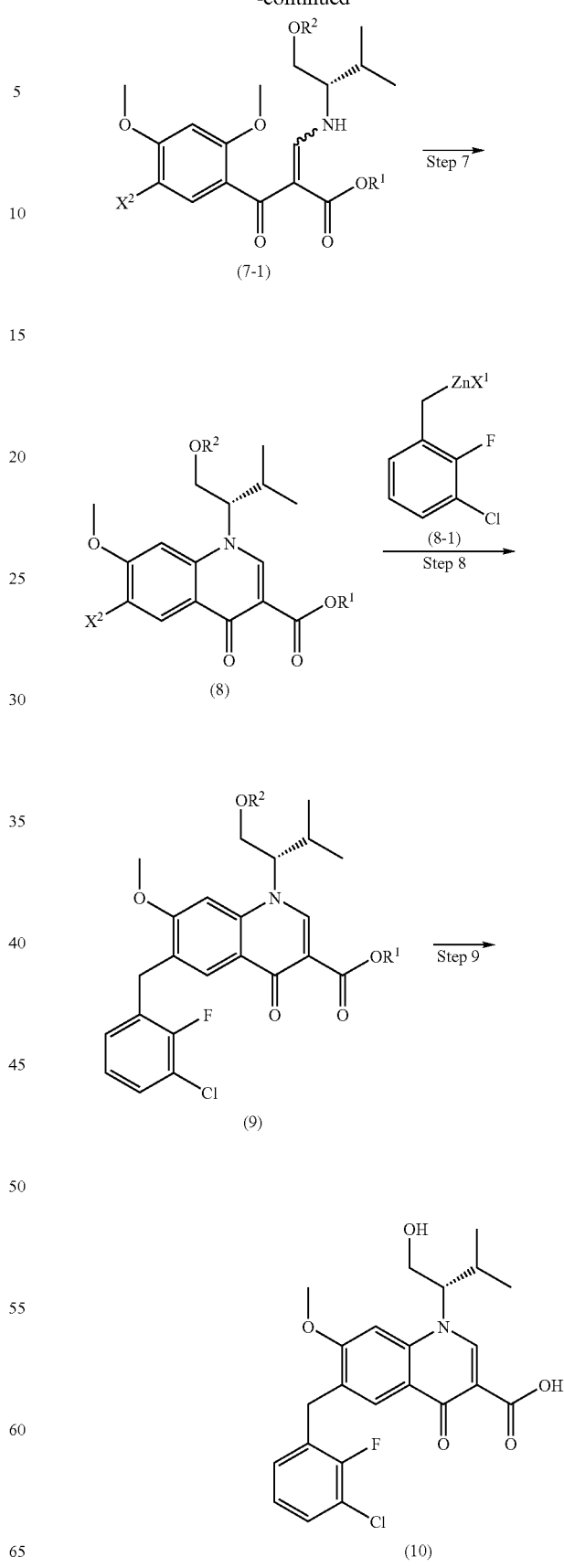

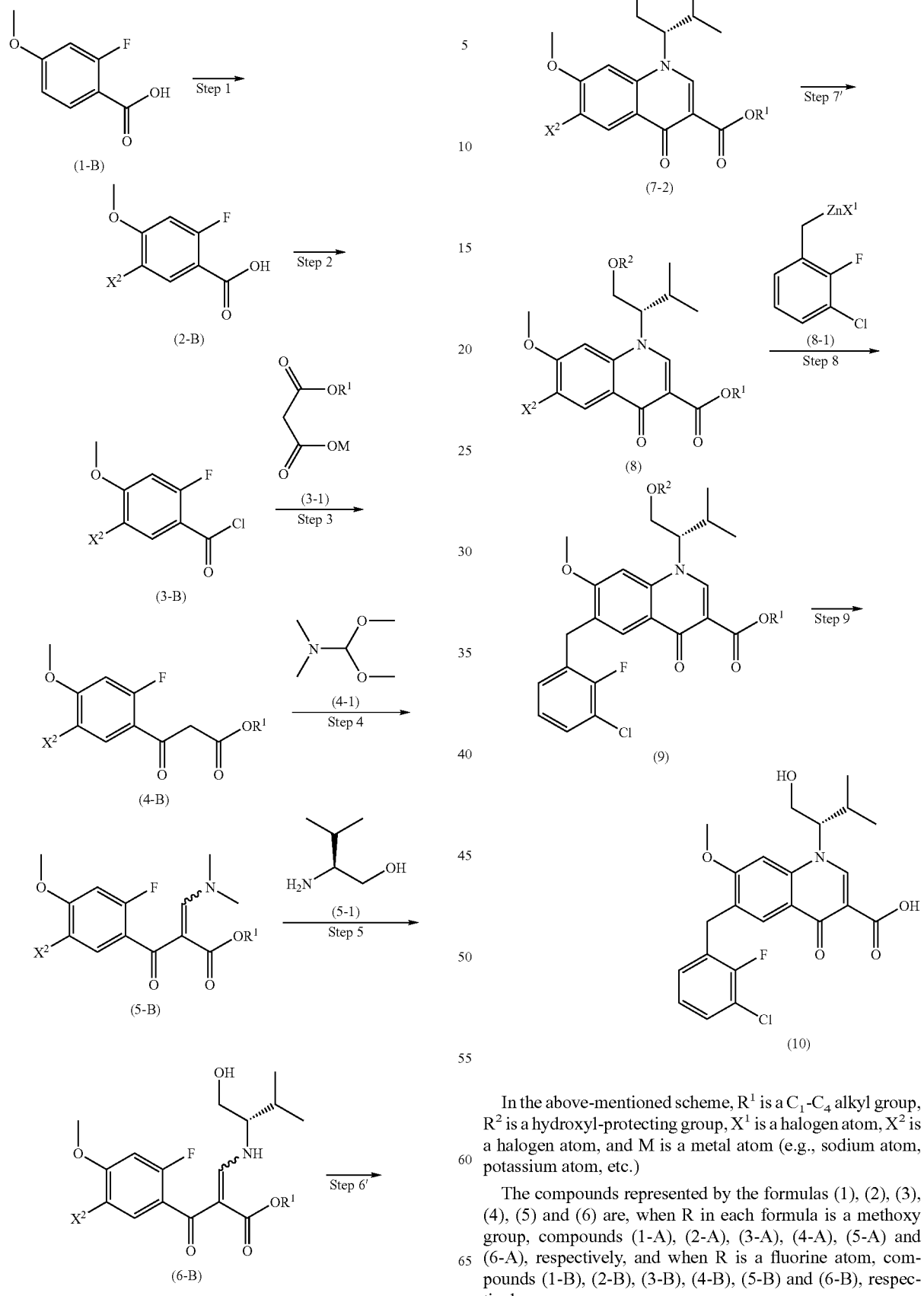

In the above-mentioned scheme, $R^1$ is a $C_1$-$C_4$ alkyl group, $R^2$ is a hydroxyl-protecting group, $X^1$ is a halogen atom, $X^2$ is a halogen atom, and M is a metal atom (e.g., sodium atom, potassium atom, etc.)

The compounds represented by the formulas (1), (2), (3), (4), (5) and (6) are, when R in each formula is a methoxy group, compounds (1-A), (2-A), (3-A), (4-A), (5-A) and (6-A), respectively, and when R is a fluorine atom, compounds (1-B), (2-B), (3-B), (4-B), (5-B) and (6-B), respectively.

Step 1

Compound (2) or a salt thereof can be produced by reacting compound (1) or a salt thereof with a halogenating agent in a solvent.

Compound (1) and a salt thereof may be commercially available products, or can be synthesized separately according to a known technique.

Examples of the halogenating agent include brominating agents such as bromine, N-bromosuccinimide and the like, and iodinating agents such as iodine, N-iodosuccinimide and the like. A brominating agent is preferable and bromine is more preferable.

The amount of the halogenating agent to be used is generally 1.0 to 2.0 mol, preferably 1.0 to 1.2 mol, per 1 mol of compound (1).

In addition, a sulfite (e.g., sodium sulfite etc.) may be added after completion of the reaction, for the purpose of treating the free halogen.

The amount of the sulfite to be used is generally 0 to 1.1 mol, preferably 0 to 0.3 mol, per 1 mol of compound (1).

Examples of the solvent include halogenated solvents such as dichloromethane, chloroform, carbon tetrachloride, 1,2-dichloroethane and the like; polar solvents such as N,N-dimethylformamide (DMF), N,N-dimethylacetamide (DMA), dimethyl sulfoxide, acetonitrile and the like; acidic solvents such as trifluoromethanesulfonic acid, sulfuric acid, acetic acid and the like or a mixed solvent thereof and the like. An acidic solvent is preferable and acetic acid is particularly preferable.

The reaction temperature is, when R is a methoxy group (that is, when compound (2-A) or a salt thereof is produced from compound (1-A) or a salt thereof), generally 0° C. to 50° C., preferably 15° C. to 30° C., and when R is a fluorine atom (that is, when compound (2-B) or a salt thereof is produced from compound (1-B) or a salt thereof), generally 0° C. to 100° C., preferably 0° C. to 70° C.

The reaction time is generally 1 hr to 48 hr, preferably 1 hr to 12 hr. When R is a methoxy group, more preferable reaction time is 1 hr to 3 hr, and when R is a fluorine atom, more preferable reaction time is 1 hr to 9 hr.

Step 2

According to a conventional method, compound (3) can be obtained by reacting compound (2) or a salt thereof with a chlorinating agent in a solvent.

Compound (2) and a salt thereof can be obtained in the same manner as in the above-mentioned step 1, and the compound wherein R is a methoxy group, which is compound (2-A) and a salt thereof may be a commercially available product, or can be synthesized separately according to a known technique.

Examples of the chlorinating agent include oxalyl chloride, phosphorus oxychloride, thionyl chloride and the like, with preference given to thionyl chloride. When oxalyl chloride or thionyl chloride is used as a chlorinating agent, a catalyst (e.g., N,N-dimethylformamide etc.) may be added.

The amount of the chlorinating agent to be used is generally 1.0 to 1.5 mol, preferably 1.0 to 1.2 mol, per 1 mol of compound (2).

Examples of the solvent include hydrocarbon solvents such as toluene, xylene, hexane, heptane and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile and the like or a mixed solvent thereof and the like. A hydrocarbon solvent is preferable and toluene is more preferable.

The reaction temperature is generally 0° C. to 100° C., preferably 60° C. to 80° C., more preferably 70° C. to 80° C.

The reaction time is generally 1 hr to 24 hr, preferably 1 hr to 10 hr, more preferably 1 hr to 5 hr.

The reaction is preferably carried out under argon atmosphere or under nitrogen atmosphere, particularly preferably under nitrogen atmosphere.

Step 3

Compound (4) or a salt thereof, which is a β-ketoester, can be produced, in a solvent, in the presence of a base and a chelator, by reacting a malonic acid monoester represented by the formula (3-1) or a salt thereof (hereinafter sometimes to be abbreviated as compound (3-1)) with compound (3), and treating the resulting compound with an acid.

Compound (3) can be obtained in the same manner as in the above-mentioned step 2. The compound wherein R is a methoxy group, which is compound (3-A) may be a commercially available product, or can be synthesized separately according to a known technique.

In compound (3-1), a sodium atom or a potassium atom is preferable as a metal atom for M, more preferably a potassium atom.

Compound (3-1) may be a commercially available product, or can be synthesized separately according to a known technique. It is particularly preferably potassium ethyl malonate.

The amount of compound (3-1) to be used is generally 1 to 10 mol, preferably 1.0 to 2.0 mol, per 1 mol of compound (3).

Examples of the base include organic bases such as triethylamine, N-methylmorpholine and the like, with preference given to triethylamine.

The amount of the base to be used is generally 1 to 10 mol, preferably 2.0 to 3.0 mol, per 1 mol of compound (3).

Examples of the chelator include a divalent magnesium compound (e.g., magnesium chloride) and the like, with preference given to magnesium chloride.

The amount of the chelator to be used is generally 1 to 10 mol, preferably 2.0 to 3.0 mol, per 1 mol of compound (3).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile and the like or a mixed solvent thereof and the like. When R is a methoxy group, a preferable solvent is an ether solvent, an ester solvent or a mixed solvent thereof, more preferably tetrahydrofuran, ethyl acetate, or a mixed solvent thereof. When R is a fluorine atom, a preferable solvent is an ether solvent, a hydrocarbon solvent or a mixed solvent thereof, more preferably tetrahydrofuran, toluene or a mixed solvent thereof.

The reaction temperature is generally 0° C. to 100° C. When R is a methoxy group, a preferable reaction temperature is 60° C. to 80° C., more preferably 70° C. to 80° C. When R is a fluorine atom, a preferable reaction temperature is 50° C. to 80° C., more preferably 60° C. to 80° C.

The reaction time is generally 1 hr to 24 hr, preferably 2 hr to 10 hr, more preferably 2 hr to 5 hr.

Examples of the acid include acetic acid, hydrochloric acid, sulfuric acid and the like, with preference given to hydrochloric acid.

The amount of the acid to be used is not particularly limited.

The reaction temperature after the addition of the acid is generally 0° C. to 100° C., preferably 0° C. to 50° C., more preferably 15° C. to 30° C. The reaction time is generally 0.5 hr to 10 hr, preferably 0.5 hr to 5 hr, more preferably 0.5 hr to 2 hr.

The reaction is preferably carried out under argon atmosphere or under nitrogen atmosphere, particularly preferably under nitrogen atmosphere.

Step 4

Compound (5) can be obtained by reacting compound (4) or a salt thereof with a compound represented by the formula (4-1) (hereinafter sometimes to be abbreviated as compound (4-1)): N,N-dimethylformamide dimethyl acetal in a solvent.

Compound (4) and a salt thereof can be obtained in the same manner as in the above-mentioned Step 3.

Compound (4-1) may be a commercially available product, or can be synthesized separately according to a known technique.

The amount of compound (4-1) to be used is generally 1 to 10 mol, preferably 1.0 to 2 mol, particularly preferably 1.0 to 1.5 mol, per 1 mol of compound (4).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile and the like or a mixed solvent thereof and the like, with preference given to toluene.

The reaction temperature is generally 20° C. to 110° C. When R is a methoxy group, a preferable reaction temperature is 70° C. to 110° C., more preferably 90° C. to 100° C. When R is a fluorine atom, a preferable reaction temperature is 50° C. to 100° C., more preferably 70° C. to 90° C.

When R is a methoxy group, the reaction time is generally 1 hr to 48 hr, preferably 10 hr to 24 hr, more preferably 15 hr to 24 hr. When R is a fluorine atom, the reaction time is generally 1 hr to 24 hr, preferably 1 hr to 8 hr, more preferably 1 hr to 4 hr.

The reaction is preferably carried out under argon atmosphere or under nitrogen atmosphere, particularly preferably under nitrogen atmosphere.

Step 5-1

Compound (6) can be obtained by reacting compound (5) with a compound represented by the formula (5-1) (hereinafter sometimes to be abbreviated as compound (5-1)): L-valinol((S)-2-amino-3-methylbutan-1-ol) in a solvent.

Compound (5-1) may be a commercially available product, or can be synthesized separately according to a known technique. The optical purity of compound (5-1) is not less than 95% ee, preferably not less than 97% ee, more preferably not less than 99% ee.

The amount of compound (5-1) to be used is generally 1 to 10 mol, preferably 1 to 2 mol, particularly preferably 1.1 to 1.3 mol, per 1 mol of compound (5).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile and the like or a mixed solvent thereof and the like, with preference given to toluene.

The reaction temperature is generally 0° C. to 100° C., preferably 0° C. to 50° C., more preferably 0° C. to 30° C.

The reaction time is generally 0.5 hr to 24 hr, preferably 0.5 hr to 12 hr, more preferably 0.5 hr to 3 hr.

The reaction is preferably carried out under argon atmosphere or under nitrogen atmosphere, particularly preferably under nitrogen atmosphere.

Step 5-2

When R is a methoxy group (that is, when compound (5) is compound (5-A)), compound (7-1) can be directly obtained by reacting compound (5-A) with a compound which is compound (5-1) wherein the hydroxyl group is protected by the above-mentioned "hydroxyl-protecting group" in a solvent.

Compound (5-1) protected by the hydroxyl-protecting group can be synthesized separately according to a known technique. Examples of the compound (5-1) protected by the "hydroxyl-protecting group" include (S)-1-(tert-butyldimethylsilanyloxymethyl)-2-methylpropylamine, (S)-2-methyl-1-(trimethylsilanyloxymethyl)propylamine, (S)-2-methyl-1-(tetrahydropyran-2-yloxymethyl)propylamine, methyl 2-amino-3-methylbutylcarbonate and ethyl 2-amino-3-methylbutylcarbonate. It is preferably (S)-1-(tert-butyldimethylsilanyloxymethyl)-2-methylpropylamine, (S)-2-methyl-1-(tetrahydropyran-2-yloxymethyl)propylamine or methyl 2-amino-3-methylbutylcarbonate, particularly preferably (S)-1-(tert-butyldimethylsilanyloxymethyl)-2-methylpropylamine.

The optical purity of compound (5-1) protected by the hydroxyl-protecting group is not less than 95% ee, preferably not less than 97% ee, more preferably not less than 99% ee.

The amount of compound (5-1) protected by the hydroxyl-protecting group to be used is generally 1 to 10 mol, preferably 1 to 2 mol, particularly preferably 1.1 to 1.3 mol, per 1 mol of compound (5-A).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile and the like or a mixed solvent thereof and the like, with preference given to toluene.

The reaction temperature is generally 0° C. to 100° C., preferably 0° C. to 50° C., more preferably 0° C. to 30° C.

The reaction time is generally 0.5 hr to 24 hr, preferably 0.5 hr to 12 hr, more preferably 0.5 hr to 3 hr.

The reaction is preferably carried out under argon atmosphere or under nitrogen atmosphere, particularly preferably under nitrogen atmosphere.

Step 6

In step 6, compound (7-1) is produced by introducing a protecting group into a hydroxyl group of compound (6) wherein R is a methoxy group (i.e., compound (6-A)). Compound (7-1) can be obtained by introducing a protecting group into the hydroxyl group of compound (6-A) in a solvent according to a conventional method.

For example, when the hydroxyl-protecting group is a tert-butyldimethylsilyl group, compound (7-1) can be obtained by adding a base and tert-butyldimethylsilyl chloride to compound (6-A) in a solvent.

The amount of the tert-butyldimethylsilyl chloride to be used is generally 1 to 10 mol, preferably 1 to 2 mol, particularly preferably 1 to 1.3 mol, per 1 mol of compound (6-A).

Examples of the base include triethylamine, diisopropylethylamine, pyridine, imidazole and the like. It is preferably imidazole.

The amount of the base to be used is generally 1 to 10 mol, preferably 1 to 2 mol, particularly preferably 1 to 1.3 mol, per 1 mol of compound (6-A).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile, water and the like or a mixed solvent thereof and the like. An ether solvent, a hydrocarbon solvent, a mixed solvent thereof or the like is preferable and tetrahydrofuran, toluene, a mixed solvent thereof or the like is more preferable.

The reaction temperature is generally 0° C. to 100° C., preferably 15° C. to 70° C., more preferably 40° C. to 50° C.

The reaction time is generally 1 hr to 24 hr, preferably 1 hr to 10 hr, more preferably 1 hr to 5 hr.

The reaction is preferably carried out under argon atmosphere or under nitrogen atmosphere, particularly preferably under nitrogen atmosphere.

Step 7

Compound (8) can be obtained by subjecting compound (7-1) to a cyclization reaction in a solvent. A base and an additive can be added to the reaction system.

Examples of the base include sodium carbonate, potassium carbonate, sodium hydroxide, potassium hydroxide, potassium tert-butoxide, sodium hydride, potassium hydride, 1,8-diazabicyclo[5.4.0]-7-undecene and the like, with preference given to potassium carbonate.

The amount of the base to be used is generally 0.5 to 10 mol, preferably 0.5 to 2 mol, particularly preferably 0.5 to 1 mol, per 1 mol of compound (7-1).

Examples of the additive include quaternary ammonium salts such as tetra-n-butylammonium bromide and the like, quaternary phosphonium salts such as tetra-n-butylphosphonium bromide and the like, crown ethers such as 18-crown-6 and the like, and the like. A quaternary ammonium salt, a quaternary phosphonium salt or crown ether is preferable and tetra-n-butylphosphonium bromide is more preferable.

The amount of the additive to be used is generally 0.05 to 10 mol, preferably 0.05 to 2 mol, particularly preferably 0.05 to 1.0 mol, per 1 mol of compound (7-1).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to toluene.

The reaction temperature is generally 20° C. to 140° C., preferably 90° C. to 120° C., more preferably 100° C. to 110° C.

The reaction time is generally 1 hr to 24 hr, preferably 4 hr to 20 hr, more preferably 8 hr to 16 hr.

The reaction is preferably carried out under argon atmosphere or under nitrogen atmosphere, particularly preferably under nitrogen atmosphere.

Step 6'

In step 6', compound (7-2) is produced by subjecting compound (6) wherein R is a fluorine atom (i.e., compound (6-B)) to a cyclization reaction. A base may be added to the reaction system.

Examples of the base include sodium carbonate, potassium carbonate, sodium hydroxide, potassium hydroxide, potassium tert-butoxide, sodium hydride, potassium hydride, 1,8-diazabicyclo[5.4.0]-7-undecene and the like, with preference given to potassium carbonate.

The amount of the base to be used is generally 0.5 to 10 mol, preferably 0.5 to 2 mol, particularly preferably 0.5 to 1 mol, per 1 mol of compound (6-B).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to N,N-dimethylformamide (DMF).

The reaction temperature is generally 20° C. to 100° C., preferably 30° C. to 80° C., more preferably 30° C. to 60° C.

The reaction time is generally 1 hr to 24 hr, preferably 4 hr to 16 hr, more preferably 4 hr to 12 hr.

The obtained compound (7-2) can be purified by recrystallization. Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ketone solvents such as acetone, methylethylketone, methylisobutylketone and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to a mixed solvent of ethanol and water, toluene, or a mixed solvent of toluene and heptane.

Step 7'

Compound (8) can be obtained by introducing a protecting group into the hydroxyl group of compound (7-2) in a solvent according to a conventional method.

For example, when the hydroxyl-protecting group is a tert-butyldimethylsilyl group, compound (8) can be obtained by adding a base and tert-butyldimethylsilyl chloride to compound (7-2) in a solvent.

The amount of tert-butyldimethylsilyl chloride to be used is generally 1 to 10 mol, preferably 1 to 2 mol, particularly preferably 1 to 1.3 mol, per 1 mol of compound (7-2).

Examples of the base include triethylamine, diisopropylethylamine, pyridine, imidazole and the like, with preference given to imidazole.

The amount of the base to be used is generally 1 to 10 mol, preferably 1 to 2 mol, particularly preferably 1 to 1.3 mol, per 1 mol of compound (7-2).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile, water and the like or a mixed solvent thereof and the like, more preferably toluene.

The reaction temperature is generally 0° C. to 100° C., preferably 15° C. to 80° C., more preferably 50° C. to 80° C.

The reaction time is generally 1 hr to 24 hr, preferably 1 hr to 10 hr, more preferably 1 hr to 5 hr.

The reaction is preferably carried out under argon atmosphere or under nitrogen atmosphere, particularly preferably under nitrogen atmosphere.

For production of compound (8), of the production methods described in step 5, a compound wherein the hydroxyl group of compound (5-1) is protected by the above-defined "hydroxyl-protecting group" is reacted, instead of compound (5-1), in the same manner as in compound (5-B), and a compound which is the obtained compound (6-B) wherein the hydroxyl group is protected by the above-defined "hydroxyl-protecting group" is reacted in the same manner as in step 6'.

Compound (5-1) protected by a hydroxyl-protecting group can be separately synthesized according to a known technique. Examples of compound (5-1) protected by a hydroxyl-protecting group include (S)-1-(tert-butyldimethylsilanyloxymethyl)-2-methylpropylamine, (S)-2-methyl-1-(trimethylsilanyloxymethyl)propylamine, (S)-2-methyl-1-(tetrahydropyran-2-yloxymethyl)propylamine, methyl 2-amino-3-methylbutylcarbonate and ethyl 2-amino-3-methylbutylcarbonate, preferably (S)-1-(tert-butyldimethylsilanyloxymethyl)-2-methylpropylamine, (S)-2-methyl-1-(tetrahydropyran-2-yloxymethyl)propylamine and methyl 2-amino-3-methylbutylcarbonate, particularly preferably (S)-1-(tert-butyldimethylsilanyloxymethyl)-2-methylpropylamine.

The optical purity of compound (5-1) protected by a hydroxyl-protecting group is not less than 95% ee, preferably not less than 97 ee, more preferably not less than 99% ee.

The amount of compound (5-1) protected by a hydroxyl-protecting group to be used, is generally 1 to 10 mol, preferably 1 to 2 mol, particularly preferably 1.1 to 1.3 mol, per 1 mol of compound (5-B).

Step 8

Compound (9) can be obtained by reacting compound (8) with a compound represented by the formula (8-1) (hereinafter to be sometimes abbreviated as compound (8-1)) in a solvent in the presence of a catalyst and in the presence of a ligand as necessary.

Compound (8-1) can be separately synthesized according to Reference Examples 1 and 2 or a known technique.

Specifically, compound (8-1) represented by the formula (8-1) can be obtained by reacting, in advance, the metal atom with a halide and an alkylsilyl compound in a solvent, and reacting the reaction mixture with a solution of substituted benzyl halide.

Examples of the substituted benzyl halide include a compound having the following formula:

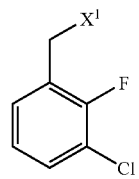

wherein $X^1$ is a halogen atom (e.g., fluorine atom, chlorine atom, bromine atom and iodine atom).

The substituted benzyl halide may be a commercially available product, or can be separately synthesized according to a known technique. It is preferably 3-chloro-2-fluorobenzyl chloride or 3-chloro-2-fluorobenzyl bromide.

Examples of the metal atom include a zinc atom and the like, preferably metal zinc.

The metal atom is generally 1 to 5 mol, preferably 1 to 1.5 mol, per 1 mol of the substituted benzyl halide.

Examples of the halide include 1,2-dibromoethane and the like, preferably 1,2-dibromoethane.

The amount of the halide to be used is 0.01 to 0.1 mol, preferably 0.01 to 0.02 mol, per 1 mol of the substituted benzyl halide.

Examples of the alkylsilyl compound include trimethylsilyl chloride and the like, preferably trimethylsilyl chloride.

The amount of the alkylsilyl compound to be used is 0.01 to 0.1 mol, preferably 0.01 to 0.05 mol, per 1 mol of the substituted benzyl halide.

Examples of the solvent include ether solvents such as 1,4-dioxane, diethyl ether, 1,2-dimethoxyethane, tetrahydrofuran (THF) and the like; hydrocarbon solvents such as toluene, hexane, etc. and the like. Preferable solvent is an ether solvent, particularly preferably THF.

The reaction temperature is generally 0° C. to 100° C., particularly preferably 20° C. to 65° C.

The reaction time is generally 1 hr to 24 hr, preferably 1 hr to 12 hr, particularly preferably 3 hr to 8 hr.

The reaction is preferably carried out under argon atmosphere or under nitrogen atmosphere, particularly preferably under nitrogen atmosphere.

Preferable examples of compound (8-1) include 3-chloro-2-fluorobenzylzinc bromide, 3-chloro-2-fluorobenzylzinc chloride and a tetrahydrofuran solution thereof.

The amount of compound (8-1) to be used is generally 1 to 5 mol, preferably 1 to 2 mol, per 1 mol of compound (8).

Examples of the catalyst include palladium catalysts such as bis(dibenzylideneacetone)palladium, tris(dibenzylideneacetone)dipalladium, dichlorobis(triphenylphosphine)palladium, dichlorobis(benzonitrile)palladium, dichloroethylenediaminepalladium, palladium acetate, palladium chloride, tetrakis(triphenylphosphine)palladium, bis(triphenylphosphine)palladium(II)dichloride, palladium-carbon and the like, nickel catalyst and the like. Of these, tris(dibenzylideneacetone)dipalladium is preferable.

Examples of the ligand include triphenylphosphine, tri(2-tolyl)phosphine, tri(2-furyl)phosphine and the like, preferably triphenylphosphine.

The amount of each of the ligand and the catalyst to be used is generally 0.01 to 0.1 mol, preferably 0.02 to 0.07 mol, particularly preferably 0.02 to 0.06 mol, per 1 mol of compound (8).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogen solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as 1-methyl-2-pyrrolidinone, N,N-dimethylformamide (DMF), N,N-dimethylacetamide (DMA), dimethyl sulfoxide, acetonitrile and the like or a mixed solvent thereof and the like, preferably ether solvent, polar solvent or a mixed solvent thereof, more preferably, tetrahydrofuran, 1-methyl-2-pyrrolidinone or a mixed solvent thereof.

The reaction temperature is generally 0° C. to 100° C., preferably 40° C. to 80° C., more preferably 50° C. to 70° C.

The reaction time is generally 1 hr to 24 hr, preferably 1 hr to 10 hr, more preferably 2 hr to 6 hr.

The reaction is preferably carried out under argon atmosphere or under nitrogen atmosphere, particularly preferably under nitrogen atmosphere.

When the catalyst used is to be removed, the reaction mixture is preferably treated with a base such as ammonium chloride, sodium hydroxide, potassium hydroxide, lithium hydroxide, diethylenetriamine, ethylenediamine and the like, particularly preferably an aqueous ammonium chloride solution or aqueous ethylenediamine solution.

Step 9

Compound (10) or a salt thereof can be obtained by subjecting compound (9) to hydrolysis in a solvent under a basic condition (e.g., in the presence of a base such as sodium hydroxide, potassium hydroxide, lithium hydroxide and the like) or under an acidic condition (e.g., in the presence of an acid such as hydrochloric acid, sulfuric acid and the like).

The amount of the base to be used is generally 1 to 10 mol, preferably 1 to 5 mol, particularly preferably 1 to 2 mol, per 1 mol of compound (9).

The amount of the acid to be used is not particularly limited.

The reaction condition is preferably a basic condition, and the reaction is more preferably carried out in the presence of sodium hydroxide, particularly preferably using an aqueous sodium hydroxide solution.

Examples of the solvent include hydrocarbon solvents such as toluene, xylene, hexane, heptane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to a mixed solvent of isopropanol and water.

The reaction temperature is generally 0° C. to 150° C., preferably 15° C. to 100° C., more preferably 65° C. to 75° C.

The reaction time is generally 1 hr to 24 hr, preferably 1 hr to 12 hr, more preferably 1 hr to 8 hr.

For the workup, a treatment with an activated carbon or extraction operation can be carried out for the purpose of purifying compound (10). For example, when the reaction condition is a basic condition, the activated carbon treatment can be carried out without any limitation on the amount of the activated carbon to be used. Moreover, when hydrochloric acid and the like are used for an extraction operation, the amount thereof to be used is generally 1 to 10 mol, preferably 1 to 5 mol, particularly preferably 1 to 2 mol, per 1 mol of compound (9).

Examples of the solvent used in the extraction operation include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ketone solvents such as acetone, methylethylketone, methylisobutylketone, methylisopropylketone and the like; ether solvents such as 1,4-dioxane, diethyl ether, 1,2-dimethoxyethane, tetrahydrofuran, anisole and the like; polar solvents such as acetonitrile and the like or a mixed solvent thereof and the like, with preference given to toluene, heptane, methyl acetate, ethyl acetate, propyl acetate, isopropyl acetate, butyl acetate, isobutyl acetate, acetone, methylethylketone, methylisobutylketone, methylisopropylketone and anisole. When methylisopropylketone is used to remove impurity such as 1,1'-bis-((S)-1-hydroxymethyl-2-methylpropyl)-7,7'-dimethoxy-4,4'-dioxo-1,4,1',4'-tetrahydro-[6,6']biquinolinyl-3,3'-dicarboxylic acid, 1-((S)-1-hydroxymethyl-2-methylpropyl)-7-methoxy-4-oxo-1,4-dihydroquinoline-3-carboxylic acid and the like, the content of the aforementioned impurity and the like can be reduced to not more than 0.2%, preferably 0.1% to 0.2%, more preferably not more than 0.1%, relative to compound (10). Thus, heptane and methylisopropylketone are particularly preferable.

The obtained compound (10) can be purified by recrystallization. Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ketone solvents such as acetone, methylethylketone, methylisobutylketone and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to a mixed solvent of ethanol and water, and toluene.

EXAMPLES

A compound useful as a synthetic intermediate for an anti-HIV agent having an integrase inhibitory activity and a production method thereof, and a production method of an anti-HIV agent using the synthetic intermediate are specifically explained below. Those of ordinary skill in the art will understand that the present invention is not limited to these Examples.

Reference Example 1

Synthesis of 3-chloro-2-fluorobenzylzinc bromide

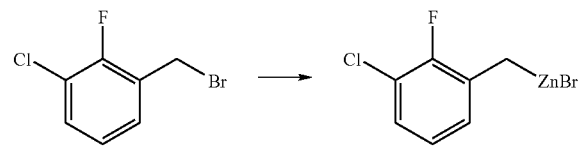

Under an argon atmosphere, a zinc powder (3.18 g) was suspended in tetrahydrofuran (8 ml), 1,2-dibromoethane (0.061 g, 0.32 mmol) and trimethylsilyl chloride (0.071 g, 0.65 mmol) were successively added at 60° C., and the mixture was stirred for 30 min. A solution of 3-chloro-2-fluorobenzyl bromide (7.48 g, 32.5 mmol) in tetrahydrofuran (20 ml) was added dropwise at 60° C. to the solution prepared above. The mixture was further stirred for 1 hr to give a solution of 3-chloro-2-fluorobenzylzinc bromide in tetrahydrofuran.

Reference Example 2

Synthesis of 3-chloro-2-fluorobenzylzinc chloride

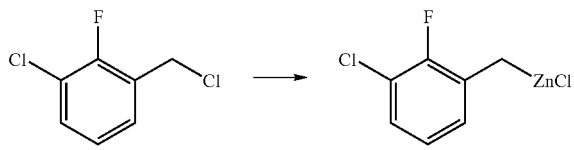

Under an argon atmosphere, a zinc powder (1.44 g) was suspended in tetrahydrofuran (3.6 ml), 1,2-dibromoethane (38 mg) and trimethylsilyl chloride (43 mg) were successively added at 60° C., and the mixture was stirred for 30 min. A solution of 3-chloro-2-fluorobenzyl chloride (3.58 g) in tetrahydrofuran (9 ml) was added dropwise at 60° C. to the solution prepared above. The mixture was further stirred under heating for 1 hr to give a solution of 3-chloro-2-fluorobenzylzinc chloride in tetrahydrofuran.

Example 1

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid Step 1

Synthesis of 5-bromo-2,4-dimethoxybenzoic acid

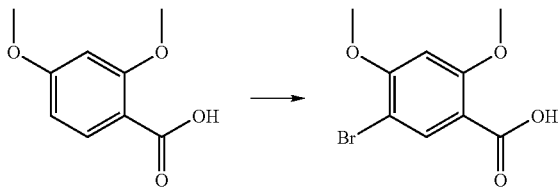

2,4-Dimethoxybenzoic acid (30.0 g) was suspended in acetic acid (180 mL). A bromine (27.6 g)/acetic acid (60 mL) solution was slowly added dropwise to the suspension and, after completion of the dropwise addition, the mixture was stirred at 25° C. for 2 hrs, and the termination of the reaction was confirmed by HPLC. An aqueous solution of sodium sulfite (2.10 g) and water (360 mL) was added dropwise to the reaction mixture. After completion of the dropwise addition, the mixture was stirred at 25° C. for 1 hr. Precipitated crystals were collected by filtration, washed 4 times with water (150 mL), and vacuum dried to give 5-bromo-2,4-dimethoxybenzoic acid as white crystals (41.2 g, 96%).

Step 2

Synthesis of 5-bromo-2,4-dimethoxybenzoic acid chloride

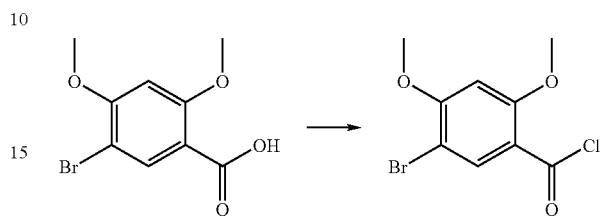

Under a nitrogen atmosphere, 5-bromo-2,4-dimethoxybenzoic acid (40.0 g) was suspended in toluene solution (DMF concentration: 300 ppm, 200 mL). To the suspension was added dropwise thionyl chloride (21.9 g) at 75° C. After stirring at 75° C. for 1 hr, completion of the reaction was confirmed by HPLC. Toluene and excess thionyl chloride were evaporated under reduced pressure. Toluene (100 mL) was added to the concentrated residue, and the mixture was concentrated again under reduced pressure. THF (100 mL) was added to the obtained 5-bromo-2,4-dimethoxybenzoic acid chloride, which was directly used in the next step.

Step 3

Synthesis of ethyl 3-(5-bromo-2,4-dimethoxyphenyl)-3-oxopropionate

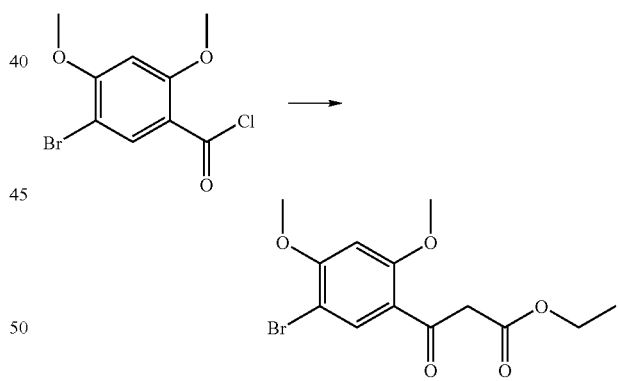

Under a nitrogen atmosphere, to a suspension of anhydrous magnesium chloride (36.5 g) and ethyl acetate (200 mL) was slowly added dropwise tetrahydrofuran (55.2 g). After completion of the dropwise addition, the mixture was stirred at 75° C. for 2 hr to dissolve anhydrous magnesium chloride. The solution was added dropwise to an ice-cold suspension of potassium ethylmalonate (52.1 g) and triethylamine (46.5 g) in ethyl acetate (200 mL). After the dropwise addition, the suspension was warmed to 70° C. To the suspension was slowly added dropwise at 70° C. a suspension of 5-bromo-2,4-dimethoxybenzoic acid chloride obtained in Step 2 of Example 1 in tetrahydrofuran. After completion of the dropwise addition, the mixture was stirred at 70° C. for 0.5 hr, and the completion of the reaction was confirmed by HPLC. 2N Hydrochloric acid (240 mL) was added dropwise to the reaction mixture under ice-cooling, and the mixture was stirred at room temperature for 1 hr. The organic layer was separated, and washed successively with water (200 mL), twice with 5% sodium hydrogencarbonate (200 mL), and water (200 mL). After washing, the solvent was evaporated under reduced pressure, toluene (200 mL) was added to the concentrated residue, and the mixture was concentrated again under reduced pressure. The obtained ethyl 3-(5-bromo-2,4-dimethoxyphenyl)-3-oxopropionate (52.8 g) as a white solid was directly used in the next step.

Step 4

Synthesis of ethyl 2-(5-bromo-2,4-dimethoxybenzoyl)-3-dimethylaminoacrylate

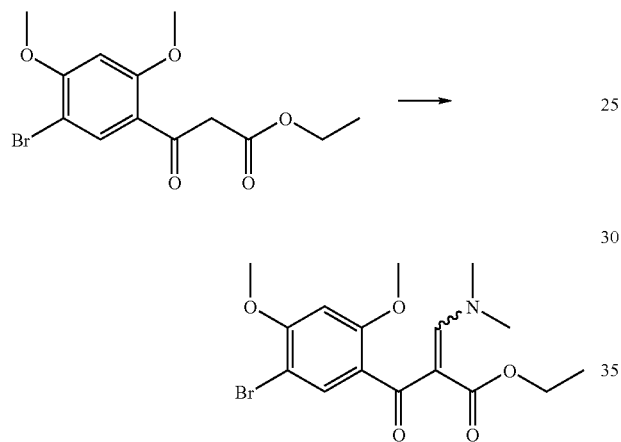

Under a nitrogen atmosphere, ethyl 3-(5-bromo-2,4-dimethoxyphenyl)-3-oxopropionate (52.8 g) obtained in Step 3 of Example 1 and N,N-dimethylformamide dimethyl acetal (44.6 g) were dissolved in toluene. The solution was stirred at 95° C. for 16 hr, and the completion of the reaction was confirmed by HPLC. The reaction mixture was cooled to room temperature to give a solution of ethyl 2-(5-bromo-2,4-dimethoxybenzoyl)-3-dimethylaminoacrylate in toluene. The reaction mixture was directly used in the next step.

Step 5

Synthesis of ethyl 2-(5-bromo-2,4-dimethoxybenzoyl)-3-((S)-1-hydroxymethyl-2-methylpropylamino)acrylate

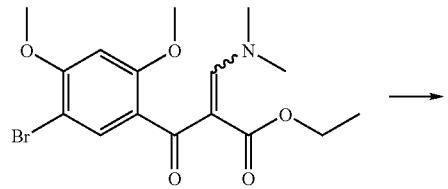

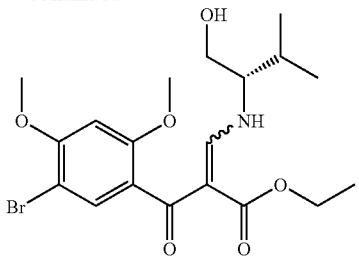

Under a nitrogen atmosphere, to a solution of ethyl 2-(5-bromo-2,4-dimethoxybenzoyl)-3-dimethylaminoacrylate obtained in Step 4 of Example 1 in toluene was added L-valinol (20.6 g). After stirring at room temperature for 1 hr, the completion of the reaction was confirmed by HPLC. 1 mol/L Hydrochloric acid (200 mL) was added to the reaction mixture, and after stirring, the toluene layer was separated. The toluene layer was further washed successively with 1 mol/L hydrochloric acid (200 mL), water (200 mL), 5% aqueous sodium hydrogencarbonate solution (200 mL) and water (200 mL). After washing, toluene was evaporated under reduced pressure, toluene (200 mL) was added to the concentrated residue, and the mixture was concentrated again under reduced pressure. THF (200 mL) was further added to the concentrated residue, and the mixture was concentrated again under reduced pressure. THF (160 mL) was added to the obtained concentrated residue to give ethyl 2-(5-bromo-2,4-dimethoxybenzoyl)-3-((S)-1-hydroxymethyl-2-methylpropylamino)acrylate as a tetrahydrofuran solution. The solution was directly used in the next step.

Step 6

Synthesis of ethyl 2-(5-bromo-2,4-dimethoxybenzoyl)-3-((S)-1-(tert-butyldimethyl-silanyloxymethyl)-2-methylpropylamino)acrylate

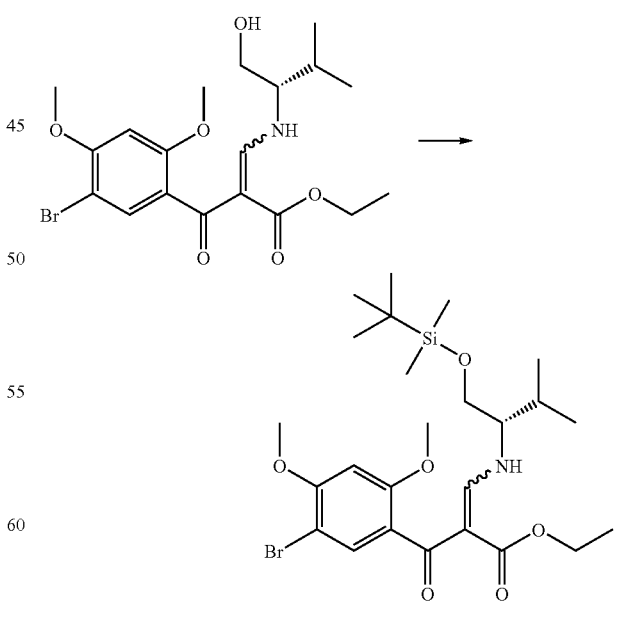

To a solution of ethyl 2-(5-bromo-2,4-dimethoxybenzoyl)-3-((S)-1-hydroxymethyl-2-methylpropylamino)acrylate obtained in Step 5 of Example 1 in tetrahydrofuran was added imidazole (13.6 g) under a nitrogen atmosphere. To the solution was added at 50-70° C. a 50% toluene solution (50.1 g) of tert-butyldimethylsilyl chloride. After completion of the dropwise addition, the mixture was stirred at 50-70° C. for 2 hr, and the completion of the reaction was confirmed by HPLC. The reaction mixture was cooled, and 1N-HCl (200 mL) was added. After the addition, the mixture was stirred at room temperature for 1 hr, and the organic layer was separated. The organic layer was washed successively with 1N-HCl (200 mL), 5% NaHCO$_3$ (200 mL), water (200 mL), and 10% brine (200 mL). After washing, tetrahydrofuran was evaporated under reduced pressure, toluene (200 mL) was added to the concentrated residue, and the mixture was again concentrated under reduced pressure. Ethanol (200 mL) was further added to the concentrated residue, and the mixture was concentrated again under reduced pressure to give crude ethyl 2-(5-bromo-2,4-dimethoxybenzoyl)-3-((S)-1-(tert-butyldimethyl-silanyloxymethyl)-2-methylpropylamino)acrylate as a solid.

The crude product was recrystallized from a mixed solution of ethanol (180 mL) and water (360 mL) to give ethyl 2-(5-bromo-2,4-dimethoxybenzoyl)-3-((S)-1-(tert-butyldimethyl-silanyloxymethyl)-2-methylpropylamino)acrylate (70.6 g, yield 83%, from 5-bromo-2,4-dimethoxybenzoic acid obtained in Step 1) as purified crystals.

Step 7

Synthesis of ethyl 6-bromo-1-((S)-1-(tert-butyldimethyl-silanyloxymethyl)-2-methylpropyl)-7-methoxy-4-oxo-1,4-dihydroquinoline-3-carboxylate

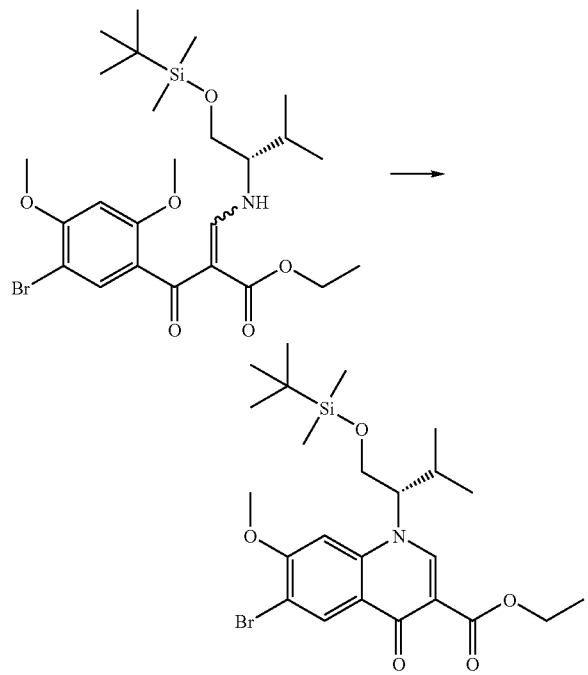

Under a nitrogen atmosphere, ethyl 2-(5-bromo-2,4-dimethoxybenzoyl)-3-((S)-1-(tert-butyldimethyl-silanyloxymethyl)-2-methylpropylamino)acrylate (5.0 g) was added to toluene (30 mL), and potassium carbonate (1.24 g) and tetra-n-butylphosphoniumbromide (1.52 g) were added. After stirring at 110° C. for 11 hr, the completion of the reaction was confirmed by HPLC. After cooling the reaction mixture, tetrahydrofuran (40 mL) and 10% brine (40 mL) were added, and the toluene layer was separated. The toluene layer was washed twice with 10% brine (40 mL). After washing, toluene was evaporated under reduced pressure to give crude ethyl 6-bromo-1-((S)-1-(tert-butyldimethyl-silanyloxymethyl)-2-methylpropyl)-7-methoxy-4-oxo-1,4-dihydroquinoline-3-carboxylate.

The crude product was recrystallized from toluene (40 mL) to give ethyl 6-bromo-1-((S)-1-(tert-butyldimethyl-silanyloxymethyl)-2-methylpropyl)-7-methoxy-4-oxo-1,4-dihydroquinoline-3-carboxylate (3.53 g, yield: 75%) as purified crystals.

Step 8

Synthesis of ethyl 1-((S)-1-(tert-butyldimethyl-silanyloxymethyl)-2-methylpropyl)-6-(3-chloro-2-fluorobenzyl)-7-methoxy-4-oxo-1,4-dihydroquinoline-3-carboxylate

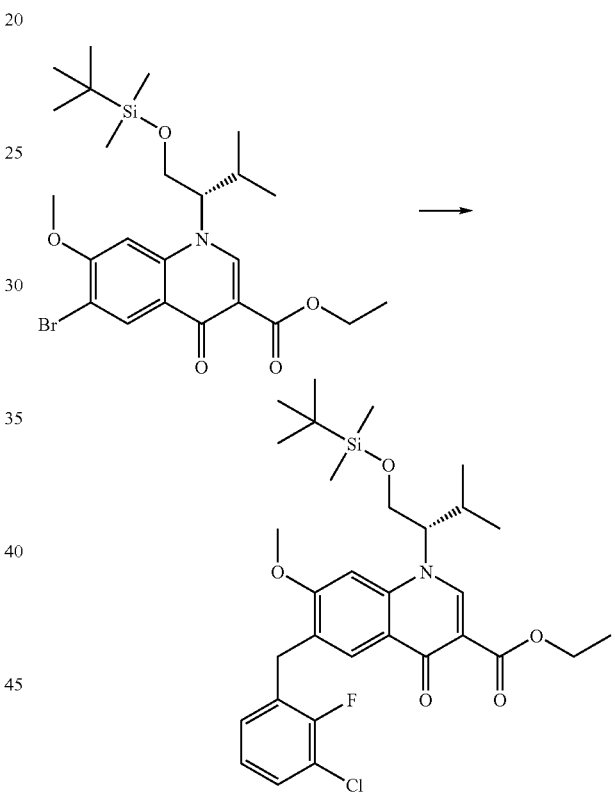

Under a nitrogen atmosphere, tris(dibenzylideneacetone)dipalladium(0) (332 mg) and triphenylphosphine (299 mg) were added to tetrahydrofuran (40 mL), and the mixture was stirred at room temperature for 1 hr. Ethyl 6-bromo-1-((S)-1-(tert-butyldimethyl-silanyloxymethyl)-2-methylpropyl)-7-methoxy-4-oxo-1,4-dihydroquinoline-3-carboxylate (10.0 g) obtained in Step 7 of Example 1/1-methyl-2-pyrrolidinone (80 mL) solution and a solution (26.2 g) of 29% 3-chloro-2-fluorobenzylzinc bromide in tetrahydrofuran were successively added dropwise at room temperature. After completion of the dropwise addition, the mixture was stirred at 65° C. for 3 hr, and the completion of the reaction was confirmed by HPLC. After cooling the reaction mixture, toluene (50 mL) and 12.5% aqueous ammonium chloride solution (100 mL) were added, sufficiently stirring, and the aqueous layer was discarded. The organic layer was washed successively with 25% aqueous ammonium chloride solution (50 mL), twice with 2% aqueous ethylenediamine solution (50 mL), and with 10% aqueous sodium chloride solution (50 mL). After washing, the solvent was evaporated under reduced pressure. Isopropanol (50 mL) was added to the concentrated residue to give a solution of ethyl 1-((S)-1-(tert-butyldimethyl-silanyloxymethyl)-2-methylpropyl)-6-(3-chloro-2-fluorobenzyl)-7-methoxy-4-oxo-1,4-dihydroquinoline-3-carboxylate in isopropanol. This was directly used in the next step.

Step 9

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid

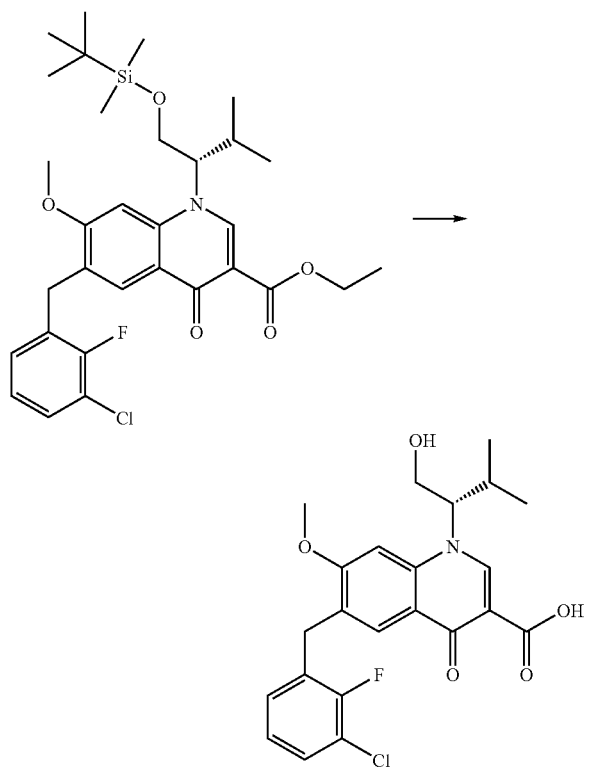

To a solution of ethyl 1-((S)-1-(tert-butyldimethyl-silanyloxymethyl)-2-methylpropyl)-6-(3-chloro-2-fluorobenzyl)-7-methoxy-4-oxo-1,4-dihydroquinoline-3-carboxylate obtained in Step 8 of Example 1 in isopropanol was added 1 mol/L aqueous sodium hydroxide solution (40 mL). After stirring at 70° C. for 5 hr, the completion of the reaction was confirmed by HPLC. After cooling to room temperature, activated carbon (Sirasagi A, 1.0 g) was added to the reaction mixture. After stirring, the mixture was filtered through powder cellulose (KC FLOCK). The reaction vessel and the filter were washed with isopropanol (10 mL)/water (10 mL) solution, and the lavage fluid was combined with the filtrate. Water (40 mL) and heptane (50 mL) were added to the obtained filtrate, and after stirring, the organic layer was removed. The aqueous layer was washed again with heptane (50 mL). The aqueous layer was ice-cooled, and methylisopropylketone (100 mL) was added while adding concentrated hydrochloric acid (4.17 g) dropwise at 10° C. After the addition, the mixture was stirred at room temperature, and the aqueous layer was discarded. The organic layer was washed successively with 8.5% aqueous sodium hydrogencarbonate solution (50 mL, twice), sodium chloride (2.5 g)/0.5 mol/L hydrochloric acid (50 mL) solution, and 10% brine (50 mL). After washing, the solvent was evaporated under reduced pressure, toluene (30 mL) was added to the obtained concentrated residue, and the mixture was concentrated again under reduced pressure to give crude 6-(3-chloro-2-fluorobenzyl)-1-((S)-1-hydroxymethyl-2-methylpropyl)-7-methoxy-4-oxo-1,4-dihydroquinoline)-3-carboxylic acid (9.46 g). The crude product was recrystallized from toluene (50 mL) to give 6-(3-chloro-2-fluorobenzyl)-1-((S)-1-hydroxymethyl-2-methylpropyl)-7-methoxy-4-oxo-1,4-dihydroquinoline)-3-carboxylic acid as purified white crystals (7.26 g, 85%).

The obtained purified 6-(3-chloro-2-fluorobenzyl)-1-((S)-1-hydroxymethyl-2-methylpropyl)-7-methoxy-4-oxo-1,4-dihydroquinoline)-3-carboxylic acid (4.00 g) was recrystallized from ethanol (30 mL)/water (20 mL) to give a product of 6-(3-chloro-2-fluorobenzyl)-1-((S)-1-hydroxymethyl-2-methylpropyl)-7-methoxy-4-oxo-1,4-dihydroquinoline)-3-carboxylic acid (3.74 g, 94%).

The compound obtained in Step 9 of Example 1 was identified as compound (10).

TABLE 1

| Structural formula | $^1$H-NMR | MS (ESI) M+ |
|---|---|---|
| (10) | (DMSO-$d_6$, 400 MHz) δ (ppm): 0.73(d, 3H, J = 6.7 Hz), 1.16(d, 3H, J = 6.7 Hz), 2.30-2.55(m, 1H), 3.75-3.85(m, 1H), 4.00-4.10(m, 1H), 4.04(s, 3H), 4.12 (s, 2H), 4.80-4.95(m, 1H), 5.15-5.25(m, 1H), 7.10-7.20(m, 1H), 7.20-7.25(m, 1H), 7.40-7.55 (m, 2H), 8.10(s, 1H), 8.94(s, 1H), 15.5(s, 1H). | 448 |

The property data of the title compound in each step is as follows.

TABLE 2

| Structural formula | ¹H-NMR | MS (ESI) M+ |
|---|---|---|
| (Step 1) | (DMSO-$d_6$, 300 MHz) δ (ppm): 3.88(s, 3H), 3.95(s, 3H), 6.78(s, 1H), 7.86(s, 1H), 12.47(s, 1H). | 261 |
| (Step 3) | (DMSO-$d_6$, 300 MHz) δ (ppm): 1.18(t, 3H, J = 7.3 Hz), 3.85(s, 2H), 3.87(s, 3H), 3.96(s, 3H), 4.12(q, 2H, J = 7.3 Hz), 6.84(s, 1H), 7.88(s, 1H). | 331 |
| (Step 5) | (DMSO-$d_6$, 300 MHz) δ (ppm): 0.82-1.00(m, 9H), 1.85-1.97(m, 1H), 3.20-3.42(m, 1H), 3.47-3.65(m, 2H), 3.85(s, 3H), 3.90-3.99(m, 1H), 3.89(s, 3H), 4.95-5.00(m, 1H), 6.70(s, 1H), 7.27(s, 1H), 7.98(d, 1H, J = 13.9 Hz), 10.67-10.75(m, 1H). | |
| (Step 6) | (DMSO-$d_6$, 400 MHz) δ (ppm): 0.01-0.03(m, 6H), 0.92-1.00(m, 10H), 0.93(s, 9H), 1.82-1.99(m, 1H), 3.25-3.40(m, 1H), 3.65-3.80(m, 1H), 3.72(s, 3H), 3.80-3.91(m, 2H), 3.91(s, 3H), 6.68(s, 1H), 7.24(s, 1H), 7.97(d, 1H, J = 13.6 Hz), 10.60-10.73(m, 1H). | 558 |

TABLE 2-continued

| Structural formula | ¹H-NMR | MS (ESI) M+ |
|---|---|---|
| 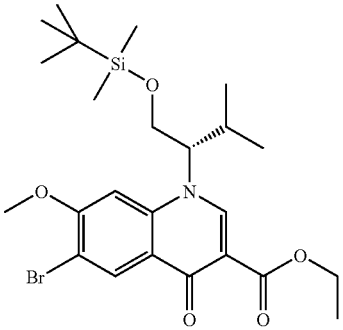<br>(Step 7) | (DMSO-$d_6$, 400 MHz) δ (ppm): 0.00(d, 6H, J = 4.8 Hz), 0.82(s, 9H), 0.85(d, 3H, J = 6.6 Hz), 1.24(d, 3H, J = 6.2 Hz), 1.34(t, 3H, J = 7.3 Hz), 2.40-2.48(m, 1H), 3.90-3.98(m, 1H), 4.12(s, 3H), 4.12-4.17(m, 1H), 4.23-4.34(m, 2H), 4.80-4.87(m, 1H), 7.47(s, 1H), 8.43(s, 1H), 8.70(s, 1H). | 526 |

The analysis conditions of HPLC used in the above-mentioned Example 1 are described in the following.
HPLC Analysis Conditions
Analysis Method 1 (Example 1, Step 1, Step 2 and Step 6)
Analysis Conditions
   column: AM-302 5 μm (150 mm×4.6 mm i.d.) (YMC)
   column temperature: 40° C.
   mobile phase: mobile phase A: 0.01% aqueous TFA (trifluoroacetic acid) solution
   mobile phase B: 0.01% TFA acetonitrile solution
Gradient Program

TABLE 3

| | time (min) | | | | | | | | |
|---|---|---|---|---|---|---|---|---|---|
| | 0 | 5 | 15 | 20 | 35 | 45 | 55 | 56 | 65 |
| mobile phase A | 70 | 70 | 50 | 50 | 30 | 20 | 20 | 70 | stopped |
| mobile phase B | 30 | 30 | 50 | 50 | 70 | 80 | 80 | 30 | | flow rate: 1.0 mL/min
   detection: UV 220 nm
   analysis time: 55 min
Analysis Method 2 (Example 1, Step 3, Step 4 and Step 5)
Analysis Conditions
   column: AM-302 5 μm (150 mm×4.6 mm i.d., YMC)
   column temperature: 40° C.
   mobile phase: mobile phase A: 0.01% TFA aqueous solution
   mobile phase B: 0.01% TFA acetonitrile solution
Gradient Program

TABLE 4

| | time (min) | | | | | |
|---|---|---|---|---|---|---|
| | 0 | 15 | 20 | 35 | 45 | 46 | 55 |
| mobile phase A | 55 | 55 | 50 | 30 | 30 | 55 | stopped |
| mobile phase B | 45 | 45 | 50 | 70 | 70 | 45 | | flow rate: 1.0 mL/min
   detection: UV 220 nm
   analysis time: 55 min

Analysis Method 3 (Example 1, Step 7)
Analysis Conditions
   column: Inertsil ODS-80A 5 μm (150 mm×4.6 mm i.d.) (GL Sciences Inc)
   column temperature: 40° C.
   mobile phase: mobile phase A: 0.01% aqueous TFA solution
   mobile phase B: 0.01% TFA acetonitrile solution
Gradient Program

TABLE 5

| | time (min) | | | | | | | | |
|---|---|---|---|---|---|---|---|---|---|
| | 0 | 5 | 15 | 20 | 35 | 45 | 55 | 56 | 65 |
| mobile phase A | 70 | 70 | 50 | 50 | 30 | 20 | 20 | 70 | stopped |
| mobile phase B | 30 | 30 | 50 | 50 | 70 | 80 | 80 | 30 | | flow rate: 1.0 mL/min
   detection: UV 220 nm
   analysis time: 55 min
Analysis Method 4 (Example 1, Step 9)
Analysis Conditions
   column: Inertsil ODS-80A 5 μm (150 mm×4.6 mm i.d.) (GL Sciences Inc)
   column temperature: 40° C.
   mobile phase: mobile phase A: 10 mM phosphate buffer (pH 6.9)
   mobile phase B: acetonitrile (HPLC grade)
Gradient Program

TABLE 6

| | time (min) | | | | | |
|---|---|---|---|---|---|---|
| | 0 | 8 | 25 | 50 | 51 | 60 |
| mobile phase A | 55 | 55 | 20 | 20 | 55 | stopped |
| mobile phase B | 45 | 45 | 80 | 80 | 45 | | flow rate: 1.0 mL/min
   detection: UV 220 nm
   analysis time: 55 min

Analysis Method 5 (Example 1, Step 8)

Analysis Conditions column: Inertsil ODS-80A 5 μm (150 mm×4.6 mm i.d.) (GL Sciences Inc)

column temperature: 40° C.

mobile phase: mobile phase A: 10 mM phosphate buffer (pH 6.9)

mobile phase B: acetonitrile (HPLC grade)

Gradient Program

TABLE 7

| | time (min) | | | | | | |
|---|---|---|---|---|---|---|---|
| | 0 | 6 | 8 | 28 | 35 | 55 | 56 | 60 |
| mobile phase A | 50 | 50 | 40 | 40 | 20 | 20 | 50 | stopped |
| mobile phase B | 50 | 50 | 60 | 60 | 80 | 80 | 50 | | flow rate: 1.0 mL/min detection: UV 220 nm analysis time: 65 min

Example 2

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid Step 1

Synthesis of 5-bromo-2-fluoro-4-methoxybenzoic acid

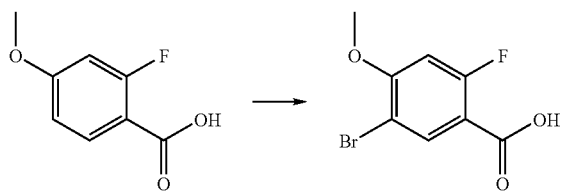

2-Fluoro-4-methoxybenzoic acid (10.0 g) was suspended in acetic acid (80 mL). To the suspension was slowly added dropwise bromine (20.7 g)/acetic acid (20 mL) solution. After completion of the dropwise addition, the mixture was stirred at 25° C. for 3 hr and further at 60° C. for 4 hr, the completion of the reaction was confirmed by HPLC. After cooling to room temperature, to the suspension was added dropwise an aqueous solution of sodium sulfite (9.63 g) and water (100 mL). After completion of the dropwise addition, the mixture was stirred at 25° C. for 2 hr, and then for 2 hr under ice-cooling. The precipitated crystals were collected by filtration, washed four times with water (30 mL), and vacuum dried to give 5-bromo-2-fluoro-4-methoxybenzoic acid as white crystals (14.5 g, 99%).

Step 2

Synthesis of 5-bromo-2-fluoro-4-methoxybenzoic acid chloride

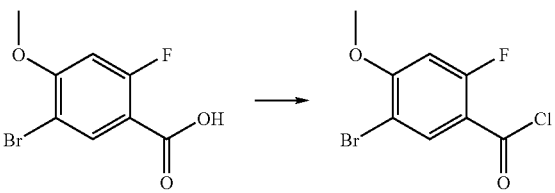

Under a nitrogen atmosphere, 5-bromo-2-fluoro-4-methoxybenzoic acid (10.0 g) was suspended in DMF/toluene solution (50 mL) (DMF concentration: 300 ppm). To the suspension was added dropwise thionyl chloride (5.73 g) at 70° C. After stirring at 70° C. for 2 hr, the completion of the reaction was confirmed by HPLC. Toluene and excess thionyl chloride were evaporated under reduced pressure. To the concentrated residue was added toluene (30 mL), and the mixture was concentrated again under reduced pressure. To the obtained acid chloride (5-bromo-2-fluoro-4-methoxybenzoic acid chloride) was added toluene (30 mL), and the mixture was directly used in the next step.

Step 3

Synthesis of ethyl 3-(5-bromo-2-fluoro-4-methoxyphenyl)-3-oxopropionate

Under a nitrogen atmosphere, potassium ethylmalonate (13.7 g) and triethylamine (12.2 g) were suspended in THF (100 mL). Furthermore, anhydrous magnesium chloride (9.56 g) was added by portions while paying attention to heat generation. The suspension was stirred at 60° C. for 1.5 hr, and to the suspension was slowly added dropwise at 60° C. a suspension of acid chloride obtained in the above-mentioned Step 2 in toluene. After completion of the dropwise addition, the mixture was stirred at 60° C. for 2 hr. The completion of the reaction was confirmed by HPLC, and the mixture was cooled to room temperature. Toluene (50 mL) was added to the reaction mixture, and 2N hydrochloric acid (60 mL) was added. After dropwise addition, the mixture was stirred at room temperature for 1 hr. The organic layer was separated, and washed successively with water (50 mL), twice with 5% sodium hydrogencarbonate (50 mL), and water (50 mL). After washing, the solvent was evaporated under reduced pressure, toluene (50 mL) was added to the concentrated residue, and the mixture was concentrated again under reduced pressure. To the concentrated residue was added toluene (50 mL), and a solution of the obtained ethyl 3-(5-bromo-2-fluoro-4-methoxyphenyl)-3-oxopropionate in toluene was directly used in the next step.

Step 4

Synthesis of ethyl 2-(5-bromo-2-fluoro-4-methoxybenzoyl)-3-dimethylaminoacrylate

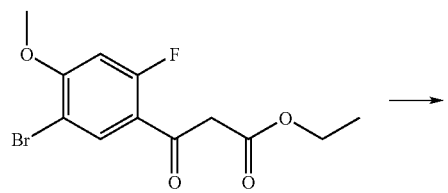

Under a nitrogen atmosphere, to a solution of ethyl 3-(5-bromo-2-fluoro-4-methoxyphenyl)-3-oxopropionate obtained in the above-mentioned Step 3 in toluene was added N,N-dimethylformamide dimethyl acetal (5.53 g). After stirring at 80° C. for 2 hr, the completion of the reaction was confirmed by HPLC. The reaction mixture was cooled to room temperature to give a solution of ethyl 2-(5-bromo-2-fluoro-4-methoxybenzoyl)-3-dimethylaminoacrylate in toluene. The reaction mixture was directly used in the next step.

Step 5

Synthesis of ethyl 2-(5-bromo-2-fluoro-4-methoxybenzoyl)-3-((S)-1-hydroxymethyl-2-methylpropylamino)acrylate

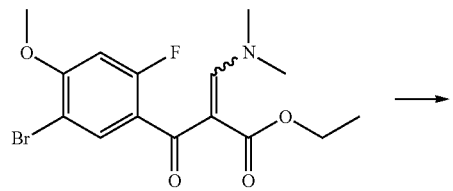

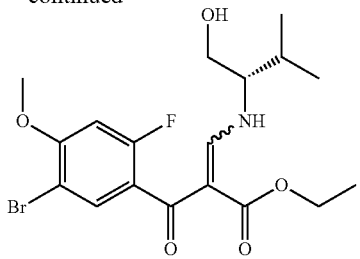

Under a nitrogen atmosphere, to the reaction mixture of the above-mentioned Step 4 was added L-valinol (4.56 g). After stirring at room temperature for 1 hr, the completion of the reaction was confirmed by HPLC. Water (50 mL) was added to the reaction mixture, and after stirring, the toluene layer was separated. The toluene layer was further washed successively with 1 mol/L hydrochloric acid (30 mL, twice), water (50 mL), 5% aqueous sodium hydrogencarbonate solution (50 mL) and 10% brine (50 mL). After washing, toluene was evaporated under reduced pressure, toluene (50 mL) was added to the concentrated residue, and the mixture was concentrated again under reduced pressure. The obtained ethyl 2-(5-bromo-2-fluoro-4-methoxybenzoyl)-3-((S)-1-hydroxymethyl-2-methylpropylamino)acrylate (19.5 g) was directly used in the next step.

Step 6

Corresponding to Scheme 2, Step 6'

Synthesis of ethyl 6-bromo-7-methoxy-1-((S)-1-hydroxymethyl-2-methylpropyl)-4-oxo-1,4-dihydroquinoline-3-carboxylate

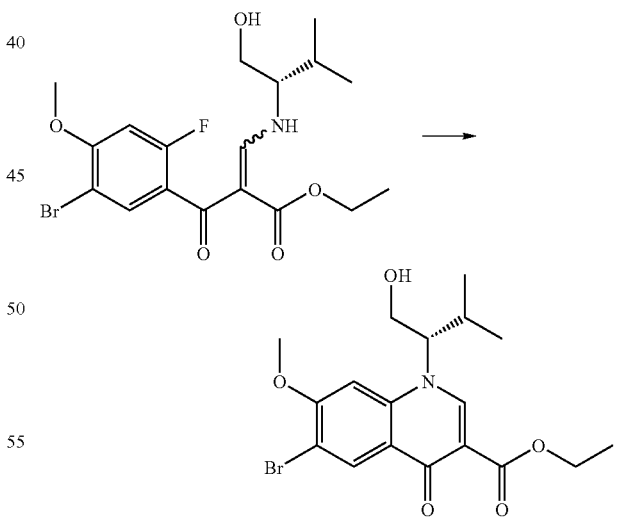

Ethyl 2-(5-Bromo-2-fluoro-4-methoxybenzoyl)-3-((S)-1-hydroxymethyl-2-methylpropylamino)acrylate (19.5 g) was dissolved in DMF (50 mL), and potassium carbonate (8.32 g) was added. After stirring at 45° C. for 8 hr, the completion of the reaction was confirmed by HPLC. Toluene (100 mL) and 5% brine (100 mL) were added to the reaction mixture, and after stirring, the toluene layer was separated. The toluene layer was washed 3 times with 10% brine (100 mL). After

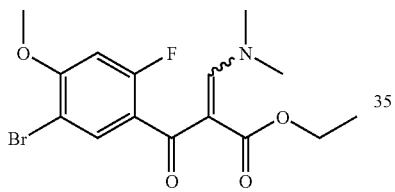

washing, toluene was evaporated under reduced pressure. Toluene (50 mL) was added to the concentrate residue, and the mixture was concentrated again under reduced pressure. The obtained crude ethyl 6-bromo-7-methoxy-1-((S)-1-hydroxymethyl-2-methylpropyl)-4-oxo-1,4-dihydroquinoline-3-carboxylate (17.4 g) was directly used in the next step.

Step 7

Corresponding to Scheme 2, Step 7'

Synthesis of ethyl 6-bromo-1-[(S)-1-(tert-butyldimethyl-silanyloxymethyl)-2-methylpropyl]-7-methoxy-4-oxo-1,4-dihydroquinoline-3-carboxylate

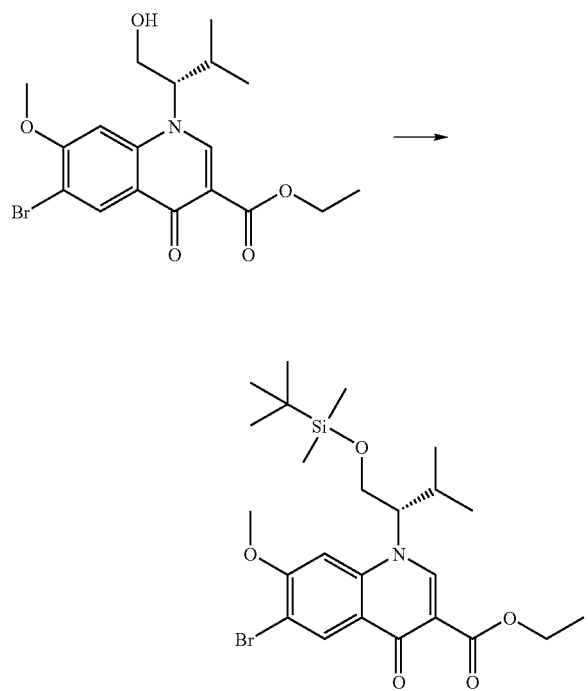

Under a nitrogen atmosphere, ethyl 6-bromo-7-methoxy-1-((S)-1-hydroxymethyl-2-methylpropyl)-4-oxo-1,4-dihydroquinoline-3-carboxylate obtained in the above-mentioned Step 6 and imidazole (3.55 g) were suspended in THF (40 mL). A solution (13.3 g) of 50% tert-butyldimethylsilyl chloride in toluene was added dropwise at 65° C. After stirring at 65° C. for 1 hr, the completion of the reaction was confirmed by HPLC. After cooling, ethyl acetate (80 mL) and water (40 mL) were added to the reaction mixture, and the organic layer was separated. The organic layer was washed with water (40 mL) and twice 10% brine (100 mL). After washing, the solvent was evaporated under reduced pressure to give crude ethyl 6-bromo-1-[(S)-1-(tert-butyldimethyl-silanyloxymethyl)-2-methylpropyl]-7-methoxy-4-oxo-1,4-dihydroquinoline-3-carboxylate (20.55 g). The crude product was recrystallized from toluene (100 mL) to give ethyl 6-bromo-1-[(S)-1-(tert-butyldimethyl-silanyloxymethyl)-2-methylpropyl]-7-methoxy-4-oxo-1,4-dihydroquinoline-3-carboxylate as purified white crystals (14.8 g, 70%).

Step 8

Synthesis of ethyl 1-[(S)-1-(tert-butyldimethyl-silanyloxymethyl)-2-methylpropyl]-6-(3-chloro-2-fluorobenzyl)-7-methoxy-4-oxo-1,4-dihydroquinoline-3-carboxylate

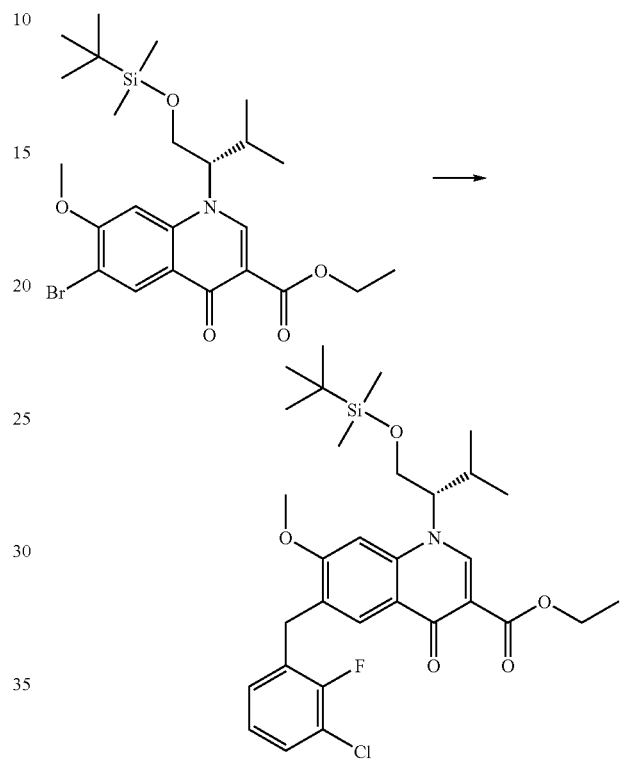

Under a nitrogen atmosphere, tris(dibenzylideneacetone)dipalladium(0) (332 mg) and triphenylphosphine (299 mg) were added to THF (40 mL), and the mixture was stirred at room temperature for 1 hr. Ethyl 6-bromo-1-[(S)-1-(tert-butyldimethyl-silanyloxymethyl)-2-methylpropyl]-7-methoxy-4-oxo-1,4-dihydroquinoline-3-carboxylate (10.0 g) obtained in the above-mentioned Step 7/1-methyl-2-pyrrolidinone (80 mL) solution, and 29% CFZB (3-chloro-2-fluorobenzylzinc bromide)/THF solution (26.2 g) were successively added dropwise at room temperature. After dropwise addition, the mixture was stirred at 65° C. for 3 hr, and the completion of the reaction was confirmed by HPLC. After cooling, toluene (50 mL) and 12.5% aqueous ammonium chloride solution (100 mL) were added to the reaction mixture and, after sufficient stirring, the aqueous layer was discarded. The organic layer was washed successively with 25% aqueous ammonium chloride solution (50 mL), twice with 2% aqueous ethylenediamine solution (50 mL), and with 10% aqueous sodium chloride solution (50 mL). After washing, the solvent is evaporated under reduced pressure. To the concentrated residue was added isopropanol (50 mL) to give a solution of ethyl 1-[(S)-1-(tert-butyldimethyl-silanyloxymethyl)-2-methylpropyl]-6-(3-chloro-2-fluorobenzyl)-7-methoxy-4-oxo-1,4-dihydroquinoline-3-carboxylate in isopropanol, which was directly used in the next step.

Step 9

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid

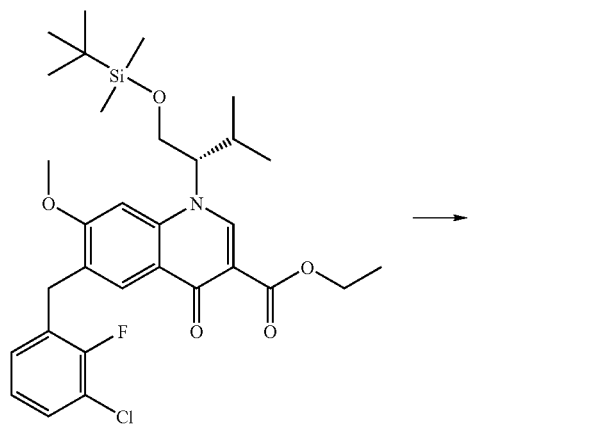

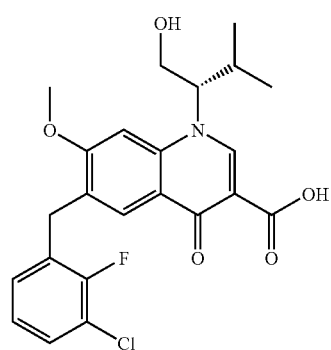

To a solution of ethyl 1-[(S)-1-(tert-butyldimethyl-silanyloxymethyl)-2-methylpropyl]-6-(3-chloro-2-fluorobenzyl)-7-methoxy-4-oxo-1,4-dihydroquinoline-3-carboxylate in isopropanol was added 1 mol/L aqueous sodium hydroxide solution (40 mL). After stirring at 70° C. for 5 hr, the completion of the reaction was confirmed by HPLC. After cooling the reaction mixture to room temperature, activated carbon (Sirasagi A, 1.0 g) was added. After stirring, the mixture was filtered through powder cellulose (KC FLOCK). The reaction vessel and the filter were washed with isopropanol (10 mL)/water (10 mL) solution, and combined with the filtrate. To the obtained filtrate were added water (40 mL) and heptane (50 mL) and, after stirring, the organic layer was removed. The aqueous layer was washed again with heptane (50 mL). The aqueous layer was ice-cooled, the concentrated hydrochloric acid (4.17 g) was added dropwise at 10° C., and methylisopropylketone (100 mL) was added. After the addition, the mixture was stirred at room temperature, and the aqueous layer was discarded. The organic layer was successively washed with 8.5% sodium hydrogencarbonate (50 mL, twice), sodium chloride (2.5 g)/0.5 mol/L hydrochloric acid (50 mL) solution, and 10% brine (50 mL). After washing, the solvent was evaporated under reduced pressure. Toluene (30 mL) was added to the obtained concentrated residue, and the mixture was concentrated again under reduced pressure to give crude 6-(3-chloro-2-fluorobenzyl)-1-((S)-1-hydroxymethyl-2-methylpropyl)-7-methoxy-4-oxo-1,4-dihydroquinoline)-3-carboxylic acid (9.46 g). The crude product was recrystallized from toluene (50 mL) to give 6-(3-chloro-2-fluorobenzyl)-1-((S)-1-hydroxymethyl-2-methylpropyl)-7-methoxy-4-oxo-1,4-dihydroquinoline)-3-carboxylic acid as purified white crystals (7.26 g, 85%).

The above-mentioned 6-(3-chloro-2-fluorobenzyl)-1-((S)-1-hydroxymethyl-2-methylpropyl)-7-methoxy-4-oxo-1,4-dihydroquinoline)-3-carboxylic acid (4.00 g) was recrystallized from ethanol (30 mL)/water (20 mL) to give a product of 6-(3-chloro-2-fluorobenzyl)-1-((S)-1-hydroxymethyl-2-methylpropyl)-7-methoxy-4-oxo-1,4-dihydroquinoline)-3-carboxylic acid (3.74 g, 94%).

The compound of Step 9 of Example 2 was identified as compound (10).

TABLE 8

| Structural formula | $^1$H-NMR | MS (ESI) M+ |
|---|---|---|
| (10) | (DMSO-$d_6$, 400 MHz) δ (ppm): 0.73(d, 3H, J = 6.7 Hz), 1.16(d, 3H, J = 6.7 Hz), 2.30-2.55(m, 1H), 3.75-3.85(m, 1H), 4.00-4.10(m, 1H), 4.04(s, 3H), 4.12 (s, 2H), 4.80-4.95(m, 1H), 5.15-5.25(m, 1H), 7.10-7.20(m, 1H), 7.20-7.25(m, 1H), 7.40-7.55 (m, 2H), 8.10(s, 1H), 8.94(s, 1H), 15.5(s, 1H). | 448 |

The property data of the title compound in each step is as follows.

TABLE 9

| Structural formula | ¹H-NMR | MS (ESI) M+ |
|---|---|---|
| (Step 1) | (DMSO-d$_6$, 300 MHz) δ (ppm): 3.87-3.97(m, 3H), 7.14-7.17(d, 1H), 7.99-8.01(d, 1H), 13.20 (s, 1H). | 249 |
| (Step 5) | (DMSO-d$_6$, 300 MHz) δ (ppm): 0.86-1.02(m, 9H), 1.91-1.94(m, 1H), 3.53-3.60(m, 2H), 3.89-3.97 (m, 5H), 4.96-5.01(m, 1H), 6.99-7.05(m, 1H), 7.49-7.51(d, 1H), 8.10-8.15(d, 1H), 10.77-10.86(m, 1H). | |
| (Step 6) | (DMSO-d$_6$, 400 MHz) δ (ppm): 0.74-0.75(d, 3H), 1.11-1.15(d, 3H), 1.22-1.33(m, 3H), 2.30(m, 1H), 3.70-3.81(m, 1H), 3.91(m, 1H), 4.10(s, 3H), 4.20-4.26(m, 2H), 4.67(m, 1H), 5.14-5.15(m, 1H), 7.38(s, 1H), 8.35(s, 1H), 8.67(s, 1H). | 412 |
| (Step 7) | (DMSO-d$_6$, 400 MHz) δ (ppm): 0.00(d, 6H, J = 4.8 Hz), 0.82(s, 9H), 0.85(d, 3H, J = 6.6 Hz), 1.24(d, 3H, J = 6.2 Hz), 1.34(t, 3H, J = 7.3 Hz), 2.40-2.48(m, 1H), 3.90-3.98(m, 1H), 4.12(s, 3H), 4.12-4.17(m, 1H), 4.23-4.34(m, 2H), 4.80-4.87 (m, 1H), 7.47(s, 1H), 8.43(s, 1H), 8.70(s, 1H). | 526 |

The analysis conditions of HPLC used in the above-mentioned Example 2 are described in the following.
HPLC Analysis Conditions
Analysis Method 1 (Example 2, Step 1-Step 6)
Analysis Conditions
  column: Inertsil ODS-80A 5 μm (150 mm×4.6 mm i.d.) (GL Sciences Inc)
  column temperature: 40° C.
  mobile phase: mobile phase A: 0.01% TFA (trifluoroacetic acid) aqueous solution
  mobile phase B: 0.01% TFA acetonitrile solution
Gradient Program

TABLE 10

|  | time (min) | | | | | |
|---|---|---|---|---|---|---|
|  | 0 | 10 | 20 | 30 | 31 | 40 |
| mobile phase A | 55 | 55 | 20 | 20 | 55 | stopped |
| mobile phase B | 45 | 45 | 80 | 80 | 45 | | flow rate: 1.0 mL/min
detection: UV 220 nm
analysis time: 35 min
Analysis Method 2 (Example 2, Step 7 and Step 9)
Analysis Conditions
  column: Inertsil ODS-80A 5 μm (150 mm×4.6 mm i.d.) (GL Sciences Inc)
  column temperature: 40° C.
  mobile phase: mobile phase A: 10 mM phosphate buffer (pH 6.9)
  mobile phase B: acetonitrile (HPLC grade)
Gradient Program

TABLE 11

|  | time (min) | | | | | |
|---|---|---|---|---|---|---|
|  | 0 | 8 | 25 | 50 | 51 | 60 |
| mobile phase A | 55 | 55 | 20 | 20 | 55 | stopped |
| mobile phase B | 45 | 45 | 80 | 80 | 45 | | flow rate: 1.0 mL/min
detection: UV 220 nm
analysis time: 55 min
Analysis Method 3 (Example 2, Step 8)
Analysis Conditions
  column: Inertsil ODS-80A 5 μm (150 mm×4.6 mm i.d.) (GL Sciences Inc)
  column temperature: 40° C.
  mobile phase: mobile phase A: 10 mM phosphate buffer (pH 6.9)
  mobile phase B: acetonitrile (HPLC grade)
Gradient Program

TABLE 12

|  | time (min) | | | | | | | |
|---|---|---|---|---|---|---|---|---|
|  | 0 | 6 | 8 | 28 | 35 | 55 | 56 | 60 |
| mobile phase A | 50 | 50 | 40 | 40 | 20 | 20 | 50 | stopped |

TABLE 12-continued

|  | time (min) | | | | | | | |
|---|---|---|---|---|---|---|---|---|
|  | 0 | 6 | 8 | 28 | 35 | 55 | 56 | 60 |
| mobile phase B | 50 | 50 | 60 | 60 | 80 | 80 | 50 | | flow rate: 1.0 mL/min
detection: UV 220 nm
analysis time: 65 time
This application is based on a patent application Nos. 2006-60274 and 2006-60297 filed in Japan, the contents of which are incorporated in full herein by this reference.

INDUSTRIAL APPLICABILITY

Compounds (6), (7-1), (7-2) and (8) of the present invention are particularly useful as synthetic intermediates for compounds having an extremely high HIV integrase inhibitory activity (see, for example, WO2004/046115).

In addition, the present invention can provide a method of producing a compound having an HIV integrase inhibitory activity in a good yield.

Moreover, the production method of the present invention is useful as a method for industrial mass synthesis because the method does not use a highly dangerous and highly toxic reagent requiring careful handling and can be performed under mild conditions.

The invention claimed is:
1. A method of producing a compound of the following formula (10):

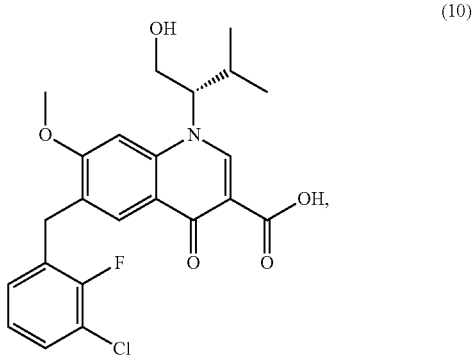 [SMILES: COc1cc2c(cc1Cc1cccc(Cl)c1F)c(=O)c(C(=O)O)cn2[C@H](CO)C(C)C]

(10)

or a salt thereof, comprising
reacting a compound of the following formula (8):

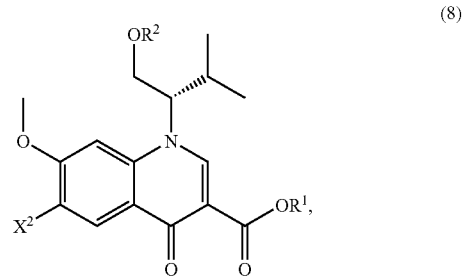

(8)

wherein $R^1$ is a $C_1$-$C_4$ alkyl group, $R^2$ is a hydroxyl-protecting group and $X^2$ is a halogen atom, to produce a compound of the following formula (9):

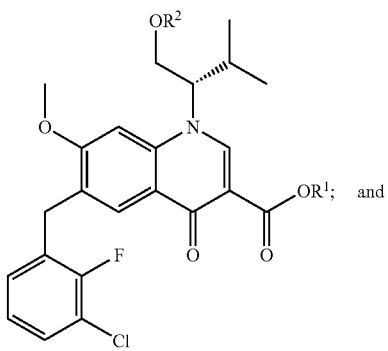
(9)

reacting said compound of the formula (9) to produce the above compound of formula (10) or a salt thereof.

2. A method of producing a compound of the following formula (10):

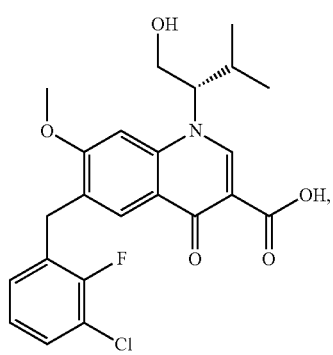
(10)

or a salt thereof, comprising
reacting a compound of the following formula (4-A):

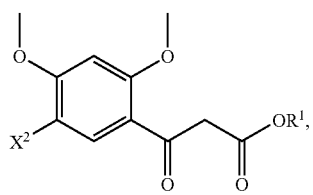
(4-A)

wherein $R^1$ is a $C_1$-$C_4$ alkyl group and $X^2$ is a halogen atom, or a salt thereof
to produce a compound of the following formula (5-A):

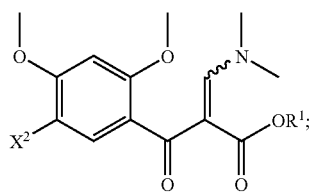
(5-A)

reacting said compound of the formula (5-A) to produce a compound of the following formula (6-A):

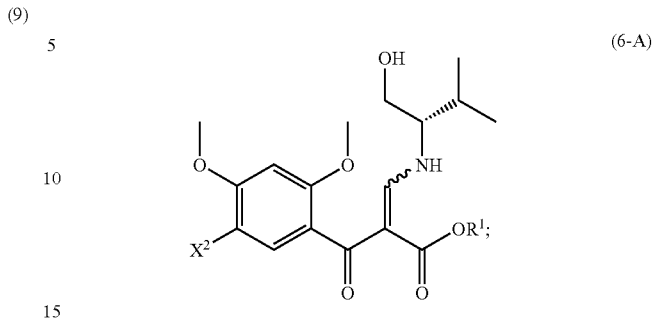
(6-A)

reacting said compound of the formula (6-A) to produce a compound of the following formula (7-1):

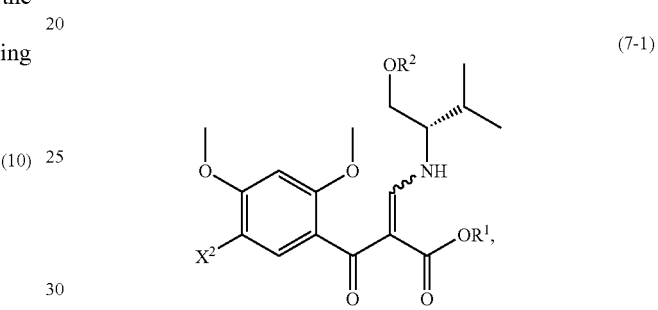
(7-1)

wherein $R^2$ is a hydroxyl-protecting group;
reacting said compound of the formula (7-1) to produce a compound of the following formula (8):

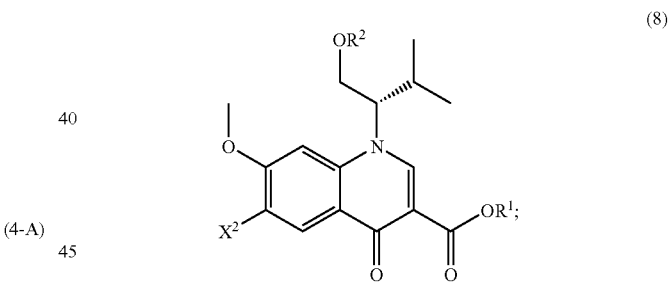
(8)

reacting said compound of the formula (8) to produce a compound of the following formula (9):

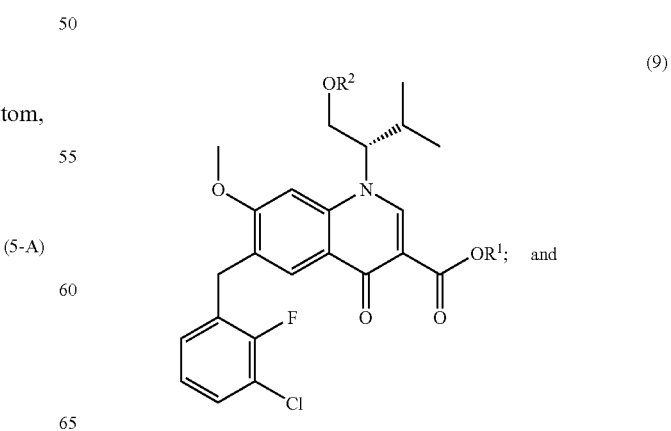
(9)

reacting said compound of the formula (9) to produce the above compound of formula (10) or a salt thereof.

3. A method of producing a compound of the following formula (10):

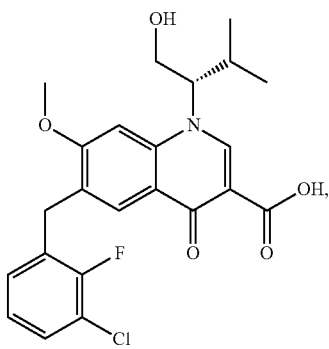
(10)

or a salt thereof, comprising
reacting a compound of the following formula (4-B):

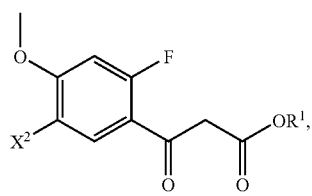
(4-B)

wherein $R^1$ is a $C_1$-$C_4$ alkyl group and $X^2$ is a halogen atom, or a salt thereof
to produce a compound of the following formula (5-B):

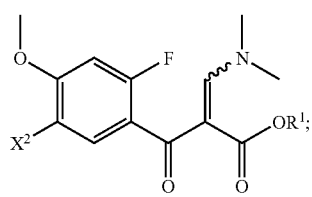
(5-B)

reacting said compound of the formula (5-B) to produce a compound of the following formula (6-B):

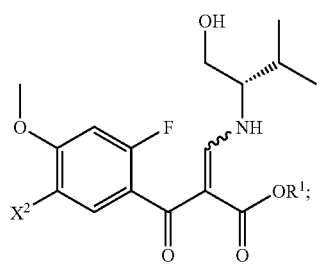
(6-B)

reacting said compound of the formula (6-B) to produce a compound of the following formula (7-2):

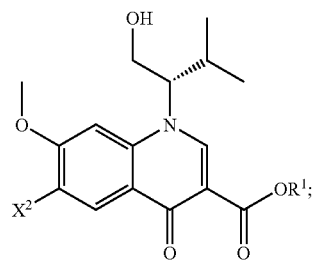
(7-2)

reacting said compound of the formula (7-2) to produce a compound of the following formula (8):

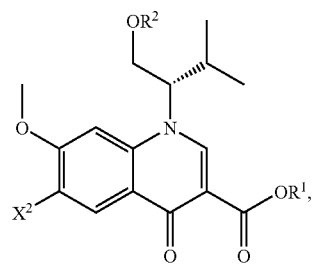
(8)

wherein $R^2$ is a hydroxyl-protecting group;
reacting said compound of the formula (8) to produce a compound of the following formula (9):

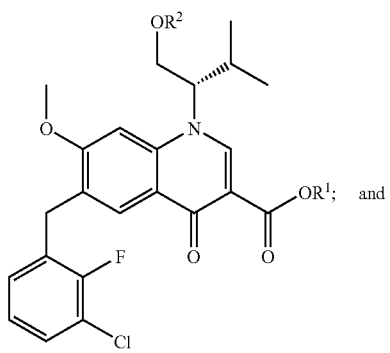
(9)

reacting said compound of the formula (9) to produce the above compound of formula (10) or a salt thereof.

4. A compound of the following formula (8):

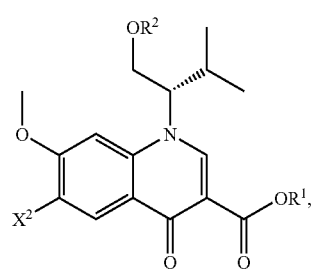
(8)

wherein $R^1$ is a $C_1$-$C_4$ alkyl group, $R^2$ is a hydroxyl-protecting group, and $X^2$ is a halogen atom.

5. A compound of the following formula (7-2):
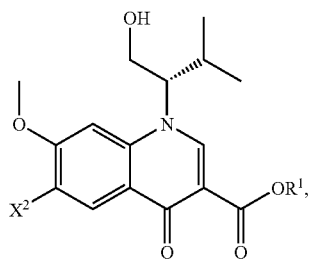
(7-2)
wherein $R^1$ is a $C_1$-$C_4$ alkyl group and $X^2$ is a halogen atom.
* * * * *

UNITED STATES PATENT AND TRADEMARK OFFICE
CERTIFICATE OF CORRECTION

| | | |
|---|---|---|
| PATENT NO. | : 8,420,821 B2 | Page 1 of 1 |
| APPLICATION NO. | : 12/281921 | |
| DATED | : April 16, 2013 | |
| INVENTOR(S) | : Matsuda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1021 days.

Signed and Sealed this
First Day of April, 2014

Michelle K. Lee
*Deputy Director of the United States Patent and Trademark Office*